(12) United States Patent
Habben et al.

(10) Patent No.: US 7,531,723 B2
(45) Date of Patent: *May 12, 2009

(54) MODULATION OF CYTOKININ ACTIVITY IN PLANTS

(75) Inventors: Jeffrey E. Habben, Urbandale, IA (US); Chris Zinselmeier, Grimes, IA (US); Dwight T. Tomes, Van Meter, IA (US); Timothy G. Helentjaris, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 155 days.

This patent is subject to a terminal disclaimer.

(21) Appl. No.: 10/817,483

(22) Filed: Apr. 2, 2004

(65) Prior Publication Data

US 2004/0237147 A1     Nov. 25, 2004

Related U.S. Application Data

(63) Continuation-in-part of application No. 09/545,334, filed on Apr. 7, 2000, now Pat. No. 6,992,237.

(60) Provisional application No. 60/460,718, filed on Apr. 4, 2003, provisional application No. 60/129,844, filed on Apr. 16, 1999.

(51) Int. Cl.
*C12N 15/82* (2006.01)
*A01H 5/00* (2006.01)
*A01H 5/10* (2006.01)

(52) U.S. Cl. .................. 800/320.1; 800/298; 800/290; 800/287; 800/278

(58) Field of Classification Search ............... 800/298, 800/290, 287, 278; 435/320.1
See application file for complete search history.

(56) References Cited

U.S. PATENT DOCUMENTS

| | | | |
|---|---|---|---|
| 4,943,674 A | 7/1990 | Houck et al. | |
| 5,177,307 A | 1/1993 | Houck et al. | |
| 5,689,042 A * | 11/1997 | Amasino et al. | 800/298 |
| 5,780,709 A | 7/1998 | Adams et al. | |
| 5,877,400 A | 3/1999 | Tomes et al. | |
| 6,229,066 B1 | 5/2001 | Morris | |
| 6,329,570 B1 * | 12/2001 | Martineau | 800/290 |
| 6,407,315 B1 | 6/2002 | Jiao et al. | |
| 6,992,237 B1 * | 1/2006 | Habben et al. | 800/298 |
| 2004/0016016 A1 | 1/2004 | Mankin et al. | |

FOREIGN PATENT DOCUMENTS

| | | |
|---|---|---|
| WO | WO 91/01323 | 2/1991 |
| WO | WO 93/07272 | 4/1993 |
| WO | WO 96/26639 | 9/1996 |
| WO | WO 96/29858 | 10/1996 |
| WO | WO 97/05260 | 2/1997 |
| WO | WO 99/06571 | 2/1999 |
| WO | WO 00/11177 | 3/2000 |
| WO | WO 00/63401 | 10/2000 |
| WO | WO 02/078438 | 10/2002 |
| WO | WO 2004/000015 | 12/2003 |

OTHER PUBLICATIONS

Estruch et al (1993, The Plant Journal, 4(2):379-384).*
Roeckel et al (1997, Transgenic Research 6(2):133-141).*
Sa et al (2002, Transgenic Research 11(3):269-278).*
Takei et al (2001, Journal of Biological Chemistry 276(28):26405-26410).*
Gardner et al (1997, NCBI Accession No. V00140).*
Esau, K. "Anatomy of Seed Plants" 2nd edition. John Wiley & Sons. New York, 1977.*
Jackson et al (1994, Development 120:405-413).*
Takei et al (2001, The Journal of Biological Chemistry276(28):26405-26410).*
Zubko et al (The Plant Journal 29(6):797-808).*
U.S. Appl. No. 09/545,334, Habben et al.
Cheikh, N. and R.J. Jones, "Disruption of maize kernel growth and development by heat stress"; Plant Physiol. 106: 45-51 (1994).
Dietrich, J., et al.; "Changes in cytokinins and cytokinin oxidase activity in developing maize kernels and the effects of oxogenous cytokinin on kernel development"; Plant Phyisol. Biochem; 33(3): 327-336 (1995).

(Continued)

*Primary Examiner*—Stuart F. Baum
(74) *Attorney, Agent, or Firm*—Pioneer Hi-Bred Int'l Inc.

(57) ABSTRACT

This invention relates generally to the field of plant molecular biology. More specifically, this invention relates to methods and reagents for the temporally- and/or spatially-regulated expression of genes that affect metabolically effective levels of cytokinins in plants, particularly in plant seeds and related female reproductive tissue. This invention further relates to transgenic plants having enhanced levels of cytokinin expression wherein the transgenic plant exhibits useful characteristics, such as improved seed size, decreased tip kernel abortion, increased seed set during unfavorable environmental conditions, or stability of yield. The present invention also provides compositions and methods for regulating expression of heterologous nucleotide sequences in a plant. Compositions comprise novel nucleotide sequences for seed-preferred promoters known as eep1 and eep2. A method for expressing a heterologous nucleotide sequence in a plant using the promoter sequences disclosed herein is provided. The method comprises transforming a plant cell to comprise a heterologous nucleotide sequence operably linked to one of the promoters of the present invention and regenerating a stably transformed plant from the transformed plant cell.

15 Claims, 10 Drawing Sheets

OTHER PUBLICATIONS

Gan, S. and R.M. Amasino; "Inhibition of leaf senescence by autoregulated production of cytokinin"; Science; 270: 1986-1988 (1995).

Lejeune, P., et al.; "Hormonal control of ear abortion in a stress-sensitive maize (zea mays) inbred"; Auet. J. Plant Physiol.; 25: 481-488 (1988).

Morris, R.O., et al.; "Isolation of a gene encoding a glycosylated cylokinin oxydase from maize"; Biochemical and Biophysical Research Communications; 225: 328-333 (1999).

Riou-Khamlichi, C., et al.; "Cytokinin activation of Arabidopels cell division through a D-type cyclin"; Science; 283: 1541-1544 (1999).

Jones, R.J. and B.M.N. Schreiber; "Role and functio nof cytokinin oxidase in plants"; Plant Growth Regulation; 23(1-2): 123-134 (1997).

Houba-Herin, N., et al.; "Cylokinin Oxidase from Zea Mays: purification, cDNA cloning and expression in moss protoplasts"; The Plant Journal; 17(5): 615-626 (1999).

Rinaldi, A.C. and Comandini, O.; "Cytokinin oxidase: new insight into enzyme properties"; Trends in Plant Science; v.4(4): 127-128 (1999).

Morris, R.O., et al.; "Isolation of a gene encoding a glycosylated cytokinin oxidase from maize"; GenBank Accession AF044603 (1999).

Vantoai, et al.; "Improved biomass production and abiotic stress tolerence of transgenic Arabidopsis containing an autoregulated cytokinin biosynthesis gene"; Plant & Animal Genome VII Conference; 1999.

Roeckel, et al.; "Effects of seed-specific expression of cytokinin biosynthetic gene on canola and tobacco phenotypes"; Transgenic Research; 6: 133-141 (1997).

Ma Qing-Hu, et al.; "Seed-specific expression of the isopentenyl transferase gene (ipt) in transgenic tobacco"; Aust. J. Plant Physiol.; 25: 63-69 (1998).

Roeckel, et al.; "Phenotypic alterations and component analysis of seed yield in transgenic Brassica napus plants expressing the Izs gene"; Physiol Plant 243-249 (1998).

Kaminek, M.; "Progress in cytokinin research"; Trends in Biotechnology; 5: 159-164 (1992).

Takei, et al.; Journal of Biological Chemistry; 276(28): 26405-26410 (2001).

Kusaba, et al.; Plant Physiology; 16(2): 471-476 (1998).

Binns; Annu. Rev. Plant Physiol. Plant Mol. Biol. 45: 173-196 (1994).

Commenn, et al.; The Plant Cell; 6: 1789-1803 (1994).

The Arabidopsis Genome Initiative; Nature; 408 (Dec. 14): 796-815 (2000).

Database EMBL: "Zea mays zag2 gene" XP002300228; May 31, 1995.

Theissen, G., et al; "Structural characterization, chromosomal localization and phytogenetic evaluation of two pairs of AGAMOUS-like MADS-box genes from maize"; Gene; 156(2): 155-166; 1995.

Database EMBL; "Zea mays subsp. mays W22 teosinte branched 1 (tb1) gene, partial sequence"; XP002315672; Jul. 8, 1999.

Wang, R., et al.; "The limits of selection during maize domestication"; Nature; 398(6724): 236-239; Mar. 18, 1999.

Doebley, J., et al.; "The evolution of apical dominance in maize"; Nature; 386(6624) 485-488; Apr. 3, 1997.

Database EMBL; "Zea mays DnaJ-related protein SMDJ1 (mdJ1) gene, complete cds"; XP002315673; Mar. 30, 1998.

Baszczynski, C.L., et al.; "Characterization of a Genomic Clone for a Maize DNAJ-related Gene, ZMDJ1, and Expression Analysis of Its Promoter in Transgenic Plants"; Maydica; 42: 189-201; 1997.

Zubko, E., et al.; "Activation tagging identifies a gene from *Petunia hybrida* responsible for the production of active cytokinins in plants"; The Plant Journal (2002) 29(6):797-808; Blackwell Publishing Ltd; Oxford, UK.

* cited by examiner

Plant Biomass

| Transgene | Plant (g) | Δ (%) | Fresh Wt. Ear (g) | Δ (%) | Total (g) | Δ (%) |
|---|---|---|---|---|---|---|
| Negative | 4519 | | 1957 | | 6476 | |
| Positive | 6426 | 42↑ | 2629 | 34↑ | 9054 | 39↑ |

SEQUENCE LISTING

<160> NUMBER OF SEQ ID NOS: 39

<210> SEQ ID NO 1
<211> LENGTH: 1919
<212> TYPE: DNA
<213> ORGANISM: Agrobacterium tumefaciens
<220> FEATURE:
<221> NAME/KEY: CDS
<222> LOCATION: (690)...(1411)
<223> OTHER INFORMATION: ipt

<400> SEQUENCE: 1

```
ggatcccgtt acaagtattg cacgttttgt aaattgcata ttaatgcaat ctggatgttt      60
aataacgaat gtaatggcgt agaaatatgt attttattgt atttatcttt cactatgttg     120
aagtttgcaa taatatgcta atgtaaaatt aaaaaattat gtactgccgc atttgttcaa     180
atggcgccgt tatttcaaaa atatctttga ttttgttacg aggacaacga ctgcaggaag     240
taaataaaag acgctgttgt taagaaattg ctatcatatg tgcccagcta tagggccatt     300
taagttcaat tgtgaaatag ccgcccttat tttgacgtct catcaaatca aatattaaaa     360
aatatctcac tctgtcgcca gcaatgatgt aataaccgca gaaagtgag agtaaatcgc     420 ggaaaaacgt cgccgagtgg catgaatagc ggcctccgta ttgctgattt agtcagcttt     480
atttgactta agggtgccct cgttagtgac aaattgcttt caaggagaca gccatgcccc     540
```

```
acactttgtt gaaaaacaag ttgccttttg ggaagaacct aaagccactt gctcttcaag      600
gaggaatatc gaggaagaga atataacagc ctctggtaca gacttctctt gtgcaaaaat      660
caatttgtat tcaacatatc gcaagaccg atg gat cta cgt cta att ttc ggt        713
                                Met Asp Leu Arg Leu Ile Phe Gly
                                  1               5 cca act tgc aca gga aag aca tcg act gcg ata gct ctt gcc cag cag        761
Pro Thr Cys Thr Gly Lys Thr Ser Thr Ala Ile Ala Leu Ala Gln Gln
         10                  15                  20 act ggc ctc cca gtc ctc tcg ctc gat cgc gtc caa tgc tgt cct caa        809
Thr Gly Leu Pro Val Leu Ser Leu Asp Arg Val Gln Cys Cys Pro Gln
 25                  30                  35                  40 cta tca acc gga agc ggg cga cca aca gtg gaa gaa ctg aaa gga acg        857
Leu Ser Thr Gly Ser Gly Arg Pro Thr Val Glu Glu Leu Lys Gly Thr
                 45                  50                  55 act cgt ctg tac ctt gat gat cgc cct ttg gta aag ggt atc att aca        905
Thr Arg Leu Tyr Leu Asp Asp Arg Pro Leu Val Lys Gly Ile Ile Thr
             60                  65                  70 gcc aag caa gct cat gaa cgg ctc att gcg gag gtg cac aat cac gag        953
Ala Lys Gln Ala His Glu Arg Leu Ile Ala Glu Val His Asn His Glu
 75                  80                  85 gcc aaa ggc ggg ctt att ctt gag gga gga tct atc tcg ttg ctc agg       1001
Ala Lys Gly Gly Leu Ile Leu Glu Gly Gly Ser Ile Ser Leu Leu Arg
         90                  95                 100 tgc atg gcg caa agt cgt tat tgg aac gcg gat ttt cgt tgg cat att       1049
Cys Met Ala Gln Ser Arg Tyr Trp Asn Ala Asp Phe Arg Trp His Ile
105                 110                 115                 120 att cgc aac gag tta gca gac gag gag agc ttc atg agc gtg gcc aag       1097
Ile Arg Asn Glu Leu Ala Asp Glu Glu Ser Phe Met Ser Val Ala Lys
                125                 130                 135 acc aga gtt aag cag atg tta cgc ccc tct gca ggt ctt tct att atc       1145
Thr Arg Val Lys Gln Met Leu Arg Pro Ser Ala Gly Leu Ser Ile Ile
            140                 145                 150 caa gag ttg gtt caa ctt tgg agg gag cct cgg ctg agg ccc ata ctg       1193
Gln Glu Leu Val Gln Leu Trp Arg Glu Pro Arg Leu Arg Pro Ile Leu
        155                 160                 165 gaa ggg atc gat gga tat cga tat gcc ctg cta ttt gct acc cag aac       1241
Glu Gly Ile Asp Gly Tyr Arg Tyr Ala Leu Leu Phe Ala Thr Gln Asn
170                 175                 180 cag atc acg ccc gat atg cta ttg cag ctc gac gca gat atg gag aat       1289
Gln Ile Thr Pro Asp Met Leu Leu Gln Leu Asp Ala Asp Met Glu Asn
185                 190                 195                 200 aaa ttg att cac ggt atc gct cag gag ttt cta atc cat gcg cgt cga       1337
Lys Leu Ile His Gly Ile Ala Gln Glu Phe Leu Ile His Ala Arg Arg
                205                 210                 215 cag gaa cag aaa ttc cct ttg gtg ggc gcg aca gct gtc gaa gcg ttt       1385
Gln Glu Gln Lys Phe Pro Leu Val Gly Ala Thr Ala Val Glu Ala Phe
            220                 225                 230 gaa gga cca cca ttt cga atg tga ta gattgcacca gttttgtttc              1431
Glu Gly Pro Pro Phe Arg Met  *
                235 agacttgtcg ctatttgaat aagatgttcg ttctttgttg tgttggtgtg ttgtgataga     1491 ggcaagtggt ttgaaacttg tttttactgg tttattttca gtctcttgga cgatgtttta     1551 caaatataat attgtgaaaa ttgtggtttt atattcgtag aacgaaataa atggtaagta     1611 tagccgttat caaaatttag caaaaattgt taaaggttct tttatgcggt gaggttgtcg     1671 actttcatc attgtcgcgt aaggagttac ggatatccat aactgtaaaa acgccgcaga      1731 atttacgggt ggtgcattta gtttgccgtt caacatgatt ttggcaatag ttggtaacca     1791
```

```
agcactagcc aaccgttcga taatcactta atcgatggaa ccgttcagct ttccttcgtg   1851
aggctgctct tgatgatgag ctgccgtcta gttttttataa cgccgggtta cgcattatag   1911
acaagctt                                                              1919
```

<210> SEQ ID NO 2
<211> LENGTH: 239
<212> TYPE: PRT
<213> ORGANISM: Agrobacterium tumefaciens

<400> SEQUENCE: 2

```
Met Asp Leu Arg Leu Ile Phe Gly Pro Thr Cys Thr Gly Lys Thr Ser
 1               5                  10                  15

Thr Ala Ile Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Asp Asp Arg
    50                  55                  60

Pro Leu Val Lys Gly Ile Ile Thr Ala Lys Gln Ala His Glu Arg Leu
65                  70                  75                  80

Ile Ala Glu Val His Asn His Glu Ala Lys Gly Gly Leu Ile Leu Glu
                85                  90                  95

Gly Gly Ser Ile Ser Leu Leu Arg Cys Met Ala Gln Ser Arg Tyr Trp
            100                 105                 110

Asn Ala Asp Phe Arg Trp His Ile Ile Arg Asn Glu Leu Ala Asp Glu
        115                 120                 125

Glu Ser Phe Met Ser Val Ala Lys Thr Arg Val Lys Gln Met Leu Arg
    130                 135                 140

Pro Ser Ala Gly Leu Ser Ile Ile Gln Glu Leu Val Gln Leu Trp Arg
145                 150                 155                 160

Glu Pro Arg Leu Arg Pro Ile Leu Glu Gly Ile Asp Gly Tyr Arg Tyr
                165                 170                 175

Ala Leu Leu Phe Ala Thr Gln Asn Gln Ile Thr Pro Asp Met Leu Leu
            180                 185                 190

Gln Leu Asp Ala Asp Met Glu Asn Lys Leu Ile His Gly Ile Ala Gln
        195                 200                 205

Glu Phe Leu Ile His Ala Arg Arg Gln Glu Gln Lys Phe Pro Leu Val
    210                 215                 220

Gly Ala Thr Ala Val Glu Ala Phe Glu Gly Pro Pro Phe Arg Met
225                 230                 235
```

<210> SEQ ID NO 3
<211> LENGTH: 2085
<212> TYPE: DNA
<213> ORGANISM: Zea mays
<220> FEATURE:
<221> NAME/KEY: promoter
<222> LOCATION: (1)...(2085)
<223> OTHER INFORMATION: zag2.1

<400> SEQUENCE: 3

```
agcttcgtgt gttccttcga tcggtcacag tttgattcct gctcaccaca tattttgcc    60 gcgtgggagg gaggccacga ctggtggcag aacagcgaga ggcagactac ccttacagcc   120
ttaataactc ttatatcttc tactataaca tcaaaataag acgtagtgtg gtggatatgt   180
tgtctctaat ttagcagcag gtcttgagtt tgattcacaa ttcttgcaga tttattttt   240
```

```
gagccataac agggatgagg gcaaaatagg aaatgaacga catgttaccc ttaccgcctt    300
aataagtagt agagatatcc agtttatacg taattattat tatataaaat gcactgcaca    360
tatattacta ttaccagttt tcttggacat gcacagcaga aaacacgcac acgcagagag    420
gaaaaggaga ggccataaac caaaaggctt aagaatata tgtaaagata tgtctaaatg    480
gctatatctg gttaagcaag ataacagggc tctggtcatc agtagtagtg gccttttgcc    540
cttgcccctc atctctctca cacctctctt ttctcagcct tgcttccgat cgatggatcc    600
catcccactg ccatagtgcc atcctttctt tcccttgcgc gcattgccta gccgccggc     660 cggcctgcta ttaaaccact ttacccccct tctcgttcac gctcgacgca gctcccttt    720 ccttgcttgc ttattgcaag tctctgcaag aacctgctag agaggaacaa ggtagaatag    780
tatcgctttt tccatctaga ggttatctct ttttacatga aaaatttcag ccgtattttc    840
gttctccata tatcagtcct gcgataatat aaatacgcgc gtcttgtgtg atccggcata    900
tgtatagttc ctactaactg atcgagatcg ctctcgtttg tactttctcc ctttgaggaa    960
agagttcccc ttttctgtg cttcaaattc ttgtaaggaa aaccatgcct gcctgccagc    1020
ttcttctgct acttggatga tgattcttat ttgcttactt gatttccgtt ttttttctt    1080 gctttctata tgtatgtatc tgggctgtct tccctgcgt ctcgttacta cgtactaagc    1140
tttggaaggt ttcaactctt tgtatacgat gaggtttctg cccctagtag cagatccgcg    1200
cacgactaga tgtttgagga aaagaaaagg gcaagacgct atatatat gcagcacgca    1260 gtcgcacata tatccagttt tccaatctgc ctcttgcttt atgataattc aacttgcgct    1320
gattatattc ttggctacct agctagaaat gtctaattaa actttgtttg ctagctagat    1380
tttgttgctt cttttcgcat ctgatctttt tatctcttct gagtgctccg caaagccttc    1440
cagtgttgaa gaagctgctg gaagaagaga tgagctttct cttgaaggaa aaagagatga    1500
tcattgccgg tttgttgttg tttcgtgttt ttttagcttc ttgtccccca tttatattcg    1560
cgcctaatga acgagcccgt agatcttgtg ttcttgtggc tggttttgtt ggatctcgat    1620
ctcggttacg tttacatgag tcttgctgcc taacatacat ctgtgttctt tttctaggct    1680
gcgagaaact taactgatcg agtctgtctg gcaggcatcg atctatccag tcgtcagttc    1740
gtcacatccg ctttttcgta tatatcatct tcagattttg tccatctgtc aaatcatgga    1800
aaatctgtcg tctttgcttg tattctcttc tgttattcct gctgcctccg gcggaccaat    1860
tcttgaatcg acccgtgttc ctattccctt ttgttagaca gcccaaatcg cttgctcgat    1920
cgtagtgtac tgtactactg cggctagcta gatcttccaa gctagctata gttcgccggt    1980
ccctttgatc tgcttcacag aacatatata acacttgaac tcttttacgc ttatgagaaa    2040
acttgctgct tgctgctttc agctggtatc gtcgccagcg gatcc                   2085
```

<210> SEQ ID NO 4
<211> LENGTH: 344
<212> TYPE: DNA
<213> ORGANISM: Cauliflower mosaic virus
<220> FEATURE:
<221> NAME/KEY: enhancer
<222> LOCATION: (1)...(344)
<223> OTHER INFORMATION: CaMV35s

<400> SEQUENCE: 4

```
tctagaaatc cgtcaacatg gtggagcacg acactctcgt ctactccaag aatatcaaag     60
atacagtctc agaagaccaa agggctattg agacttttca acaaagggta atatcgggaa    120
```

```
acctcctcgg attccattgc ccagctatct gtcacttcat caaaaggaca gtagaaaagg    180
aaggtggcac ctacaaatgc catcattgcg ataaaggaaa ggctatcgtt caagatgcct    240
ctgccgacag tggtcccaaa gatggacccc cacccacgag gagcatcgtg gaaaagaag     300 acgttccaac cacgtcttca aagcaagtgg attgatgtga tgct                     344
```

<210> SEQ ID NO 5
<211> LENGTH: 2198
<212> TYPE: DNA
<213> ORGANISM: Zea mays
<220> FEATURE:
<221> NAME/KEY: promoter
<222> LOCATION: (1)...(2198)
<223> OTHER INFORMATION: ZmMADS

<400> SEQUENCE: 5

```
ccttttctt tttctccaca acatgaacct tactagaaca ctgccccact taaagaatg     60 agggtagaac tcttgaatct tagggatttg aactccttgc agtacctcat aacaaggtg    120 ttacatgtcc ttcttctgct gttgctgctt gagcaggata tagagagatg accgacaccg   180
ggttgatctt gggacaacct tcttctcatc ttttcttcgt tgttttcttt tctattctca   240 ctacctttt ctttctcttt gttcttccca ctggaggatt ctatcaaaaa gtattaccat    300
catacagagg aggaacccga agactatgaa ccatgtacaa cagtcttcaa cccaagaatc   360
accaagcatt gtgatcttag gggcgaggga gtggaaaatg gagttgcttg tgatttggca   420
gagggaattt tatcaggagt gttttgcttt gagtggaatg ggaactgagg gagttgttgg   480 ggggggggg tttataggcg agtgggagtg ctcgggtgcg gagtgtggtg atggaacagg    540
tgacatgagg tagcaggtcg atggaggggg gctgttgccg gcgatgatgg cggcggtggg   600
tgcgctgcaa aggagggcgt ggggcggtgg tagtgcgcat ggaggcgggc acgcgtgcgg   660
ggggcacaag tgagtggtgg ggtcgatgac cctgatgttt gtggtctctg gttccaagaa   720
tctttgtctc tctttatgat aataacttct tttgtcgtcc ttttctgttt actttgactc   780
aggggcagtg ctttgattct cacggtcggt ccttttgact gagtgactgg acatgtttct   840
tctgtagcat tgtacaacat gtactttgtg caagctacaa ggccacattt tttgaagcat   900
agattctttc ccccaaacaa tttatacaaa tatgcaaggc tacacttctt gtatttctat   960
aacattgtac attcatgaca gaggctcaaa agcttgtaaa ttttgtgcag gtttaattca  1020
tgtaaagttc ccttgtagag tcatgacaac atcgtactat aaaattattc tacaaaaacc  1080
acacatgacc cccatgttat ttggtgacaa tacagaaacc acacatctag tgatgatata  1140
acactgtaca gaagccacaa attataatat ataaaacact atacaaagta tccaaataaa  1200
gcctaatagg tatggagggt aacctgaatc tttcctaata ataatgaata atctacaata  1260
atgatttgtt tggacaaaga gaattaaacg gtattgagtg ggctaaaatt ccttgttatt  1320 caaaccctc aatcacagtt tctccgaggg aaaaagaaac aggggaggac actcaggctg    1380
ttcacaatag ggatttcata tcgctctttc aacaatgcc acatcatcaa aagtgttatg    1440
aaactaaaaa tgaaataata cttctcaatg caaactttca ttttcataga ttaatatact   1500
aattaaatga tgcaactaaa taaccaatag atgttagtaa aatatggtaa gattaaacaa   1560
accactatca atggacattt cacatagttt ccaagacttt gaaaacgggt tgacatgatt   1620
tcatccacat caaactaatt ttatctctga aacccattca ttttaaatga tatggcataa   1680
cgtccaaaat gctgacgtga cataccatta aatgtgcatg aaactcccat aaaacttta    1740 ttgataatag cctcacagac atccggtcct acacccgtgt ggacccatca gccagacgcc   1800
```

```
ctgcagcaaa cgcgacgttt gacttgccat ctcgctccct tgtgcccgac cgaccctgga    1860
aggctggact ggaactggaa caagcaaaat ggaaaaaacc atatctcacc actgaaccgc    1920
acccttccgg cccacgccag gctcgaccaa tccctgcccc gcgcgccctg acgagcgcat    1980
cactcgaacg ccggcctcgc taggcccatc cttctggccc gcaataacga tccccgtcat    2040
gatccgacgg tctagctgcc tccacgccgc tccaaaaccc ccgcgtccaa tcaaaacacg    2100
acagcgggac gagcgaaacc accgtggttt cgccaaaccg ctttccttcc catctaaaac    2160 cgcccccctcc cttcctcttc tcctagctct cttgcctg                          2198

<210> SEQ ID NO 6
<211> LENGTH: 1470
<212> TYPE: DNA
<213> ORGANISM: Zea mays
<220> FEATURE:
<221> NAME/KEY: promoter
<222> LOCATION: (1)...(1470)
<223> OTHER INFORMATION: ckx1-2

<400> SEQUENCE: 6
gagctcgccc ttgcatgctt gagtcatatc ttggaaaaaa aaactgtaac ttaaagtatg      60
atctatatat ggattatttg gatgggatgt catttcgta tcaccaacca aaattacagt     120
ttggtcgtgc gtagaaattc tacctactag ctgaaacaac ggctgctatg tataactact     180
ggtactggaa agaatattag tcattgactc aaaattagaa tgcatgtgta agtcatgcgt     240
gctaatttgt tctatcagca ttcggcgaat tccgaagtcc gtacgtgttg ttcgtggagg     300
agaggaaaac atcagaaatg acaaaactag acggcgtgtg cttctacact gaattcatca     360
acatttgttt tactttttact agagaatggc atcagatgga aaaccgctga aaaacaaga     420 aaacaattgg accccaaata tgtacagacg ctagctatag ccagccacac tgaagttgac     480
atgcggcaac tagctaacca ccttctctga aacactaaca tttgtacctt ggtcgtgtaa     540
gtgtagttag taacgtatgt tgacgcgact taccgaacaa aaatataatt gtcccaatca     600
agctagggac gattgtttgt ttccaaaatg ttgccatttg cttaatcaat cctatattga     660
ttcatggctg ttaaggtgag ataaagcgac aagaaatctc tctctatata tatatataag     720
atcccgaagg ctagcgacat ttttgatagc aaaatatgag aagttggcag gttctggtag     780
caaatcaaat aatatggcca gaataatcgt ggctagcttg attaaacctt cagcttggtg     840
tattttggaa gtcgaccaac cagctgggcc ggggctcgtc gtagtaccaa aattacagcc     900
tgcttccttc gtcgtcctgt acgtaatgca gtacagctgt ctgtctagta gagacgattt     960
tgagcaggca cacacattaa gtgataacat aaaagacggc ttcattttat ttcataacca    1020
aacgatatgg tcaacacaca cctatagcta ccaaatttgt acaactattt agtgcgaaaa    1080
ctatttcatt ctcaagaatt gatcgcttat atttattatt acaggttttt aaatgtataa    1140
atacgctata ttgcatggca aaggggggta ataattaggc aggactatat atataatagt    1200
tttttttcct ttaaattctt gggaggatgg taaagttggt aactaggcac cttgtgcgca    1260
tatttttctg tggtcaaaca gaataaaact agacgggatg cagaattttt ttttccttgg    1320
aaagcagctc atctctgtgt tcgagtacgt aattgaagaa gtatgtgatc gcactacacc    1380
tacacgtatg tgccgccgta tccgtcctat atatatacgg ggtgcaatca cctagttacc    1440
aaacactcac acataagggc ggatccatgg                                    1470

<210> SEQ ID NO 7
```

```
<211> LENGTH: 960
<212> TYPE: DNA
<213> ORGANISM: Zea mays
<220> FEATURE:
<221> NAME/KEY: promoter
<222> LOCATION: (1)...(960)
<223> OTHER INFORMATION: eep1

<400> SEQUENCE: 7
tcaaaccggt catcgtttgt atcatccact gcttgacttg ggaagaagtt aagaacttgg      60
taagacagct gtgagggtgt gacccaacta acccataaat acattttctc caattagtaa     120
attagttttt ttttcttggc ttgattgatg aatcattcaa gttggcatga taagattttg     180
ttcagttatt cgtgtgtctt atgtatgaaa agtgattgaa aaaaattatg gatagttttg     240
acttgctatg gatttaatta cacctaatcg cctccaatcc atatggattg gagggaacca     300
aacaagctct aaggttgata tccgcttcta tatatgctgc atgagcagtt tactgcttta     360
tttttctaca gatgggtcag tgatgaggat tggtgaatgc atcaggtcat tcaaataaat     420
ttttttaacg acagggttat gtaggtgatg acacaccata tattccctaa ctgcctgtct     480
agtgtctact aattactaac gggaaaattg cgtatgctca ttgacgtctc agctgtgcag     540
aagaatctcg gaacatttaa ttcacatata ttgatactac gtgctagctg gtgccatctt     600
cctagctgga tactacttat tgcatcaatt aatttctttt tttgttttct ttcaattgct     660
tccaaggtca aactgaatgc aaaccattac ttgttacaac ggtcctctcc atcctacgct     720
acgcctgatg tgatgtaatg taatcgaagc aagagcctta ttattgtata tttctgttcc     780
taccagggct tgcatggaaa actgccagcc tctcattata ttataaatat acgtatactg     840
atacacatac atgcacacca aaagtactca ggactgtcat ctctcagttg caattgcaaa     900
aaaaatacag agagagagag agagagagag agagatccct accctgcaaa gatatcgacc     960

<210> SEQ ID NO 8
<211> LENGTH: 1224
<212> TYPE: DNA
<213> ORGANISM: Zea mays
<220> FEATURE:
<221> NAME/KEY: promoter
<222> LOCATION: (1)...(1224)
<223> OTHER INFORMATION: end2

<400> SEQUENCE: 8
tactataggg cacgcgtggt cgacggcccg ggctggtaaa aagtaattga acccaaaata      60
tcatggtatg tttggtgaag acagtgatca gtgattttt tatatctata tatatatcaa     120
agatacttga ttttctagaa ggttcttttt gttgttttcc cttatgtttt tacgcatgat     180
gcaattcttt ttgagaggtt tccgatgcat tgatgttatt gtattatctc ctatatatag     240
gtcgacgtac attatgtatt gcaataacca gttaactgga tccagcttcg cttagttttt     300
agttttggc agaaaaaatg atcaatgttt cacaaaccaa atatttttat aacttttgat     360
gaaagaagat caccacggtc atatctaggg gtggtaacaa attgcgatct aaatgtttct     420
tcataaaaaa taaggcttct taataaattt tagttcaaaa taaatacgaa taagtctga     480
ttctaatctg attcgatcct taaatttat aatgcaaaat ttagagctca ttaccacctc     540
tagtcatatg tctagtctga ggtatatcca aaaagccctt tctctaaatt ccacacccaa     600
ctcagatgtt tgcaaataaa tactccgact ccaaaatgta ggtgaagtgc aactttctcc     660
attttatatc aacatttgtt atttttttgtt taacatttca cactcaaaac taattaataa     720
aatacgtggt tgttgaacgt gcgcacatgt ctcccttaca ttatgttttt ttatttatgt     780
```

| attattgttg tttcctccg aacaacttgt caacatatca tcattggtct ttaatattta | 840 |
| tgaatatgga agcctagtta tttacacttg gctacacact agttgtagtt ttgccacttg | 900 |
| tctaacatgc aactctagta gttttgccac ttgcctggca cgcgactcta gtattgacac | 960 |
| ttgtatagca ataatgcca atacgacacc tggccttaca tgaaacatta ttttttgacac | 1020 |
| ttgtatacca tgcaacatta ccattgacat ttgtccatac acattatatc aaatatattg | 1080 |
| agcgcatgtc acaaactcga tacaaagctg gatgaccctc cctcaccaca tctataaaaa | 1140 |
| cccgagcgct actgtaaatc actcacaaca caacacatat cttttagtaa cctttcaata | 1200 |
| ggcgtccccc aagaactagt aaac | 1224 |

<210> SEQ ID NO 9
<211> LENGTH: 1433
<212> TYPE: DNA
<213> ORGANISM: Zea mays
<220> FEATURE:
<221> NAME/KEY: promoter
<222> LOCATION: (1)...(1433)
<223> OTHER INFORMATION: lec1

<400> SEQUENCE: 9

| tcctaatctt caaataacca tctcaaaagt tttttaaaac atcttttgag gatatgtatc | 60 |
| ccatagccct agagcgctaa attgactact tttagtcgat taaaaggtat tagacatcct | 120 |
| tacaagtcct aagtatcaaa tcaccttcta tcggctatac acaactaacg gaagttatct | 180 |
| ctagtcacac taacttatgt cggtttccgc atggcagatc aaaattagct aacttttgtt | 240 |
| ggctaataag agcaattcca aaagaacgtg taaactaatc tcaaaacaga tattagttaa | 300 |
| gaatagtaat ttttcttact ccaacagttc cctcagtctt ccccaaaaaa ttaagcgttc | 360 |
| cgcatccaca gcctcctctc ggtcgtattt tggtgtgttt catccctccc caatccattt | 420 |
| ctcaacgtat cagatcatcc accgcctacg acgactgtac agtttgcgtc acatatcaca | 480 |
| tttaaaggaa ctgttggagt acccatcata attcactctt aaaaaatttt agcctgctct | 540 |
| caataatcaa ttgggggggt aaaattttta acatcctttc ggatctaatc caacttatgg | 600 |
| aagttagcta gctctggtcg cgctaacttc tgtcgatcgc ctattagcta atactccatc | 660 |
| tgtcccatta tataaggtat aaccaactct gattcaaaga ccaaaaatat acttaattgt | 720 |
| gtctatacca cttcatcgat gtacgtatgc atagaaagag cacatcttat attgtggaac | 780 |
| aagaacaaaa atatggttac gccttatatt ataagacgta gaaatcaatg gtttacaata | 840 |
| gccaagaata gatgttttta tttatttcct atatagatgt ttttatttat ttcctatatg | 900 |
| tttcacaata gccttatatt gtgccgaaaa tttaggcaca cgtgccacga acgtctgaaa | 960 |
| tgtactccgc gcgtattacc atgcactacg acgtacgtag gagtatgtac gttgaaccaa | 1020 |
| gcacacatat atctctgaca cagtacaatg atatactaca caacaacag tactgcccaa | 1080 |
| ttcatccatt ttcacgttcc atcttccgcg tgtgacaact cgatcggcca cgcacgcaga | 1140 |
| cgacgacgga gcagtacttc acagaatcct ccgccactcg tcacaccaac aggcgcgcgc | 1200 |
| tggtgcgcat gcatcatgtg catgccatcg tccgtccctt ggcgtgcctc ggtagacggt | 1260 |
| agctagagta gtagcctgtg cttgctaccc ctggtcaaca catcgtagcc tcctatattt | 1320 |
| aacgtatcct cacacatcac aagaacgaca cacagaaacc agtagccact actccatcca | 1380 |
| ccacgagcga gcgagcgata accctagcta gcttcaggat ccagcgagag ccc | 1433 |

<210> SEQ ID NO 10

```
<211> LENGTH: 820
<212> TYPE: DNA
<213> ORGANISM: Zea mays
<220> FEATURE:
<221> NAME/KEY: promoter
<222> LOCATION: (1)...(820)
<223> OTHER INFORMATION: F3.7 promoter

<400> SEQUENCE: 10
gagctcaagc cgcaacaaca aatttcggtg ctcccaagct tcataaaggc tatcttcggc      60
gtcgttggga tccatggtgg cacagaatcg agttgatgtt gtagctggcg gctagggttt     120
gaagtggaga agaggtccgg ctggtggcat cctatcgtct attgagggtt gggtccggtg     180
gcatcatact tgatgacaat tgaaagtaat tttaatcaac ttgtcatgag tagtgagtct     240
tttataaaaa ataagctgaa ataagcaccc tttgatgagc ttataggatt atcataatct     300
caaatgctaa attatataat tttattagat aagttgcttg tttgtttccc cactagctta     360
tttacattgg attatataat ctacataaat tataatctca aacaaaaagt ccttaatcag     420
agatcagcga ggtctcacga gtgagaaggc gagagcttgt ccaaacgagc attttcgggc     480
gtgtgaacac ccatttcagc aaagccgtcg ttgtccagtt cagcgaagcg cattctgcgg     540
ctttggcgtg acccattctg ctagctcagc actgagaata cgcgtccgct gcagcgttgg     600
cgtacaggcc ggactacatt agccaacgcg tatcggcagt ggcaaacctc ttcgcttcta     660
actccgctgg gccaccagct ttgaccgccg cctcccttcc cctccgctac tgctcctccc     720
caccccactc ccccgcagga gcggcggcgg cggcggcgag gtcgtacccc acatcggcga     780
gcggcggcgg caccgccgga ggcaaaggca agtctagaac                            820

<210> SEQ ID NO 11
<211> LENGTH: 26
<212> TYPE: DNA
<213> ORGANISM: Zea mays

<400> SEQUENCE: 11
gtcagtggtg taaaagcact tctggt                                           26

<210> SEQ ID NO 12
<211> LENGTH: 26
<212> TYPE: DNA
<213> ORGANISM: Zea mays

<400> SEQUENCE: 12
tgcgccagaa gaagcagcag gaagat                                           26

<210> SEQ ID NO 13
<211> LENGTH: 26
<212> TYPE: DNA
<213> ORGANISM: Zea mays

<400> SEQUENCE: 13
aagcttaggg tacctcaaac cggtca                                           26

<210> SEQ ID NO 14
<211> LENGTH: 34
<212> TYPE: DNA
<213> ORGANISM: Zea mays

<400> SEQUENCE: 14
ccatggtcga tatctttgca gggtagggat ctct                                  34
```

```
<210> SEQ ID NO 15
<211> LENGTH: 22
<212> TYPE: DNA
<213> ORGANISM: Artificial Sequence
<220> FEATURE:
<223> OTHER INFORMATION: Clontech AP1 primer

<400> SEQUENCE: 15
gtaatacgac tcactatagg gc                                          22

<210> SEQ ID NO 16
<211> LENGTH: 19
<212> TYPE: DNA
<213> ORGANISM: Artificial Sequence
<220> FEATURE:
<223> OTHER INFORMATION: Clontech AP2 primer

<400> SEQUENCE: 16
actatagggc acgcgtggt                                              19

<210> SEQ ID NO 17
<211> LENGTH: 1679
<212> TYPE: DNA
<213> ORGANISM: Zea mays
<220> FEATURE:
<221> NAME/KEY: promoter
<222> LOCATION: (1)...(1679)
<223> OTHER INFORMATION: tb1 promoter

<400> SEQUENCE: 17
gcggccgcct acctaataga tatgtatcac tctctcctca cttcggctat aaaagagagg      60
gatagagaaa catagaatgg gtttcgaaaa aaactctttg actctctaaa tagaaacaag     120
aggaaaggga agttagttgg tcattatctt tgttgatgcc tcaacatgta attttcttcg     180
ccattgtatt tctcaatcca ctatatacaa agaggttata gggtatatat tacacatctt     240
acggtccgaa cctatattta aattacccat gtattgatgc ctaggcggta tccagcaaca     300
gagtgtctct agcacgcatc tcttactcta tttatcaact ctcccccgaa tacatgtggt     360
tccttattgt cactggcgga tctacagggt gtcaccctgt agtccggtac cggcataaca     420
tattagcttt gtctatttca tgacttcaaa catgttgcaa caacctacag atgcgttcag     480
tctatctata tacaagagga agaatacaag tgacaaatct aatttgtgaa tataagaatt     540
attatgctgg tttacataga ataccaaatt atagcacaca tttatcattc cttattgaat     600
ttctaaatgt atttcactga attattcatg catttttaat ttggcatacc ttatagtaaa     660
attctataac cgctactgct tattgtcatt atgcgacttg aagacatttt tctacctact     720
gaaagcggtc tgttttttgt gttgtcgaga gtgtgatggg taaccatagt taataatgca     780
ctggatctat cactactcat acaggtccca tatgcctaat aatgttgtga agaccaactc     840
atctgaccac atctgtccct accatgcttg tacaccacac tacatacatc actcatcact     900
ggtccttcgt ttcggtaccc tcctcccaca atgttcaatg tatatactaa tagttctcaa     960
ataaattcct gtggatgtta caaaaaccca cggtctttgg tttcctgaag aagtatttca    1020
tggaggcgcg cacgtccatc gtactgcgtc ctgcagctat ggccgccccc atctggccaa    1080
taaatgtact aggtcacttg tagccaatag cgtttcaaca tgcacacagc ttttccccca    1140
atagtgcagg tccttgtatt ctcctccctc tccctcacct caaatctcat ccacacgaac    1200
aggcggcacg gcagtattcc tccacagccc tcctctctat aagatggcac agccctctca    1260
ggtaggggcg agtgtctcac tctcacatag taaaaaaaaa aaaacgcccc caaggttct     1320
```

-continued

| | |
|---|---|
| taagcacaat tctctagcta tcttggtctc ctacacagcc tatgcacatg agcccatgcc | 1380 |
| tctcctctcc ttgcgcctgc atagagaggt ggtatgatca cctggaaagt ttttaactct | 1440 |
| ctctctctct ctctctctct ctctctctta caagcctaga ccttatgcat ggtcggacgg | 1500 |
| acacatctga tcataggaca tatgagtagg ccacactcct cctgcccctc tctcgtagag | 1560 |
| atcaacacac actgctctta gtgccaggac ctagagaggg gagcgtggag agggcatcag | 1620 |
| ggggccttgg agtcccatca gtaaagcaca tgtttccttt ctgtgattcc tcaagcccc | 1679 |

<210> SEQ ID NO 18
<211> LENGTH: 1027
<212> TYPE: DNA
<213> ORGANISM: Zea mays
<220> FEATURE:
<221> NAME/KEY: promoter
<222> LOCATION: (1)...(1027)
<223> OTHER INFORMATION: eep2 promoter

<400> SEQUENCE: 18

| | |
|---|---|
| gtaaagttac aattatatat caaatgctag ctactagtcg ggagaaaacc aactaagggg | 60 |
| atgtttgttt gggattgtaa tctgtccaga atatataatc caacaaattt tgaactaaca | 120 |
| ctcggttcaa aatttattag attatataat ccatacatat tacaatccca aacaaacacc | 180 |
| cctaattcta aatggtgaga gtaaaaagcg ctgtctaata acttttatca gctaatttgt | 240 |
| ttatcttgag ctgttaatta aaccattagt gaagtttttt tgggggggtgg tcgaatagag | 300 |
| ctaatctaac tattagctca taggatcaag gccattggtt taatttcacc ccactatgac | 360 |
| tatgtcccag taactaaata ctatatttgt caccataaac tttggaagaa attagttgct | 420 |
| actagaaaga agatccaaac ctggaaaaaa ttagtttcta ctagaaagca gatcatgtct | 480 |
| gctacccaga cattgattta tactccagca tcaaccaacc ccgtacttgt tactacaaaa | 540 |
| ttggaagaaa ttagttgcta ctagaaagta gataatttct gccaccagat attgatttat | 600 |
| aacctagtat caatctctac tagccttgct tccgtcattt gttgctagat ataaatggtt | 660 |
| ttctttcaca tatgtgagtg tatatatatg aaccttgcag caaccattat attcggtagt | 720 |
| caaacaaagc cctacagaca tcgatctctg atctgagaaa aaaaatcctt atatggcgag | 780 |
| aattacaatg gaagcaagca aggctgtcct gctcttgatg gtgatcctag gaagtttgat | 840 |
| gattcccgca tactgtaagt gcacatcggg caaccatgcg catttgaatc aagttacata | 900 |
| ttatacagtt tcttactagt agtaaatata aattgttcgc ataatgtcaa caaccttaac | 960 |
| ttactgtaaa aacagtaact gaatgccctt attgcatgca gctcggaacc ttgttcgttt | 1020 |
| tctgccc | 1027 |

<210> SEQ ID NO 19
<211> LENGTH: 723
<212> TYPE: DNA
<213> ORGANISM: Zea mays
<220> FEATURE:
<221> NAME/KEY: promoter
<222> LOCATION: (1)...(723)
<223> OTHER INFORMATION: trx1 or thxH promoter (thioredoxin H)

<400> SEQUENCE: 19

| | |
|---|---|
| gcccttacta tagggcacgc gtggtcgacg gcccgggctg gtactctctg gtactgagtt | 60 |
| agatttggtg aatgttaata catatatact tttaataaaa ttactttta agacaaaatt | 120 |
| gatgcactgg cgttcattgg cggctgtgtt aacaaaaccg aagtggaagt agcccgttcc | 180 |
| actggaggtt ggcttaagtg cacatgcagt gaaaataacg ttccacttgc gattcattta | 240 |

```
acacaactgt cagtataaat agttttttt  attggcggtt gatttaggtg aaccccaagc      300
gaaaatatat ttacacatgc ggttttttaa gccgtgctca cctatttatt ttcagtgtgc      360
ttaactgaaa ctgtcggtat aaattttgc  gtgccatcag tttagagcac ttatctactg     420 acttttttt  tcaagtatcg tacggatttt gcaccacgtc gacgaccgtc gataacgagg     480
cacgccgatc tagagagctc gaagacctgg gaatggcaca gggaccggc  cggagccgc      540 cggcgccatg caagctgcct cgatcgcggg cctcgaccta agtagcccgt ccctgtcgcg     600
cgccagtcgc tcgctgcgcc tataaaagcc gcccgcggct cgcgtaggct accagcgcaa     660
aactctgcca agggcttcgg atcccacacc gaggaaagga gaagagaggg tcggaatacc     720
atg                                                                   723
```

```
<210> SEQ ID NO 20
<211> LENGTH: 1626
<212> TYPE: DNA
<213> ORGANISM: Zea mays
<220> FEATURE:
<221> NAME/KEY: promoter
<222> LOCATION: (1)...(1626)
<223> OTHER INFORMATION: Zm40 or Mze40-2 promoter

<400> SEQUENCE: 20
```

```
aagcttagct agatcatttg taagaatgca acttgttcat atagcatggc tacagcctac      60
atcatctgaa atagacctgt ttataggata cctaagctca attcacccta tatctaaaac     120
ctacgaggcc taaacacacc cgtcctcaag aaaacgacca aaccaaacca aaccatgcgt     180
ccgtgtcatg gttttgtaga cacgtttacg tatcaattat agtgttctga ttttttatat     240
tctcctaatt atttagagct aaatttattt ttatgatagc agagatctaa atattttgt      300 tttgatttt  tatatactaa aatcatctct acaatattag agattttaaa tgctcagaag     360
aattttactt gaattaaaac ctttactgat ttttaactaa aacggagacc aaaagaaatc     420
tatccaaggc tgcctctaag agccttcgtg tctcgttttc ttatttcaga cttcactcat     480
cttcttattt caggctccac tatataaggt ggtctctagt atctttccta tcacatatcc     540
tatttaaaac tttagtatat aaaacattat aattcataat ataaatcgat tattttacac     600
gatctcagcc taaagcggt  aatatgcacg ctctgagcat ggcccaagct ccacgttaac     660
cgttctgtca aaaaaaaaaa catctagtct agaatggaaa acacacgatt ttagaagtta     720
ggactagttt ggcaactcaa ttttccaaat gattctcatt cttttaagag gatttaattt     780
attttttggt aaaataggaa tcactagaaa ctctattttt tcaagagaaa gtaagctatt     840
tttttagaaa aataaaaaat cccttaaaaa atattgttcg taaattagcc ctaagatgga     900
ctaaaaatct ggttttatag aatagggagg gatcgagcaa ccgccaaatc tacgcgccaa     960
aaaggtacct tttccgtgaa taaacacgac tgcggcgatc acgatctgat cgaactcgta    1020
gaataaaatg gagcagcgga atagtgtggg aggcacaagc acaggaggag ctgaaaccga    1080
accgaagtgg cgaacacgat cccactccg  gccggcaccc gagtgtgcga gacgtgtggg    1140
gctgatctga cgagcctgga agaagaagaa gaaaaaaaag tcctcacgct cctgcttggc    1200
tccatcgaca gctcactagc tgctaccgga tgctcgcgtc tctgatgcct ctcgattcat    1260
catccatcgt tggtggcggc ggcggggcgg caaaggttct gattccgcag cagccaagtg    1320
ctcctcctgc agacgaaaat gacggcagag gttggcgttg atccaggaga ctcatcagtt    1380
tagtttaata atgaatctgt agcaggcgct tcagtctctc atcggatgag cgagcagctt    1440
```

```
agcagagcag gtggtggtcc ctggctcgcc cccgtccatt ctttcccgcc cgtcctgccg    1500
tccactccgc cgcctatttta taccccctcct cgcccaccct gccatcctca ccatcgcaat    1560
tcacaagcaa agcaatcaga gccaagcacc caccgtcctc ctttctttcc ttcgactcat    1620
caaagc                                                               1626

<210> SEQ ID NO 21
<211> LENGTH: 27
<212> TYPE: DNA
<213> ORGANISM: Zea mays

<400> SEQUENCE: 21
aaacaccttc ggatattgct ccctttt                                           27

<210> SEQ ID NO 22
<211> LENGTH: 27
<212> TYPE: DNA
<213> ORGANISM: Zea mays

<400> SEQUENCE: 22
tctcgcattt gcagaaacga acaacgt                                           27

<210> SEQ ID NO 23
<211> LENGTH: 525
<212> TYPE: DNA
<213> ORGANISM: Zea mays
<220> FEATURE:
<221> NAME/KEY: promoter
<222> LOCATION: (1)...(525)
<223> OTHER INFORMATION: mLIP15

<400> SEQUENCE: 23
ctttcagcta agtccctgct ccctctcttt ttcttacatt caggtcctcg cagctcctct      60
cttttttctt gtttctttct ttcgatctgc gagccgtcca ggtccagtac tctcctttcc    120
gtgaaggaac tcttgcagcc ggcccctctg gtttcctcga attcttgttc cccggtccct    180
cctcctgtcc ccgcgtagat ccgtccgtcc gaggagcaca ccgtccccac ccccatgttt    240
acccaccagt tcctctgacg gccgccgtgc tccgatgaag ctgagcgtgc tccgtatccg    300
ccgctcccac tccttctccg tgccttcct ctactggttc tacgtcttct catgaacgca     360
tcgcccctct ccacctgctg atccttcgcc atctctccat ctctctttct ctctgagata    420
gtctttcgaa tccatctcta gggctcttgt ttctccccat cctccccca ccccaccccc     480 caccaaacac aagtcccctt gttcaatccg acaagacaag catcc                    525

<210> SEQ ID NO 24
<211> LENGTH: 587
<212> TYPE: DNA
<213> ORGANISM: Zea mays
<220> FEATURE:
<221> NAME/KEY: promoter
<222> LOCATION: (1)...(587)
<223> OTHER INFORMATION: ESR promoter

<400> SEQUENCE: 24
gaattcgccc ttggtagatg tctagatgac ctattctact tttcctaaga ttttctctgt      60
atgagtaacc tgtcataatt taacttgtga gatcttgccg atataaaaaa aaaacgccag    120
tcatttatgg tacgggatta ataggttcca agaaccagcc acaatccatt tattagtttc    180
atataaatgt cataaatttt tactaaaatt ttctctgtat agtaacatgt cataactgaa    240
cttgtgagaa aaacgccagt tatttatggt acgggattaa taggttccaa aaaccagccg    300
```

```
taacctattt atattagggt actttaagct ggtgccctca gttttgttgg tgtcttcgtt      360
tttaaactta gttgtatttt ttttcttagt tctgtccttc tagtgttata gagcataagg      420
acaaaattga gcaaaaaatg actaaggata aaaatgagga tatcagaaag ggcagcagct      480
taaaaaacct tttatattag ttcaaaagga caccagtcta taaaaagtat actccaagca      540
catttgaatt tggatttgca ttgtcagtca ggccagtcaa ggggacc                    587

<210> SEQ ID NO 25
<211> LENGTH: 900
<212> TYPE: DNA
<213> ORGANISM: Zea mays
<220> FEATURE:
<221> NAME/KEY: promoter
<222> LOCATION: (1)...(900)
<223> OTHER INFORMATION: PCNA2 promoter

<400> SEQUENCE: 25
atcgtaatcg gttttcaccg tataccgaac cgaaaaaacc gaataccaaa ctttatcaat       60
tcccaaattt gactattcga ttatgtgaac taattgtgtg atacaattaa attgttattc      120
acttatttgt atgtgatgta tgatgtatat ctaaatattt gtacctatat aatttttact      180
ttttaaaatt atatgtaatc tatcatgtaa acttgttgta tgtattgtct tgattataag      240
tttggtattc ggtttttacc gaaaaatcga agtaaaaaac cgaaaccgaa cttctcggtt      300
tttcattttc tagaaaaccg aacggtttct aatgtttgaa aaaccgaagt tttttaaaac      360
cgaaaaaccg aaccgaagtt tagaaaaaaa ccgaatgccc agccctaaaa attagtaccc      420
cataagaact aaaaaaagat aaaatgacta aaaattaatc agttgaaacc aaacctattt      480
tcccccacac ctcacggtat tgtttcgcat tccaagtttg aaacacgact ggaaacaaaa      540
cccaaaacga ctggagggac cgagcttgtg ctgagcagca gagatggcgg gaaatgctgc      600
gtctcccgcc tcagtttcgg atgccccgcc ctttcccaaa ccggccaccg ccgccgcccg      660
tgtctcccca ccgacaggtg ggtccaatcc ttaaccacgg accagggccc ccacctgtca      720
ggtggaccct tccgaagcaag gatcggccag gcgggaaaac atttcgcggc aggtggcggt      780
tgcgccaaat ttctccctcc ctttttccgtt cggcgtcccc aaacgcctcc ctattaatct      840
ccccgcgttc cccttccctc gcgccgccgc tctcccctcc caaagctcgc cccgctccca      900

<210> SEQ ID NO 26
<211> LENGTH: 1560
<212> TYPE: DNA
<213> ORGANISM: Zea mays
<220> FEATURE:
<221> NAME/KEY: CDS
<222> LOCATION: (1)...(1560)

<400> SEQUENCE: 26 atg aag ccg cca tca ctg gtg cac tgc ttc aag ctg ctg gtc ctg ctg       48
Met Lys Pro Pro Ser Leu Val His Cys Phe Lys Leu Leu Val Leu Leu
 1               5                  10                  15 gcg ctc gcc agg ctg acc atg cac gtc ccc gac gag gac atg cta tcg       96
Ala Leu Ala Arg Leu Thr Met His Val Pro Asp Glu Asp Met Leu Ser
            20                  25                  30 ccc ctc ggc gcg ctg cgc ctc gac ggt cat ttc agc ttc cat gac gtc      144
Pro Leu Gly Ala Leu Arg Leu Asp Gly His Phe Ser Phe His Asp Val
        35                  40                  45 tcc gcc atg gcg cgg gac ttc ggc aac cag tgc agc ttc ctg ccg gcc      192
Ser Ala Met Ala Arg Asp Phe Gly Asn Gln Cys Ser Phe Leu Pro Ala
    50                  55                  60
```

| | | |
|---|---|---|
| gcc gtg ctc cac cca ggc tcg gtc tcc gat atc gcc gcc acc gtg agg<br>Ala Val Leu His Pro Gly Ser Val Ser Asp Ile Ala Ala Thr Val Arg<br>65                                   70                               75                            80 | 240 |
| cac gtc ttc tcc ctg ggc gag ggc tcg ccg ctc acc gtc gcg gcg cgc<br>His Val Phe Ser Leu Gly Glu Gly Ser Pro Leu Thr Val Ala Ala Arg<br>                            85                               90                              95 | 288 |
| ggg cat gga cac tcc ctc atg ggt cag tcc cag gcc gcc cag ggg atc<br>Gly His Gly His Ser Leu Met Gly Gln Ser Gln Ala Ala Gln Gly Ile<br>                   100                            105                            110 | 336 |
| gtg gtc agg atg gag tcg ctc cgg ggc gct agg ctc cag gtc cac gac<br>Val Val Arg Met Glu Ser Leu Arg Gly Ala Arg Leu Gln Val His Asp<br>         115                             120                            125 | 384 |
| ggc ttt gtc gat gcc ccc gga gga gag ctc tgg atc aat gtc ctg cgt<br>Gly Phe Val Asp Ala Pro Gly Gly Glu Leu Trp Ile Asn Val Leu Arg<br>130                                 135                             140 | 432 |
| gag acg ctg aag cac ggc ctg gca ccc aag tcg tgg acg gac tat ctc<br>Glu Thr Leu Lys His Gly Leu Ala Pro Lys Ser Trp Thr Asp Tyr Leu<br>145                              150                           155                      160 | 480 |
| cat ctc acg gtc ggt ggc acc ttg tct aat gcg ggg gtc agc ggc cag<br>His Leu Thr Val Gly Gly Thr Leu Ser Asn Ala Gly Val Ser Gly Gln<br>                   165                            170                            175 | 528 |
| gcg ttc cgc cac gga ccg cag gtc agc aat gtc aat caa ctg gag att<br>Ala Phe Arg His Gly Pro Gln Val Ser Asn Val Asn Gln Leu Glu Ile<br>                            180                              185                            190 | 576 |
| gtg aca gga agg gga gac gtc gtt acc tgc tca ccc gag gat aac tct<br>Val Thr Gly Arg Gly Asp Val Val Thr Cys Ser Pro Glu Asp Asn Ser<br>         195                             200                            205 | 624 |
| gat ctc ttc tat gct gct ctc ggc ggt ctt ggt cag ttc ggg atc ata<br>Asp Leu Phe Tyr Ala Ala Leu Gly Gly Leu Gly Gln Phe Gly Ile Ile<br>210                               215                             220 | 672 |
| acc aga gca agg att gca ctt gag cct gct cca gag atg gtg agg tgg<br>Thr Arg Ala Arg Ile Ala Leu Glu Pro Ala Pro Glu Met Val Arg Trp<br>225                              230                           235                      240 | 720 |
| ata aga gtt ctt tac tcg gat ttt gaa agc ttc acc gaa gac cag gag<br>Ile Arg Val Leu Tyr Ser Asp Phe Glu Ser Phe Thr Glu Asp Gln Glu<br>                            245                              250                            255 | 768 |
| atg ttg atc atg gca gag aac tcc ttt gac tac att gaa ggt ttt gtc<br>Met Leu Ile Met Ala Glu Asn Ser Phe Asp Tyr Ile Glu Gly Phe Val<br>                            260                              265                            270 | 816 |
| atc ata aac agg aca ggc atc ctc aac aac tgg agg gcg tcc ttc aag<br>Ile Ile Asn Arg Thr Gly Ile Leu Asn Asn Trp Arg Ala Ser Phe Lys<br>         275                             280                            285 | 864 |
| cca cag gac cca gtc caa gca agc cat ttc cag tca gat gga aga gtg<br>Pro Gln Asp Pro Val Gln Ala Ser His Phe Gln Ser Asp Gly Arg Val<br>290                               295                           300 | 912 |
| cta tac tgc ctc gaa cta acc aag aac ttc aat agt ggc gac act gat<br>Leu Tyr Cys Leu Glu Leu Thr Lys Asn Phe Asn Ser Gly Asp Thr Asp<br>305                               310                           315                      320 | 960 |
| acc atg gaa cag gaa gtt gct gta ctg cta tct cgg ctt aga ttc ata<br>Thr Met Glu Gln Glu Val Ala Val Leu Leu Ser Arg Leu Arg Phe Ile<br>                            325                              330                            335 | 1008 |
| cag tct act cta ttc cac acc gat gtc acg tac ctg gag ttt tgt gac<br>Gln Ser Thr Leu Phe His Thr Asp Val Thr Tyr Leu Glu Phe Leu Asp<br>                   340                            345                            350 | 1056 |
| agg gtg cac acc tct gag ctg aag ctg agg gca caa agc ctc tgg gaa<br>Arg Val His Thr Ser Glu Leu Lys Leu Arg Ala Gln Ser Leu Trp Glu<br>         355                             360                            365 | 1104 |
| gtt cca cac cct tgg ttg aat ctt ctg ata ccg agg agc tca atc cgc<br>Val Pro His Pro Trp Leu Asn Leu Leu Ile Pro Arg Ser Ser Ile Arg | 1152 |

```
                370             375             380
aga ttt gct acg gaa gtc ttt ggc agg atc ctg aaa gat agc aac aat       1200
Arg Phe Ala Thr Glu Val Phe Gly Arg Ile Leu Lys Asp Ser Asn Asn
385                 390                 395                 400 ggt cct ata ttg ctt tat cca gtg aac aaa tca aag tgg gac aac aaa       1248
Gly Pro Ile Leu Leu Tyr Pro Val Asn Lys Ser Lys Trp Asp Asn Lys
                405                 410                 415 acg tca gtg gtc ata cca gat gag gaa att ttc tac cta gtg gga ttc       1296
Thr Ser Val Val Ile Pro Asp Glu Glu Ile Phe Tyr Leu Val Gly Phe
        420                 425                 430 ctt tct tca gca ccg tct ctc tca ggt cac ggc agc att gca cat gcg       1344
Leu Ser Ser Ala Pro Ser Leu Ser Gly His Gly Ser Ile Ala His Ala
            435                 440                 445 atg agc ctg aac agc caa ata gta gag ttc tgt gaa gag gct gat att       1392
Met Ser Leu Asn Ser Gln Ile Val Glu Phe Cys Glu Glu Ala Asp Ile
    450                 455                 460 ggg atg aaa cag tat cta gca cac tac acc aca cag gag cag tgg aaa       1440
Gly Met Lys Gln Tyr Leu Ala His Tyr Thr Thr Gln Glu Gln Trp Lys
465                 470                 475                 480 acc cac ttt gga gca agg tgg gag aca ttt gaa cgg agg aaa cac aga       1488
Thr His Phe Gly Ala Arg Trp Glu Thr Phe Glu Arg Arg Lys His Arg
                485                 490                 495 tat gat ccc cta gcc atc cta gca cca gga cag aga ata ttc cca aag       1536
Tyr Asp Pro Leu Ala Ile Leu Ala Pro Gly Gln Arg Ile Phe Pro Lys
        500                 505                 510 gcg tca ctc cca ttg tct ttg tga                                       1560
Ala Ser Leu Pro Leu Ser Leu *
            515

<210> SEQ ID NO 27
<211> LENGTH: 519
<212> TYPE: PRT
<213> ORGANISM: Zea mays

<400> SEQUENCE: 27

Met Lys Pro Pro Ser Leu Val His Cys Phe Lys Leu Val Leu Leu
 1               5                  10                  15

Ala Leu Ala Arg Leu Thr Met His Val Pro Asp Glu Asp Met Leu Ser
                20                  25                  30

Pro Leu Gly Ala Leu Arg Leu Asp Gly His Phe Ser Phe His Asp Val
            35                  40                  45

Ser Ala Met Ala Arg Asp Phe Gly Asn Gln Cys Ser Phe Leu Pro Ala
        50                  55                  60

Ala Val Leu His Pro Gly Ser Val Ser Asp Ile Ala Ala Thr Val Arg
65                  70                  75                  80

His Val Phe Ser Leu Gly Glu Gly Ser Pro Leu Thr Val Ala Ala Arg
                85                  90                  95

Gly His Gly His Ser Leu Met Gly Gln Ser Gln Ala Ala Gln Gly Ile
            100                 105                 110

Val Val Arg Met Glu Ser Leu Arg Gly Ala Arg Leu Gln Val His Asp
        115                 120                 125

Gly Phe Val Asp Ala Pro Gly Gly Glu Leu Trp Ile Asn Val Leu Arg
    130                 135                 140

Glu Thr Leu Lys His Gly Leu Ala Pro Lys Ser Trp Thr Asp Tyr Leu
145                 150                 155                 160

His Leu Thr Val Gly Gly Thr Leu Ser Asn Ala Gly Val Ser Gly Gln
                165                 170                 175
```

```
Ala Phe Arg His Gly Pro Gln Val Ser Asn Val Asn Gln Leu Glu Ile
            180                 185                 190

Val Thr Gly Arg Gly Asp Val Val Thr Cys Ser Pro Glu Asp Asn Ser
        195                 200                 205

Asp Leu Phe Tyr Ala Ala Leu Gly Gly Leu Gly Gln Phe Gly Ile Ile
    210                 215                 220

Thr Arg Ala Arg Ile Ala Leu Glu Pro Ala Pro Glu Met Val Arg Trp
225                 230                 235                 240

Ile Arg Val Leu Tyr Ser Asp Phe Glu Ser Phe Thr Glu Asp Gln Glu
                245                 250                 255

Met Leu Ile Met Ala Glu Asn Ser Phe Asp Tyr Ile Glu Gly Phe Val
            260                 265                 270

Ile Ile Asn Arg Thr Gly Ile Leu Asn Asn Trp Arg Ala Ser Phe Lys
        275                 280                 285

Pro Gln Asp Pro Val Gln Ala Ser His Phe Gln Ser Asp Gly Arg Val
    290                 295                 300

Leu Tyr Cys Leu Glu Leu Thr Lys Asn Phe Asn Ser Gly Asp Thr Asp
305                 310                 315                 320

Thr Met Glu Gln Glu Val Ala Val Leu Leu Ser Arg Leu Arg Phe Ile
                325                 330                 335

Gln Ser Thr Leu Phe His Thr Asp Val Thr Tyr Leu Glu Phe Leu Asp
            340                 345                 350

Arg Val His Thr Ser Glu Leu Lys Leu Arg Ala Gln Ser Leu Trp Glu
        355                 360                 365

Val Pro His Pro Trp Leu Asn Leu Leu Ile Pro Arg Ser Ser Ile Arg
    370                 375                 380

Arg Phe Ala Thr Glu Val Phe Gly Arg Ile Leu Lys Asp Ser Asn Asn
385                 390                 395                 400

Gly Pro Ile Leu Leu Tyr Pro Val Asn Lys Ser Lys Trp Asp Asn Lys
                405                 410                 415

Thr Ser Val Val Ile Pro Asp Glu Glu Ile Phe Tyr Leu Val Gly Phe
            420                 425                 430

Leu Ser Ser Ala Pro Ser Leu Ser Gly His Gly Ser Ile Ala His Ala
        435                 440                 445

Met Ser Leu Asn Ser Gln Ile Val Glu Phe Cys Glu Glu Ala Asp Ile
    450                 455                 460

Gly Met Lys Gln Tyr Leu Ala His Tyr Thr Thr Gln Glu Gln Trp Lys
465                 470                 475                 480

Thr His Phe Gly Ala Arg Trp Glu Thr Phe Glu Arg Lys His Arg
                485                 490                 495

Tyr Asp Pro Leu Ala Ile Leu Ala Pro Gly Gln Arg Ile Phe Pro Lys
            500                 505                 510

Ala Ser Leu Pro Leu Ser Leu
        515

<210> SEQ ID NO 28
<211> LENGTH: 1617
<212> TYPE: DNA
<213> ORGANISM: Zea mays
<220> FEATURE:
<221> NAME/KEY: CDS
<222> LOCATION: (1)...(1617)

<400> SEQUENCE: 28 atg gca aga agg act cgt ttc gtg gcc atc gcc gcc ctc ctc aca agc    48
Met Ala Arg Arg Thr Arg Phe Val Ala Ile Ala Ala Leu Leu Thr Ser
```

```
                                        -continued
     1               5              10             15
ttc ctc aac gtc gca gcc ggg cat tcc cgg cca ctg tcc ggt gcc ggc    96
Phe Leu Asn Val Ala Ala Gly His Ser Arg Pro Leu Ser Gly Ala Gly
                 20                  25                 30 ctc ccg ggc gat ctt ttc ggg ctg ggc atc gcg tcg agg atc cgc acg   144
Leu Pro Gly Asp Leu Phe Gly Leu Gly Ile Ala Ser Arg Ile Arg Thr
             35                  40                  45 gac agc aac tcg acg gcg aag gcg gcg acg gac ttc ggc cag atg gtg   192
Asp Ser Asn Ser Thr Ala Lys Ala Ala Thr Asp Phe Gly Gln Met Val
         50                  55                  60 agg gcc gcg ccg gag gcc gtg ttc cac ccc gcc acg ccg gcc gac atc   240
Arg Ala Ala Pro Glu Ala Val Phe His Pro Ala Thr Pro Ala Asp Ile
 65                  70                  75                  80 gcc gcg ctc gtc cgg ttc tcc gcc acg tcg gcg gcg ccg ttc ccc gtt   288
Ala Ala Leu Val Arg Phe Ser Ala Thr Ser Ala Ala Pro Phe Pro Val
                 85                  90                  95 gcg ccg cgc ggg cag ggc cac tcc tgg cgc ggc cag gcg ctc gcc ccg   336
Ala Pro Arg Gly Gln Gly His Ser Trp Arg Gly Gln Ala Leu Ala Pro
            100                 105                 110 ggc ggc gtc gtc gtg gac atg ggc tcg ctg ggg cgc ggc ccc cgc atc   384
Gly Gly Val Val Val Asp Met Gly Ser Leu Gly Arg Gly Pro Arg Ile
        115                 120                 125 aac gtg tcc gcc gtg gcc ggc gcg gag ccg ttc gtc gac gcc ggc ggg   432
Asn Val Ser Ala Val Ala Gly Ala Glu Pro Phe Val Asp Ala Gly Gly
    130                 135                 140 gag cag ctg tgg gtc gac gtc ctc cgc gcc acg ctg cga cac ggc ctg   480
Glu Gln Leu Trp Val Asp Val Leu Arg Ala Thr Leu Arg His Gly Leu
145                 150                 155                 160 gcg ccc cgc gtg tgg acc gac tac ctc cgg ctc acc gtc ggc ggc acg   528
Ala Pro Arg Val Trp Thr Asp Tyr Leu Arg Leu Thr Val Gly Gly Thr
                165                 170                 175 ctc tcc aac gcg gga atc ggc ggg cag gcg ttc cga cac ggt ccg cag   576
Leu Ser Asn Ala Gly Ile Gly Gly Gln Ala Phe Arg His Gly Pro Gln
            180                 185                 190 atc gcc aac gtg cat gaa ctc gac gtc gtc aca ggc aca ggt gag atg   624
Ile Ala Asn Val His Glu Leu Asp Val Val Thr Gly Thr Gly Glu Met
        195                 200                 205 gtg aca tgc tcc atg gac gtg aac tcg gac ctg ttc atg gcg gct cta   672
Val Thr Cys Ser Met Asp Val Asn Ser Asp Leu Phe Met Ala Ala Leu
    210                 215                 220 ggc ggg tta ggc cag ttc ggg gtc ata acc aga gca cgg atc cgg ctt   720
Gly Gly Leu Gly Gln Phe Gly Val Ile Thr Arg Ala Arg Ile Arg Leu
225                 230                 235                 240 gag ccg gcg ccc aag agg gtg cgc tgg gtt cga ctt gcc tac acc gac   768
Glu Pro Ala Pro Lys Arg Val Arg Trp Val Arg Leu Ala Tyr Thr Asp
                245                 250                 255 gtc gct act ttc acc aag gat cag gag ttt ctc ata tca aac cgg gct   816
Val Ala Thr Phe Thr Lys Asp Gln Glu Phe Leu Ile Ser Asn Arg Ala
            260                 265                 270 agc caa gtc ggg ttc gac tac gtc gaa ggc cag gtc cag ctc agc cgg   864
Ser Gln Val Gly Phe Asp Tyr Val Glu Gly Gln Val Gln Leu Ser Arg
        275                 280                 285 tcc ttg gtc gaa ggc ccc aaa tca aca ccc ttc ttc tcc ggc gcc gat   912
Ser Leu Val Glu Gly Pro Lys Ser Thr Pro Phe Phe Ser Gly Ala Asp
    290                 295                 300 gtt gct agg ctt gct gga ctc gcg tcc agg acc gga cct gct gca atc   960
Val Ala Arg Leu Ala Gly Leu Ala Ser Arg Thr Gly Pro Ala Ala Ile
305                 310                 315                 320 tac tac atc gaa ggc gcc atg tac tac acc aag gac acc gcc ata tct  1008
```

```
Tyr Tyr Ile Glu Gly Ala Met Tyr Tyr Thr Lys Asp Thr Ala Ile Ser
            325                 330                 335 gtg gac aag aaa atg aag gca ctc ctg gat cag ctg agc ttc gag cca      1056
Val Asp Lys Lys Met Lys Ala Leu Leu Asp Gln Leu Ser Phe Glu Pro
            340                 345                 350 ggg ttt gcg ttc acc aag gac gtg acg ttc gtg cag ttc ctc gat cgg      1104
Gly Phe Ala Phe Thr Lys Asp Val Thr Phe Val Gln Phe Leu Asp Arg
            355                 360                 365 gtg cgc gag gag gag agg gtg ctc cgg tca gcc ggc gcg tgg gag gtg      1152
Val Arg Glu Glu Glu Arg Val Leu Arg Ser Ala Gly Ala Trp Glu Val
        370                 375                 380 ccg cac cca tgg ctg aac ctc ttc gtc cca cgg tcg cgc atc ctc gac      1200
Pro His Pro Trp Leu Asn Leu Phe Val Pro Arg Ser Arg Ile Leu Asp
385                 390                 395                 400 ttc gac gac gga gtg ttc aag gct ctc ctc aag gac tcc aac cca gct      1248
Phe Asp Asp Gly Val Phe Lys Ala Leu Leu Lys Asp Ser Asn Pro Ala
                405                 410                 415 ggg atc atc ctc atg tac ccc atg aac aag gat agg tgg gac gac cgg      1296
Gly Ile Ile Leu Met Tyr Pro Met Asn Lys Asp Arg Trp Asp Asp Arg
            420                 425                 430 atg aca gcg atg acc cca gcc acg gac gac gac gac atg ttc tat gcc      1344
Met Thr Ala Met Thr Pro Ala Thr Asp Asp Asp Asp Met Phe Tyr Ala
            435                 440                 445 gtt agt ttc ctt tgg tca gca ctg tcc gca gac gac gtg ccc cag ctc      1392
Val Ser Phe Leu Trp Ser Ala Leu Ser Ala Asp Asp Val Pro Gln Leu
        450                 455                 460 gag aga tgg aac aag gca gtg ctg gac ttc tgt gat cgg tca gga ata      1440
Glu Arg Trp Asn Lys Ala Val Leu Asp Phe Cys Asp Arg Ser Gly Ile
465                 470                 475                 480 gaa tgc aag cag tac ctg cca cac tac aca tct caa gac ggg tgg cga      1488
Glu Cys Lys Gln Tyr Leu Pro His Tyr Thr Ser Gln Asp Gly Trp Arg
                485                 490                 495 cgg cat ttc ggg gcg aaa tgg agc agg atc gct gag ctg aag gcc aga      1536
Arg His Phe Gly Ala Lys Trp Ser Arg Ile Ala Glu Leu Lys Ala Arg
            500                 505                 510 tat gac cct cgg gca ttg ttg tcg ccg ggc cag agg att ttt ccg gtg      1584
Tyr Asp Pro Arg Ala Leu Leu Ser Pro Gly Gln Arg Ile Phe Pro Val
            515                 520                 525 cca gta gag gca tct ggc att gct tct gcc tga                          1617
Pro Val Glu Ala Ser Gly Ile Ala Ser Ala *
            530                 535

<210> SEQ ID NO 29
<211> LENGTH: 538
<212> TYPE: PRT
<213> ORGANISM: Zea mays

<400> SEQUENCE: 29

Met Ala Arg Arg Thr Arg Phe Val Ala Ile Ala Ala Leu Leu Thr Ser
1               5                   10                  15

Phe Leu Asn Val Ala Ala Gly His Ser Arg Pro Leu Ser Gly Ala Gly
            20                  25                  30

Leu Pro Gly Asp Leu Phe Gly Leu Gly Ile Ala Ser Arg Ile Arg Thr
        35                  40                  45

Asp Ser Asn Ser Thr Ala Lys Ala Ala Thr Asp Phe Gly Gln Met Val
    50                  55                  60

Arg Ala Ala Pro Glu Ala Val Phe His Pro Ala Thr Pro Ala Asp Ile
65                  70                  75                  80

Ala Ala Leu Val Arg Phe Ser Ala Thr Ser Ala Ala Pro Phe Pro Val
```

-continued

```
                85                  90                  95
Ala Pro Arg Gly Gln Gly His Ser Trp Arg Gly Gln Ala Leu Ala Pro
            100                 105                 110
Gly Gly Val Val Val Asp Met Gly Ser Leu Gly Arg Gly Pro Arg Ile
            115                 120                 125
Asn Val Ser Ala Val Ala Gly Ala Glu Pro Phe Val Asp Ala Gly Gly
            130                 135                 140
Glu Gln Leu Trp Val Asp Val Leu Arg Ala Thr Leu Arg His Gly Leu
145                 150                 155                 160
Ala Pro Arg Val Trp Thr Asp Tyr Leu Arg Leu Thr Val Gly Gly Thr
            165                 170                 175
Leu Ser Asn Ala Gly Ile Gly Gly Gln Ala Phe Arg His Gly Pro Gln
            180                 185                 190
Ile Ala Asn Val His Glu Leu Asp Val Val Thr Gly Thr Gly Glu Met
            195                 200                 205
Val Thr Cys Ser Met Asp Val Asn Ser Asp Leu Phe Met Ala Ala Leu
            210                 215                 220
Gly Gly Leu Gly Gln Phe Gly Val Ile Thr Arg Ala Arg Ile Arg Leu
225                 230                 235                 240
Glu Pro Ala Pro Lys Arg Val Arg Trp Val Arg Leu Ala Tyr Thr Asp
            245                 250                 255
Val Ala Thr Phe Thr Lys Asp Gln Glu Phe Leu Ile Ser Asn Arg Ala
            260                 265                 270
Ser Gln Val Gly Phe Asp Tyr Val Glu Gly Gln Val Gln Leu Ser Arg
            275                 280                 285
Ser Leu Val Glu Gly Pro Lys Ser Thr Pro Phe Phe Ser Gly Ala Asp
            290                 295                 300
Val Ala Arg Leu Ala Gly Leu Ala Ser Arg Thr Gly Pro Ala Ala Ile
305                 310                 315                 320
Tyr Tyr Ile Glu Gly Ala Met Tyr Tyr Thr Lys Asp Thr Ala Ile Ser
            325                 330                 335
Val Asp Lys Lys Met Lys Ala Leu Leu Asp Gln Leu Ser Phe Glu Pro
            340                 345                 350
Gly Phe Ala Phe Thr Lys Asp Val Thr Phe Val Gln Phe Leu Asp Arg
            355                 360                 365
Val Arg Glu Glu Arg Val Leu Arg Ser Ala Gly Ala Trp Glu Val
            370                 375                 380
Pro His Pro Trp Leu Asn Leu Phe Val Pro Arg Ser Arg Ile Leu Asp
385                 390                 395                 400
Phe Asp Asp Gly Val Phe Lys Ala Leu Leu Lys Asp Ser Asn Pro Ala
            405                 410                 415
Gly Ile Ile Leu Met Tyr Pro Met Asn Lys Asp Arg Trp Asp Asp Arg
            420                 425                 430
Met Thr Ala Met Thr Pro Ala Thr Asp Asp Asp Met Phe Tyr Ala
            435                 440                 445
Val Ser Phe Leu Trp Ser Ala Leu Ser Ala Asp Val Pro Gln Leu
            450                 455                 460
Glu Arg Trp Asn Lys Ala Val Leu Asp Phe Cys Asp Arg Ser Gly Ile
465                 470                 475                 480
Glu Cys Lys Gln Tyr Leu Pro His Tyr Thr Ser Gln Asp Gly Trp Arg
            485                 490                 495
Arg His Phe Gly Ala Lys Trp Ser Arg Ile Ala Glu Leu Lys Ala Arg
            500                 505                 510
```

```
Tyr Asp Pro Arg Ala Leu Leu Ser Pro Gly Gln Arg Ile Phe Pro Val
            515                 520                 525

Pro Val Glu Ala Ser Gly Ile Ala Ser Ala
        530                 535

<210> SEQ ID NO 30
<211> LENGTH: 1566
<212> TYPE: DNA
<213> ORGANISM: Zea mays
<220> FEATURE:
<221> NAME/KEY: CDS
<222> LOCATION: (1)...(1566)

<400> SEQUENCE: 30 atg atg ctc gcg tac atg gac cgc gcg acg gcg gcc gcc gag cca gag        48
Met Met Leu Ala Tyr Met Asp Arg Ala Thr Ala Ala Ala Glu Pro Glu
 1               5                  10                  15 gac gcc ggc cgc gag ccc gcc acc atg gcg ggc ggg tgc gcg gcg gcg        96
Asp Ala Gly Arg Glu Pro Ala Thr Met Ala Gly Gly Cys Ala Ala Ala
                20                  25                  30 gcg acg gat ttc ggc ggg ctg ggg agc gcc atg ccc gcg gcc gtg gtc       144
Ala Thr Asp Phe Gly Gly Leu Gly Ser Ala Met Pro Ala Ala Val Val
            35                  40                  45 cgc ccg gcg agc gcg gac gac gtg gcc agc gcc atc cgc gcg gcg gcg       192
Arg Pro Ala Ser Ala Asp Asp Val Ala Ser Ala Ile Arg Ala Ala Ala
        50                  55                  60 ctg acg ccg cac ctc acc gtg gcc gcc cgc ggg aac ggg cac tcg gtg       240
Leu Thr Pro His Leu Thr Val Ala Ala Arg Gly Asn Gly His Ser Val
 65                  70                  75                  80 gcc ggc cag gcc atg gcc gag ggc ggg ctg gtc ctc gac atg cgc tcg       288
Ala Gly Gln Ala Met Ala Glu Gly Gly Leu Val Leu Asp Met Arg Ser
                85                  90                  95 ctc gcg gcg ccg tcc cgg cgc gcg cag atg cag ctc gtc gtg cag tgc       336
Leu Ala Ala Pro Ser Arg Arg Ala Gln Met Gln Leu Val Val Gln Cys
            100                 105                 110 ccc gac ggc ggc ggc ggc cgc cgc tgc ttc gcc gac gtc ccc ggc ggc       384
Pro Asp Gly Gly Gly Gly Arg Arg Cys Phe Ala Asp Val Pro Gly Gly
        115                 120                 125 gcg ctc tgg gag gag gtg ctc cac tgg gcc gtc gac aac cac ggg ctc       432
Ala Leu Trp Glu Glu Val Leu His Trp Ala Val Asp Asn His Gly Leu
130                 135                 140 gcc ccg gcg tcc tgg acg gac tac ctc cgc ctc acc gtg ggc ggc acg       480
Ala Pro Ala Ser Trp Thr Asp Tyr Leu Arg Leu Thr Val Gly Gly Thr
145                 150                 155                 160 ctc tcc aat ggc ggc gtc agc ggc cag tcc ttc cgc tac ggg ccc cag       528
Leu Ser Asn Gly Gly Val Ser Gly Gln Ser Phe Arg Tyr Gly Pro Gln
                165                 170                 175 gtg tcc aac gtg gcc gag ctc gag gtg gtc acc ggc gac ggc gag cgc       576
Val Ser Asn Val Ala Glu Leu Glu Val Val Thr Gly Asp Gly Glu Arg
            180                 185                 190 cgc gtc tgc tcg ccc tcc tcc cac ccg gac ctc ttc ttc gcc gtg ctc       624
Arg Val Cys Ser Pro Ser Ser His Pro Asp Leu Phe Phe Ala Val Leu
        195                 200                 205 ggc ggg ctc ggc cag ttt ggc gtc atc acg cgc gcc cgc atc ccg ctc       672
Gly Gly Leu Gly Gln Phe Gly Val Ile Thr Arg Ala Arg Ile Pro Leu
    210                 215                 220 cac agg gcg ccc aag gcg gtg cgg tgg acg cgc gtg gtg tac gcg agc       720
His Arg Ala Pro Lys Ala Val Arg Trp Thr Arg Val Val Tyr Ala Ser
225                 230                 235                 240 atc gcg gac tac acg gcg gac gcg gag tgg ctg gtg acg cgg ccc ccc       768
```

| | | |
|---|---|---|
| Ile Ala Asp Tyr Thr Ala Asp Ala Glu Trp Leu Val Thr Arg Pro Pro<br>               245                         250               255 | |
| gac gcg gcg ttc gac tac gtg gag ggc ttc gcg ttc gtg aac agc gac<br>Asp Ala Ala Phe Asp Tyr Val Glu Gly Phe Ala Phe Val Asn Ser Asp<br>           260                   265               270 | 816 |
| gac ccc gtg aac ggc tgg ccg tcc gtg ccc atc ccc ggc ggc gcc cgc<br>Asp Pro Val Asn Gly Trp Pro Ser Val Pro Ile Pro Gly Gly Ala Arg<br>         275                   280               285 | 864 |
| ttc gac ccg tcc ctc ctc ccc gcc ggc gcc ggc ccc gtc ctc tac tgc<br>Phe Asp Pro Ser Leu Leu Pro Ala Gly Ala Gly Pro Val Leu Tyr Cys<br>     290                 295               300 | 912 |
| ctg gag gtg gcc ctg tac cag tac gcg cac cgg ccc gac gac gac gac<br>Leu Glu Val Ala Leu Tyr Gln Tyr Ala His Arg Pro Asp Asp Asp Asp<br>305                  310               315               320 | 960 |
| gag gag gac cag gcg gcg gtg acc gtg agc cgg atg atg gcg ccg ctc<br>Glu Glu Asp Gln Ala Ala Val Thr Val Ser Arg Met Met Ala Pro Leu<br>                 325               330               335 | 1008 |
| aag cac gtg cgg ggc ctg gag ttc gcg gcg gac gtc ggg tac gtg gac<br>Lys His Val Arg Gly Leu Glu Phe Ala Ala Asp Val Gly Tyr Val Asp<br>           340                   345               350 | 1056 |
| ttc ctg tcc cgc gtg aac cgg gtg gag gag gag gcc cgg cgc aac ggc<br>Phe Leu Ser Arg Val Asn Arg Val Glu Glu Glu Ala Arg Arg Asn Gly<br>     355                 360               365 | 1104 |
| agc tgg gac gcg ccg cac ccg tgg ctc aac ctc ttc gtc tcc gcg cgc<br>Ser Trp Asp Ala Pro His Pro Trp Leu Asn Leu Phe Val Ser Ala Arg<br>   370                 375               380 | 1152 |
| gac atc gcc gac ttc gac cgc gcc gtc atc aag ggc atg ctc gcc gac<br>Asp Ile Ala Asp Phe Asp Arg Ala Val Ile Lys Gly Met Leu Ala Asp<br>385                  390               395               400 | 1200 |
| ggc atc gac ggg ccc atg ctc gtc tac cct atg ctc aag agc aag tgg<br>Gly Ile Asp Gly Pro Met Leu Val Tyr Pro Met Leu Lys Ser Lys Trp<br>                 405               410               415 | 1248 |
| gac ccc aac acg tcg gtg gcg ctg ccg gag ggc gag gtc ttc tac ctg<br>Asp Pro Asn Thr Ser Val Ala Leu Pro Glu Gly Glu Val Phe Tyr Leu<br>           420                   425               430 | 1296 |
| gtg gcg ctg ctg cgg ttc tgc cgg agc ggc ggg ccg gcg gtg gac gag<br>Val Ala Leu Leu Arg Phe Cys Arg Ser Gly Gly Pro Ala Val Asp Glu<br>     435                 440               445 | 1344 |
| ctg gtg gcg cag aac ggc gcc atc ctc cgc gcc tgc cgc gcc aac ggc<br>Leu Val Ala Gln Asn Gly Ala Ile Leu Arg Ala Cys Arg Ala Asn Gly<br>   450                 455               460 | 1392 |
| tac gac tac aag gcc tac ttc ccg agc tac cgc ggc gag gcc gac tgg<br>Tyr Asp Tyr Lys Ala Tyr Phe Pro Ser Tyr Arg Gly Glu Ala Asp Trp<br>465                  470               475               480 | 1440 |
| gcg cgc cac ttc ggc gcc gcc agg tgg agg cgc ttc gtg gac cgc aag<br>Ala Arg His Phe Gly Ala Ala Arg Trp Arg Arg Phe Val Asp Arg Lys<br>                 485               490               495 | 1488 |
| gcc cgg tac gac ccg ctg gcg atc ctc gcg ccg ggc cag aag atc ttc<br>Ala Arg Tyr Asp Pro Leu Ala Ile Leu Ala Pro Gly Gln Lys Ile Phe<br>         500                 505               510 | 1536 |
| cct cgg gtc ccg gcg tcc gtc gcc gtg tag<br>Pro Arg Val Pro Ala Ser Val Ala Val *<br>         515                 520 | 1566 |

<210> SEQ ID NO 31
<211> LENGTH: 521
<212> TYPE: PRT
<213> ORGANISM: Zea mays

<400> SEQUENCE: 31

-continued

```
Met Met Leu Ala Tyr Met Asp Arg Ala Thr Ala Ala Glu Pro Glu
 1               5                  10                  15

Asp Ala Gly Arg Glu Pro Ala Thr Met Ala Gly Gly Cys Ala Ala Ala
                20                  25                  30

Ala Thr Asp Phe Gly Gly Leu Gly Ser Ala Met Pro Ala Ala Val Val
            35                  40                  45

Arg Pro Ala Ser Ala Asp Asp Val Ala Ser Ala Ile Arg Ala Ala Ala
        50                  55                  60

Leu Thr Pro His Leu Thr Val Ala Ala Arg Gly Asn Gly His Ser Val
 65              70                  75                  80

Ala Gly Gln Ala Met Ala Glu Gly Gly Leu Val Leu Asp Met Arg Ser
                85                  90                  95

Leu Ala Ala Pro Ser Arg Arg Ala Gln Met Gln Leu Val Val Gln Cys
            100                 105                 110

Pro Asp Gly Gly Gly Gly Arg Arg Cys Phe Ala Asp Val Pro Gly Gly
        115                 120                 125

Ala Leu Trp Glu Glu Val Leu His Trp Ala Val Asp Asn His Gly Leu
    130                 135                 140

Ala Pro Ala Ser Trp Thr Asp Tyr Leu Arg Leu Thr Val Gly Gly Thr
145                 150                 155                 160

Leu Ser Asn Gly Gly Val Ser Gly Gln Ser Phe Arg Tyr Gly Pro Gln
                165                 170                 175

Val Ser Asn Val Ala Glu Leu Glu Val Val Thr Gly Asp Gly Glu Arg
            180                 185                 190

Arg Val Cys Ser Pro Ser Ser His Pro Asp Leu Phe Phe Ala Val Leu
        195                 200                 205

Gly Gly Leu Gly Gln Phe Gly Val Ile Thr Arg Ala Arg Ile Pro Leu
    210                 215                 220

His Arg Ala Pro Lys Ala Val Arg Trp Thr Arg Val Val Tyr Ala Ser
225                 230                 235                 240

Ile Ala Asp Tyr Thr Ala Asp Ala Glu Trp Leu Val Thr Arg Pro Pro
                245                 250                 255

Asp Ala Ala Phe Asp Tyr Val Glu Gly Phe Ala Phe Val Asn Ser Asp
            260                 265                 270

Asp Pro Val Asn Gly Trp Pro Ser Val Pro Ile Pro Gly Gly Ala Arg
        275                 280                 285

Phe Asp Pro Ser Leu Leu Pro Ala Gly Ala Gly Pro Val Leu Tyr Cys
    290                 295                 300

Leu Glu Val Ala Leu Tyr Gln Tyr Ala His Arg Pro Asp Asp Asp
305                 310                 315                 320

Glu Glu Asp Gln Ala Ala Val Thr Val Ser Arg Met Met Ala Pro Leu
                325                 330                 335

Lys His Val Arg Gly Leu Glu Phe Ala Ala Asp Val Gly Tyr Val Asp
            340                 345                 350

Phe Leu Ser Arg Val Asn Arg Val Glu Glu Glu Ala Arg Arg Asn Gly
        355                 360                 365

Ser Trp Asp Ala Pro His Pro Trp Leu Asn Leu Phe Val Ser Ala Arg
    370                 375                 380

Asp Ile Ala Asp Phe Asp Arg Ala Val Ile Lys Gly Met Leu Ala Asp
385                 390                 395                 400

Gly Ile Asp Gly Pro Met Leu Val Tyr Pro Met Leu Lys Ser Lys Trp
                405                 410                 415

Asp Pro Asn Thr Ser Val Ala Leu Pro Glu Gly Glu Val Phe Tyr Leu
```

```
                  420               425               430
Val Ala Leu Leu Arg Phe Cys Arg Ser Gly Gly Pro Ala Val Asp Glu
                435                       440                 445

Leu Val Ala Gln Asn Gly Ala Ile Leu Arg Ala Cys Arg Ala Asn Gly
        450                       455                 460

Tyr Asp Tyr Lys Ala Tyr Phe Pro Ser Tyr Arg Gly Glu Ala Asp Trp
465                       470                 475                 480

Ala Arg His Phe Gly Ala Ala Arg Trp Arg Phe Val Asp Arg Lys
                    485                 490                 495

Ala Arg Tyr Asp Pro Leu Ala Ile Leu Ala Pro Gly Gln Lys Ile Phe
            500                 505                 510

Pro Arg Val Pro Ala Ser Val Ala Val
                515             520

<210> SEQ ID NO 32
<211> LENGTH: 1629
<212> TYPE: DNA
<213> ORGANISM: Zea mays
<220> FEATURE:
<221> NAME/KEY: CDS
<222> LOCATION: (1)...(1629)

<400> SEQUENCE: 32 atg gag gtt gcc atg gtc gtg agc gca aga gcc agc ctg ctg atc ctc     48
Met Glu Val Ala Met Val Val Ser Ala Arg Ala Ser Leu Leu Ile Leu
 1               5                  10                  15 gtc ctc tcc ctc tgc tct ccg tac aaa ttc ata cag agc ccc atg gac     96
Val Leu Ser Leu Cys Ser Pro Tyr Lys Phe Ile Gln Ser Pro Met Asp
                20                  25                  30 ctg ggc ccc ctg aac ctg ctc ccc acc acc agc acc gcg gcc gcg tcc    144
Leu Gly Pro Leu Asn Leu Leu Pro Thr Thr Ser Thr Ala Ala Ala Ser
            35                  40                  45 agc gac ttc ggc agg ata ctc ttc cgc gcc ccg gcc gcg gtg ctg agg    192
Ser Asp Phe Gly Arg Ile Leu Phe Arg Ala Pro Ala Ala Val Leu Arg
        50                  55                  60 ccc cag tcg ccg agg gac atc tcc atg ctg ctc agc ttc ctc tcc ggc    240
Pro Gln Ser Pro Arg Asp Ile Ser Met Leu Leu Ser Phe Leu Ser Gly
 65                  70                  75                  80 tcg ccc tcg ctg agc agg gtc acg gtg gcg gcc agg ggg gca ggc cac    288
Ser Pro Ser Leu Ser Arg Val Thr Val Ala Ala Arg Gly Ala Gly His
                85                  90                  95 tcc atc cac ggg cag gcg cag gcc ccg gac ggc att gtg gtg gag acg    336
Ser Ile His Gly Gln Ala Gln Ala Pro Asp Gly Ile Val Val Glu Thr
                100                 105                 110 cgc tcc ttg ccc ggc gag atg gag ttc cac cac gtc cgc ggg gga ggc    384
Arg Ser Leu Pro Gly Glu Met Glu Phe His His Val Arg Gly Gly Gly
        115                 120                 125 gaa ggg cgt gcc tcc tac gcc gac gtg ggc ggc ggg gtt ctg tgg atc    432
Glu Gly Arg Ala Ser Tyr Ala Asp Val Gly Gly Gly Val Leu Trp Ile
130                 135                 140 gag ctc ctg gag cgg agc ctg aag ctt ggg ctg gct ccc agg tcc tgg    480
Glu Leu Leu Glu Arg Ser Leu Lys Leu Gly Leu Ala Pro Arg Ser Trp
145                 150                 155                 160 acc gac tac ctc tac ctc act gtc ggc ggg acg ctg tcc aat gcc ggc    528
Thr Asp Tyr Leu Tyr Leu Thr Val Gly Gly Thr Leu Ser Asn Ala Gly
                165                 170                 175 atc agc ggg cag acg ttc aag cac ggg cca cag atc agc aac gtc ctc    576
Ile Ser Gly Gln Thr Phe Lys His Gly Pro Gln Ile Ser Asn Val Leu
            180                 185                 190
```

```
cag ctg gag gta gtc aca gga cga ggg gag att gtg gaa tgc tca ccc        624
Gln Leu Glu Val Val Thr Gly Arg Gly Glu Ile Val Glu Cys Ser Pro
        195                 200                 205 agc aag gag gcc gac ctg ttc aat gcc gtc ctg gga ggc cta ggc cag        672
Ser Lys Glu Ala Asp Leu Phe Asn Ala Val Leu Gly Gly Leu Gly Gln
    210                 215                 220 ttc ggc atc ata acc agg gcc agg atc ctg ctg cag gag gct ccg gag        720
Phe Gly Ile Ile Thr Arg Ala Arg Ile Leu Leu Gln Glu Ala Pro Glu
225                 230                 235                 240 aag gtg acg tgg gtg agg gcc ttc tac gac gac ttg ggc gcc ttc acc        768
Lys Val Thr Trp Val Arg Ala Phe Tyr Asp Asp Leu Gly Ala Phe Thr
                245                 250                 255 agg gac cag gag ctg ctg gtg tcg att ccg gat tcg gtg gac tac gtg        816
Arg Asp Gln Glu Leu Leu Val Ser Ile Pro Asp Ser Val Asp Tyr Val
        260                 265                 270 gaa ggg ttc atg gtc ctg aac gag cgg tcc ctc cac agc tcc tcc atc        864
Glu Gly Phe Met Val Leu Asn Glu Arg Ser Leu His Ser Ser Ser Ile
    275                 280                 285 gcc ttc ccc gcg agc gtg gac ttc agc ccg gat ttc ggc acc agg agc        912
Ala Phe Pro Ala Ser Val Asp Phe Ser Pro Asp Phe Gly Thr Arg Ser
290                 295                 300 agc cct agg atc tac tac tgc gtc gag ttc gcg gtc cac cac cac cac        960
Ser Pro Arg Ile Tyr Tyr Cys Val Glu Phe Ala Val His His His His
305                 310                 315                 320 ggt tac cag cag cag tct cag gcg gcc gtg gag gcc atc tcg agg cgg       1008
Gly Tyr Gln Gln Gln Ser Gln Ala Ala Val Glu Ala Ile Ser Arg Arg
                325                 330                 335 atg agc cac atg gcg tcc cag ctg tac agc gtg gag gtg tcc tac ttg       1056
Met Ser His Met Ala Ser Gln Leu Tyr Ser Val Glu Val Ser Tyr Leu
        340                 345                 350 gac ttc ctg aac cgg gtc agg atg gag gag gtg agc ctg cgg agc gcc       1104
Asp Phe Leu Asn Arg Val Arg Met Glu Glu Val Ser Leu Arg Ser Ala
    355                 360                 365 ggg atg tgg gag gag gtg cac cac ccg tgg ctc aac atg ttc gtg ccc       1152
Gly Met Trp Glu Glu Val His His Pro Trp Leu Asn Met Phe Val Pro
370                 375                 380 aag gcc ggg gtc gct ggc ttc agg gat ctg ctc atg gac aac gtc tcg       1200
Lys Ala Gly Val Ala Gly Phe Arg Asp Leu Leu Met Asp Asn Val Ser
385                 390                 395                 400 ccg gat agc ttc cag ggc ctc atc ctc atc tac cca ctc ctc aga gac       1248
Pro Asp Ser Phe Gln Gly Leu Ile Leu Ile Tyr Pro Leu Leu Arg Asp
                405                 410                 415 aag tgg gac acc aac acg tcg gtc gtg atc ccg gac tcc ggg ccc acc       1296
Lys Trp Asp Thr Asn Thr Ser Val Val Ile Pro Asp Ser Gly Pro Thr
        420                 425                 430 gcg gac gac ccg gtg atg tac gtg gtc ggc atc ctc agg tcc gcg aac       1344
Ala Asp Asp Pro Val Met Tyr Val Val Gly Ile Leu Arg Ser Ala Asn
    435                 440                 445 cct ggt cca gaa gaa gac ggt gac ggc tgc tcc cac cgc tgc ctg cac       1392
Pro Gly Pro Glu Glu Asp Gly Asp Gly Cys Ser His Arg Cys Leu His
450                 455                 460 gag ctc ctc cgc agc cac cgc cgg atc gcc gac gcc gcg gag gcg cgc       1440
Glu Leu Leu Arg Ser His Arg Arg Ile Ala Asp Ala Ala Glu Ala Arg
465                 470                 475                 480 ctc ggc gcc aag cag tac ctg cct cac cac ccg acc ccg gcc cgc tgg       1488
Leu Gly Ala Lys Gln Tyr Leu Pro His His Pro Thr Pro Ala Arg Trp
                485                 490                 495 cag cag cac ctg ggc cgg cgc tgg gag cgc ttc gcg gac cgc aag gcc       1536
Gln Gln His Leu Gly Arg Arg Trp Glu Arg Phe Ala Asp Arg Lys Ala
        500                 505                 510
```

```
cgg ttc gac ccg ctg cgc atc ctg ggg ccc ggc cag ggc ata ttc cct      1584
Arg Phe Asp Pro Leu Arg Ile Leu Gly Pro Gly Gln Gly Ile Phe Pro
        515                 520                 525 cgg acg gcc cag gat gct gcc gcc gct gcg tac ggg agc tag              1629
Arg Thr Ala Gln Asp Ala Ala Ala Ala Ala Tyr Gly Ser *
        530                 535                 540

<210> SEQ ID NO 33
<211> LENGTH: 542
<212> TYPE: PRT
<213> ORGANISM: Zea mays

<400> SEQUENCE: 33

Met Glu Val Ala Met Val Val Ser Ala Arg Ala Ser Leu Leu Ile Leu
 1               5                  10                  15

Val Leu Ser Leu Cys Ser Pro Tyr Lys Phe Ile Gln Ser Pro Met Asp
                20                  25                  30

Leu Gly Pro Leu Asn Leu Leu Pro Thr Thr Ser Thr Ala Ala Ala Ser
            35                  40                  45

Ser Asp Phe Gly Arg Ile Leu Phe Arg Ala Pro Ala Ala Val Leu Arg
        50                  55                  60

Pro Gln Ser Pro Arg Asp Ile Ser Met Leu Leu Ser Phe Leu Ser Gly
 65                  70                  75                  80

Ser Pro Ser Leu Ser Arg Val Thr Val Ala Ala Arg Gly Ala Gly His
                85                  90                  95

Ser Ile His Gly Gln Ala Gln Ala Pro Asp Gly Ile Val Val Glu Thr
            100                 105                 110

Arg Ser Leu Pro Gly Glu Met Glu Phe His His Val Arg Gly Gly Gly
        115                 120                 125

Glu Gly Arg Ala Ser Tyr Ala Asp Val Gly Gly Val Leu Trp Ile
    130                 135                 140

Glu Leu Leu Glu Arg Ser Leu Lys Leu Gly Leu Ala Pro Arg Ser Trp
145                 150                 155                 160

Thr Asp Tyr Leu Tyr Leu Thr Val Gly Gly Thr Leu Ser Asn Ala Gly
                165                 170                 175

Ile Ser Gly Gln Thr Phe Lys His Gly Pro Gln Ile Ser Asn Val Leu
            180                 185                 190

Gln Leu Glu Val Val Thr Gly Arg Gly Glu Ile Val Glu Cys Ser Pro
        195                 200                 205

Ser Lys Glu Ala Asp Leu Phe Asn Ala Val Leu Gly Gly Leu Gly Gln
    210                 215                 220

Phe Gly Ile Ile Thr Arg Ala Arg Ile Leu Leu Gln Glu Ala Pro Glu
225                 230                 235                 240

Lys Val Thr Trp Val Arg Ala Phe Tyr Asp Asp Leu Gly Ala Phe Thr
                245                 250                 255

Arg Asp Gln Glu Leu Leu Val Ser Ile Pro Asp Ser Val Asp Tyr Val
            260                 265                 270

Glu Gly Phe Met Val Leu Asn Glu Arg Ser Leu His Ser Ser Ser Ile
        275                 280                 285

Ala Phe Pro Ala Ser Val Asp Phe Ser Pro Asp Phe Gly Thr Arg Ser
    290                 295                 300

Ser Pro Arg Ile Tyr Tyr Cys Val Glu Phe Ala Val His His His
305                 310                 315                 320

Gly Tyr Gln Gln Gln Ser Gln Ala Ala Val Glu Ala Ile Ser Arg Arg
                325                 330                 335
```

```
Met Ser His Met Ala Ser Gln Leu Tyr Ser Val Glu Val Ser Tyr Leu
            340                 345                 350

Asp Phe Leu Asn Arg Val Arg Met Glu Glu Val Ser Leu Arg Ser Ala
            355                 360                 365

Gly Met Trp Glu Glu Val His His Pro Trp Leu Asn Met Phe Val Pro
            370                 375                 380

Lys Ala Gly Val Ala Gly Phe Arg Asp Leu Leu Met Asp Asn Val Ser
385                 390                 395                 400

Pro Asp Ser Phe Gln Gly Leu Ile Leu Ile Tyr Pro Leu Leu Arg Asp
                    405                 410                 415

Lys Trp Asp Thr Asn Thr Ser Val Val Ile Pro Asp Ser Gly Pro Thr
            420                 425                 430

Ala Asp Pro Val Met Tyr Val Gly Ile Leu Arg Ser Ala Asn
            435                 440                 445

Pro Gly Pro Glu Glu Asp Gly Asp Gly Cys Ser His Arg Cys Leu His
            450                 455                 460

Glu Leu Leu Arg Ser His Arg Arg Ile Ala Asp Ala Ala Glu Ala Arg
465                 470                 475                 480

Leu Gly Ala Lys Gln Tyr Leu Pro His His Pro Thr Pro Ala Arg Trp
                    485                 490                 495

Gln Gln His Leu Gly Arg Arg Trp Glu Arg Phe Ala Asp Arg Lys Ala
            500                 505                 510

Arg Phe Asp Pro Leu Arg Ile Leu Gly Pro Gly Gln Gly Ile Phe Pro
            515                 520                 525

Arg Thr Ala Gln Asp Ala Ala Ala Ala Ala Tyr Gly Ser
            530                 535                 540

<210> SEQ ID NO 34
<211> LENGTH: 3003
<212> TYPE: DNA
<213> ORGANISM: Zea mays
<220> FEATURE:
<221> NAME/KEY: misc_feature
<222> LOCATION: (0)...(0)
<223> OTHER INFORMATION: ZmCkx2 promoter

<400> SEQUENCE: 34
ctgccatcct catgcagatg agacggagag aagatgagaa agtacaaga tcccagaagc      60 aagcagcagg atgggccat ccccccccc cccactggg ccccacgggc cgaaagccac      120
cggcgaaaat gtccagaagg ccacgtgggg catgggtccc cggagtccac ttccgcgcga      180
tctcgaggcc gggccgcacc ggcaatcgct ctccggccac ctccctgctt cctcaggtcc      240
ggtctcccat agtccaatgc atgcatgcac gagcatcccc tcagaacgct ggcagtgagt      300
gtcttgctcg cacatcagct tggccagtca gtgcgagaac acagcagcaa caacaacaac      360
aacacctgtg cacaatggcg tctatcattg gtaccatctc aatcggctga cttgtctata      420
actactgtta acggaggtcc cttgtgcatc atgcagtttt agaagagcac ctcgatcgca      480
agcgcctcat tattatcatc attctcttaa actggtcaga aaactgacca tcagctaaag      540
tgatactgac atactgtatc tttgtagata attaaatgga gaaaaatctc cttctgttcc      600
gtctggccgt taaatgccga atccatgcat atataaatct gtacgtaggc tcaaagcaca      660
gtgtgcattt tggctttcca gctagcatac atacatgtga ctgctgacga tgaattgtgt      720
ggaccacatt ggcacaacgg tgcattgcaa cggacgggcg ccgtcaaggt caaacgcata      780
aaaggctgtc atttggcaac acaatgaatc agtggcgcca cgccatccgt ccacgatcca      840
```

```
ccgttcttgg tgtagtggtt ggtcccagcg cttgaaggcc aggccgaggc cgtgttctgg    900
aaggtggcct gtggtgagca ctaaacatgt gtgtgctttt gcctttccaa gccagagggc    960
cggtctctta atatacataa catacacacc acttttcat tttgttcatt attacggtct   1020
aatgcaaaca aagccatttg cagaatgtgc tacatagcag gtatgttct ctttttttcc   1080
ctgtaaaatt tgtagactta tcacaagaat aagtttaacc attactagaa tagttcctca   1140
catgtttgtt taccatcggg gcgggaacag cttgcattgc aaaagctgcg caagtattag   1200
ggccctctag attttttaa tagtagtagt atatataata tataggtgtt actatttgag   1260
ttgttaggcc atctgcggca gattttctat gacatccctt atttcaaact ttattttgca   1320
aacagttgtc atataccta ttttaggcga atcactgaag acaggtaagt tttggcacgg   1380
atgaggtgga gagtggacaa gaatctccgt tgtggagtct gcctaccagt accaggcaaa   1440
gtaatgcatg cgcgcggaca ggatggacgg tcgaagtggc ctccctgcct ccacccgac   1500
gacgacgcat gggctccgtc cccttcgctt gcttcctgct ccagctagct ccatcgccta   1560
gtgctccgct ccgccgcaca ggaacggaac ggaacggacc gaaccacttg gtcgcatccc   1620
gatgcgttgc cgtctgccgg tgtccatcgt gtcggtttca cctctgcact agcataaatt   1680
ccttgacacc aacagcgagc gacatcatcg gctcagccct acaagtcacg agtgttctga   1740
ctgaccagct agcaatagca atctgctgct ctgcttgact tgctcggacg atccgccgct   1800
gcttgcgttc ggctccagta ggctatcctc cgcgacgtcg tcgatctgga ctccatggcg   1860
tccacacaga atcgacacga gcttggtgtg ccgcgtacgc atgtgtgcgt atgtatgcct   1920
cgtcttccac atgcaaacat acgcagagga aggggaaagg cggcagcaaa cgcgacggtc   1980
caagtcgtac cacagaagtg gtcgcgcatg tgtgcccaag ttgccatcac ccggatgcta   2040
ttagatttcc agaaactaac ttgtgaggac ccctggtgtc tgctagctgc tctccaactc   2100
caacctgtca atcaattccc agacggacaa gctgagctca cagctcaagc tcaacaacga   2160
tggccggccg ggtcaccatg gaactgatcc tctacagtac aggcatggga aaatggagga   2220
ggagagcagg gcagtgaggc cacagaatca gaggctgatt agtgttggtg agctccaatc   2280
caacagcata tgaccagcga gcagaacata gggatgtcct gtgggcttgc ccagggacag   2340
acgcatgcaa gccatgtgac tgtccggaga gagagccggt gatactggaa cagaggatcc   2400
gatcctgccc cccttctttt gcctctccct ctctcacaca cacagtctca cctatatgtg   2460
gctatgtcgt ctccattagg ctgttaacta gccaacacat gttcccccgt tgcttaagac   2520
agcagctaca aagcgagaac atcatgctct aaaaagaaac ttccgcaatg caccactagc   2580
acatgtctgc gcctcaattc gcaaccggca agcaagcaag ccggcaagca gacagtcgcc   2640
atacggtttt taccaaacag ctagcgccca cagctgacta gctgaccacc gcaccaccca   2700
cactcctcct cgcgagtcgc gaggcaagcc gcaagtcct atatagagag gcccctccc   2760
tccccctgca tggacagcca ccgccttctt caaccctcct tccgtcttcc tcctctagtc   2820
ttacctcgtt gcacctcaag aaacttggcg cgcaaccagg aaaccccctc ttctctctct   2880
ctctctctct ctctctctgc cttctgattc caagctcccc aactgcccag caccaacctg   2940
ccgaactccc ctccttttg ttggtttgtc gaattataaa ttgagcccgg ccggctgact   3000
acc                                                                3003

<210> SEQ ID NO 35
<211> LENGTH: 2001
<212> TYPE: DNA
```

```
<213> ORGANISM: Zea mays
<220> FEATURE:
<221> NAME/KEY: misc_feature
<222> LOCATION: (0)...(0)
<223> OTHER INFORMATION: Promoter for ZmCkx3
<220> FEATURE:
<221> NAME/KEY: misc_feature
<222> LOCATION: (0)...(0)
<223> OTHER INFORMATION: n = A, T, C, or G

<400> SEQUENCE: 35
```

| | | | | | |
|---|---|---|---|---|---|
| ccggggtgtg | acaggagcat | tgaagcatgc | atgctctgct | cagcatataa | ttaaagaaag | 60 |
| aagcatcaaa | atgcactgga | gcagttgacc | aaaacttgca | gctacgtcaa | aatatatacg | 120 |
| agggctggca | tcaaggtgtg | ctcagcccga | gccccgtcag | gtaacttggt | cttttgtttt | 180 |
| ctggccttgc | ggcttcatta | aaggccgccg | gccgcgagcg | aggcaaaaca | gtgaagggga | 240 |
| ggggaggtgc | ccgccactaa | cctctcggtc | ggatatatta | gtattcaagc | agttgacaaa | 300 |
| tctgtgcgga | tttgatttgg | tctgaggaaa | atatatatat | atatatatat | agcccctcgt | 360 |
| cgttcatgca | ccctctcgca | gcctgcaacc | ttacaatatt | gttcttgcat | ccggttttat | 420 |
| ttatatttt | atttttaaa | aaaaaaatcc | atagtcctgc | cgtcttgaag | gatatgtttt | 480 |
| tctttaccca | tgcacggcgg | agtttaaatt | tgcgctgacc | cgactgctcg | tgaacagaga | 540 |
| caagtatgac | agatatcgtt | gagttccaaa | ttttaaaaaa | aaaatcaata | aaaaatttaa | 600 |
| aacagaatgt | tgacgaggaa | aaaaaatatg | aaggtgcttg | cacacctgtc | actccatgcc | 660 |
| ggacatcaac | aaattaattg | ttcaagtggt | gggagtcagc | tgcttccagt | ttaccttcct | 720 |
| gcgccagcgg | ttggtagaca | ggattgttgc | cacgtggacg | aaatctcctg | ccgccagctg | 780 |
| gttgatcacg | gcaggcagtc | acatgcttct | tgccaagatt | accgcgggtt | gtaatcatct | 840 |
| gaaatatatt | aacctgagca | cgtgatagag | taaaaaaatt | ggtcgactaa | gggggtgttt | 900 |
| ggtttctagg | gactaatgtt | tagtccctac | attttattcc | attttagttc | taaaattacc | 960 |
| aaatatagaa | actaaaactt | tattttagtt | tctatattag | caatttatag | actaaaaaag | 1020 |
| aataaaatga | agggactaaa | tattaatccc | tagaaaccaa | acaccccta | actttaggta | 1080 |
| agttgtggca | tgcattctct | ggaacggcag | ttctagagag | cacttgagat | gtcaacaggt | 1140 |
| gaagaattga | agattggcca | acacaggcgt | tcaaggagat | tcaaccaccc | atccacatac | 1200 |
| cgcgcaaaca | cttgggggc | attcttgctg | ctgccacatt | tggaagaagc | gcagcaatgt | 1260 |
| ggtgttcaga | agaagcacag | ctattttagc | tcttgataac | tatcttttt | tttgcataga | 1320 |
| ttaatttatt | tcttcgatat | atactagctt | gtaaaaaaat | gttttncaga | tatatgtata | 1380 |
| aaaatgtgta | cctagtacct | acgcatgtct | tagttcaaca | tacttgatag | ctgtagtttt | 1440 |
| ctgaaaacct | gttcaaatta | accttttttcc | taccctgatg | gtgaatagag | agaaaagctt | 1500 |
| tacctttgtc | tgaataagaa | aactaacaga | aagcttacat | tttggccact | ctacctgccc | 1560 |
| gagtattttc | taagcaagca | aaggcgcatg | aaaattttct | cggaatccat | gacctttac | 1620 |
| gcgcantgnw | aaayawwgwm | mattgmtcmg | accaatgatc | attttgatac | tctccacaag | 1680 |
| tcaacatctc | aaaaaaacca | caagatgggg | cccatcaaca | taagttcacg | agtgtgcctt | 1740 |
| caggtacatt | gttcttttt | tttgttttgc | taaagtcaat | cagctgcaaa | atattcagaa | 1800 |
| caatttcaat | aacccgaaag | gctgttgtgc | ctccatttgt | caacgtttgc | gaggccaaat | 1860 |
| ggtaccccg | ctataaatac | catggaagtt | cttggcctct | aggacacaca | agcgatctct | 1920 |
| cctcctatag | tttctataac | cccacaaagc | gtccaggtcc | cgtagtcacc | tccgattgca | 1980 |
| ttgcgttgcc | gcaagacaag | c | | | | 2001 |

<210> SEQ ID NO 36
<211> LENGTH: 2448
<212> TYPE: DNA
<213> ORGANISM: Zea mays
<220> FEATURE:
<221> NAME/KEY: misc_feature
<222> LOCATION: (0)...(0)
<223> OTHER INFORMATION: promoter for ZmCkx4

<400> SEQUENCE: 36

```
ctttatgttg tagccaagga aagtatactg ttaagatcag aatgaacctt ataggagttg      60
tatgggcata aagccagcaa gtatagccaa aggtacacaa ggctaatata gtcaagttgt     120
tgatgtgtga gacgttcaag gaagtgaact attggaggag tcgactaaaa gtacgattaa     180
taaggtagac atgatggtaa aatctttgat ctagaattta agtggtatgg atgcgagggt     240
gagaatggca agcacaactt caaatatagg gtgatgctta tgcttggctg agccatttca     300
ttcatgagca taggaacatg agacatggtg ggatatggat acttgcacaa aaaaaggaat     360
taagtttatg atattcacct cccagtcagt ttgcatggta aaaaaattcc tatcaatttg     420
gttctcaact agggcctaaa attctcaaaa tatctgttgg ggaccattat cgtcgacgat     480
cctcagaatc tgttattacc aaattaaaag gtgtgtttca ggtactgtgc aaagcagcag     540
cgaagctatc cttcgtcaaa agtggctcaa tgaaccaggt ggagaagcta tggagcttcg     600
tctgcgtaga gcgtgccgga ggaggaagct ttggctctga atgcatcgac ttacgaagca     660
tgggagaaga agactcagaa ggcttgtcca gcgtgggaat aaaaaggaga aaatacaatt     720
ttgcccttgt gggatttgta aatcatgtgc aaggctcatg gatatgtttg taattttata     780
tgatatgttt gtaaatcatg gatatgtttt gtaaatcagg tggactagag gagagggagg     840
gtggacatag tgacttgcat cttgatcatg gtagagtggt catggtagag ggaaaggggt     900
aggtcaattc tggagtgcgg ccacggtggc ttgagtgtcg gccacggtag gggaaagggg     960
tagcccaatt ctagggccgg catcggagaa ggccgacatg tgcacgtcag gaggtagtgt    1020
tagaggtttg aacggaaaaa attgaacatg ttagtatgat gagttgtgta attgctggga    1080
attgtggata atttccactt aactacggcc ctgtttattt accctagat tataaaatcc    1140
aacttaaaaa agttgagatg taaacaaaca acacatatta ttaggtggat tatgttatct    1200
agaaatctgg atgataataa tttataagtc ggttaatagg tgtttacata atcgataagc    1260
tggattatat aatcctggaa cacggctttc gcgagagcgt attaaaacag gattccgtga    1320
agcacactat ctgaggagct ccaccaaaag ctgaatctag cccgcactct tttttggagg    1380
attcaaattt ggtgtcactg gagcattcgg cattttgttt catggcgtga agctattttt    1440
actaattaca gaagctgttt caaatagacc tttaaatgat ggctgagtat aaaaggaggc    1500
aatttttta tctcgccgat ggagccaggt cgcgtcgcgc cgcggccgtg ctgcgctctc    1560
gacgcgatct agcggcgatg tgcacagtac agttttgcca tgccattggt taagcctgca    1620
tacaacacac cagcgtactg ccctgcacaa gatctcctcg gctcggcctc tcctgatgga    1680
acgttcagct tgaacagcgg agcgtggggg catcccgggg atgggcgccg cggccgagaa    1740
attttgcaac ctggcaaatc tgccctgtcg catactacca tccacctcca ggcgccaaga    1800
acgcctccga gtttcaggct tgcagctcag ctctgtgttg aattggaacg ggcggagttt    1860
ctgggttcca gacttccagt acaaggcgat caattggtag ggcgaattac ttgcaggccc    1920
agatgcatgg cccatctatc tggttctcta tcggttgctt ttacttgcac aatagtggca    1980
```

```
gacaaactac aagtcagatc cgatcctatc catccatcca tctcgcagcg cgatgcaaat    2040
atgcaatcgt ctgtggaact cgaaaaaaaa cagaggtccg gcctcgcacg aggttaaggg    2100
aaaaaaaacg aagcgtttgg aactttggtt ggcattcgca gcatgctgtg ctgccaccgt    2160 atgttttat ttttgctttg tttgtcttct ttgagaaacg tgagggagcc gcgtgtccgc     2220
tcgttataaa accccccccgg cgacccaaac taccacgagc tcaagcctca agcctcaagc   2280
ctcaagcaag cagagcgccg tgacatcacg aaacaaacat atagagctag ctgctctgcc    2340
tctgcttcac caatcacctg cttggccgcg cggaggggag ggtttccccc tttgacacag    2400
ctgagctccc ctccatcagc agccagctcc tcgtcgcaaa gcaagaag                 2448

<210> SEQ ID NO 37
<211> LENGTH: 2346
<212> TYPE: DNA
<213> ORGANISM: Zea mays
<220> FEATURE:
<221> NAME/KEY: misc_feature
<222> LOCATION: (0)...(0)
<223> OTHER INFORMATION: promoter for ZmCkx5

<400> SEQUENCE: 37
tacagatttg cgttcatcaa tggcagcgcg ggatctcatg aggtcactgg gttcttgcaa      60
gtggggagag aaagggagat ctacgaaaga cttgttagtg ggccaccttt tccctctttc     120
cccacaagga cgagatcgtg gattagagta ggaaagtgat tccgcattgg tctcaaatct    180
tggcgaaaga ttgcattgtg tactctccac cactcgaccg gcaacgaggc attttgttat    240
tgcacgatgc atcctttgca catgagctag gcttgtgcct ttgagtattc agttagcatt    300
gcaaccccat ttcaattcac atgcttgtct ttccaaggaa ctttctaagc cacctaacag    360
acattagggt ttatatcaga atcgagctca tggcgtactt tatgctgcac gaacaatggg    420
ttgggggcgt cgtttcttgc atgagagcat gcgcatcctg gtaaggattt cgccaaaaga    480
actttagtcc tctaccgact ttgtgtttgc gtgatctcgt gatttgaagc ctgtggtggt    540
gtgctgaggc agcatattgg aaggtatctc tgtgttgata tggcatccgt ccgtggacaa    600
atcgatacca catactgttc ttggattcta ttcttgggat tgctaaatga tctagataga    660
ttatattctc ttgttgcagc ccctattgct tcaatacgaa gaaacccaa cgtttagaac     720 ttaataaaac catttgtgag cttagctgct taggcaattc attttatgc atgacaaata     780 tataataata ttagctatac tattattgat gcaacctgtg ggagcgtata aaatggtact    840
tccccaattc taaattataa gacgttttga ctatatattc tacatacata tgtttaattt    900
tatatttaga taatcgctat gccttaatat atagtaaaaa gtagtatatc tagaaaagat    960
aaaacatctt ataatttaaa aatgggtaga gtattatatt agatatgaac agtgcttaga   1020
tgccaccaaa attttgccat gccatcctaa ggccagcaaa agtttgtgtc ttcttttgtt   1080
ttccaaacca ctagatgcca atatactatt tatcatcgat cgagatgtag gtcttagtta   1140
attgtgtcgg gtgcccttga gaaagaaaag aaaaaggtgg gattttgttt tcgcttagac   1200
gatgattgga tctcttggtc tctgaattcc atcccgaata aacaaatgaa gtaggtcctc   1260 agtcacccctt gccctgttag ctgcaagaga gctcatggtt tccagccaca caatcagtcc   1320
atggctcctt cttcttggcc taagtggtgg ccaatcattg tgggtgatcg agtcttgggc   1380
cctctgaaca gtattacaca acagtaatcc tgcaaaagat ttggtatatc tagattctag   1440
agtgagcgcc gtgttgtgcc cagctaggaa tgggttgtca agtgcaacag gaggaggacc   1500
caggatggtc aggtgtaata ggctctcatt aaaagactgt tcagatggat tagagcaacg   1560
```

```
                                      -continued acggggaagc cgggaaaaaa tggttggttc tgctttcctc tcgctccccg gccgggttca    1620
tatatgaatc tgagaacgat attttttgct tcattttca  tttgctatat atttaaactg    1680
tttttttgtg tgtgtgtgtg tgttcattga gctcaatact tgaggcttga tagggagagg    1740
agtgaggcag ctgatcacat ggacctccat ctgaggacag ttcctcttcc gaaacagaaa    1800
ggagagtgca gggaccagcg tggcctgtac agtattgtgt ttgcccttt  cctttggcag    1860 ggacagagag cttcaggctt gtcctcttta tgtatgctgc tcgcctgctt cagagtcaga    1920
gcttcccctt ctcacttctc agagagagag agagagaaga gagagagagg agagccctcc    1980
acagctcccc tgtcctgccc tcaggcattc tttgtcacag ggggcgaggg ctgaagatca    2040
tcacatggtg gcctttttg  ggtctgtggc ctttggtctt ttagtgcttc ttcctttac    2100 ctcctcatga catgaacccc cttttaaac  ctccctcaaa atcaaatcac cctccttctc    2160
ctttaagagc cctcaacccc ttcccctcat tttccttcat ccctcagcct ttgcacaaag    2220
ggcaagaata acgcagtatg atcatctgat catactcccg ccgccatcac aatcccacac    2280
gaacgtgaga caaaggtaac agacgcaaga agctagcagc tgcaggagat tgctcagccc    2340
atctcc                                                              2346

<210> SEQ ID NO 38
<211> LENGTH: 51
<212> TYPE: DNA
<213> ORGANISM: Zea mays

<400> SEQUENCE: 38
caucaucauc auggatccac caatggatct acgtctaatt ttcggtccaa c            51

<210> SEQ ID NO 39
<211> LENGTH: 42
<212> TYPE: DNA
<213> ORGANISM: Zea mays

<400> SEQUENCE: 39
cuacuacuac uagttaactc acattcgaaa tggtggtcct tc                      42
```

MODULATION OF CYTOKININ ACTIVITY IN PLANTS

CROSS-REFERENCE TO RELATED APPLICATIONS

This application is a continuation-in-part of prior application Ser. No. 09/545,334, filed Apr. 7, 2000, now U.S. Pat. No. 6,992,237, which claims the benefit of U.S. Provisional Application No. 60/129,844, filed Apr. 16, 1999; this application also claims the benefit of U.S. Provisional Application No. 60/460,718, filed Apr. 4, 2003. All prior applications to which benefit is claimed are hereby incorporated by reference.

FIELD OF THE INVENTION

This invention relates generally to the field of plant molecular biology. More specifically, this invention relates to methods and reagents for the temporally- or spatially-regulated expression of genes that affect metabolically effective levels of cytokinins in plants, including seeds and the maternal tissue from which such seeds arise, including female inflorescences, ovaries, female florets, aleurone, pedicel, and pedicel-forming regions.

BACKGROUND OF THE INVENTION

Cytokinins are phytohormones involved in numerous physiological processes in plants. Plants respond to environmental stresses in part by modifying the relative balance of active and inactive cytokinins. For instance, during times of abiotic stress (which include, but are not limited to, conditions of drought, density, cold, salinity, and/or soil compaction), increased cytokinin oxidase activity shifts the balance in favor of inactive cytokinins, leading to decreased plant productivity. (Jones and Setter, In CSSA Special Publication No. 29, pp. 25-42. American Society of Agronomy, Madison, Wis. (1999)) Conversely, targeted manipulation of the cytokinin balance in favor of active cytokinins could result in increased productivity, even under abiotic stress, through mechanisms such as increased cell division, induction of stomatal opening, inhibited senescence of organs, and/or suppression of apical dominance. (Morris, R. O. 1997. In Cellular and Molecular Biology of Plant Seed Development, pp. 117-148. Kluwer Academic Publishers. (1997)) In maize subject to unfavorable environmental conditions, cytokinins have been shown to decrease resulting in reduced seed size, increased tip kernel abortion and decreased seed set. (Cheikh and Jones, Plant Physiol. 106:45-51 (1994); Dietrich et al., Plant Physiol Biochem 33:327-336 (1995)). Therefore, these studies show that under stress conditions one approach to improving seed set and seed size would be to maintain the active cytokinin pool above a critical threshold level.

The first naturally occurring cytokinin was purified in 1963 (Letham, D. S., Life Sci. 8:569-573 (1963)) from immature kernels of Zea mays and identified as 6-(4-hydroxy-3-methylbut-trans-2-enylamino) purine, more commonly known today as zeatin. In the main all naturally occurring cytokinins appear to be purine derivatives with a branched 5-carbon $N^6$ substitutent. (See: McGaw, B. A., In: Plant Hormones and their Role in Plant Growth and Development, ed. P. J. Davies, Martinus Nijhoff Publ., Boston, 1987, Chap B3, Pgs. 76-93, the contents of which are incorporated by reference for purposes of background.) While some 25 different naturally occurring cytokinins have been identified, those regarded as particularly active are $N^6$ ($\Delta^2$-isopentenyl) adenosine (iP), zeatin (Z), diHZ, benzyladenine (BAP) and their 9-ribosyl (and in the case of Z and diHZ, their O-glucosyl) derivatives. However, such activity is markedly reduced in the 7- and 9-glucosyl and 9-alanyl conjugates. These latter compounds may be reflective of deactivation or control mechanisms.

The metabolism of cytokinins in plants is complex. Multi-step biochemical pathways are known for the biosynthesis and degradation of cytokinins. At least two major routes of cytokinin biosynthesis are recognized. The first involves transfer RNA (tRNA) as an intermediate. The second involves de novo (direct) biosynthesis. In the first case, tRNAs are known to contain a variety of hypermodified bases (among them are certain cytokinins). These modifications are known to occur at the tRNA polymer level as a post-transcriptional modification. The branched 5-carbon $N^6$ substituent is derived from mevalonic acid pyrophosphate, which undergoes decarboxylation, dehydration, and isomerization to yield $\Delta^2$-isopentenyl pyrophosphate (iPP). The latter condenses with the relevant adenosine residue in the tRNA. Further modifications are then possible. Ultimately the tRNAs are hydrolyzed to their component bases, thereby forming a pool of available free cytokinins.

Alternately, enzymes have been discovered that catalyze the formation of cytokinins de novo, i.e., without a tRNA intermediate. The ipt gene utilized in the practice of this invention is one such gene. The formation of free cytokinins is presumed to begin with [9R5'P] iP. This compound is rapidly and stereospecifically hydroxylated to give the zeatin derivatives from which any number of further metabolic events may ensue. Such events include but are not limited to (1) conjugation, incorporating ribosides, ribotides, glucosides, and amino acids; (2) hydrolysis; (3) reduction; and (4) oxidation. While each enzyme in these pathways is a candidate as an effector of cytokinin levels, enzymes associated with rate-limiting steps have particular utility in the practice of this invention.

One such enzyme is isopentenyl transferase (ipt). An isolated gene encoding ipt was described by van Larebeke et al., (Nature 252:169-170(1974); see also Barry et al., Proc. Nat'l. Acad. Sci. (USA) 81:4776-4780 (1984) and Strabala et al., Mol. Gen. Gen. 216(2-3):388-394 (1989)). Isolation of ipt genes in Arabidopsis has also been reported. (Takei et al., J Biol Chem. 276(28):26405-26410 (2001); Kakimoto et al., Plant Cell Physiol. 42(7):677-685 (2001) and WO 2002/072818; Sun et al., Plant Physiol 131:167-176 (2003)) The invention comprises appropriately modulated expression of ipt genes from any source, including other species, such as maize.

Based on the demonstrable effects of cytokinins in hundreds of experiments across multiple plant species, a transgenic approach to augment active cytokinins in maize could improve its productivity under normal and/or abiotic stress conditions. However, simply increasing the pool of active cytokinins does not automatically lead to enhanced plant growth. In fact, elevating cytokinin levels has been shown to generate detrimental effects on plant phenotype.

For example, Smigocki et al. (Proc. Nat'l. Acad. Sci. (USA) 85:5131-5135(1988)), employing the ipt gene from A. tumefaciens operably linked to either the 35S or NOS promoter, showed a generalized effect on shoot organogenesis and zeatin levels. It was noted that the activity of the promoter controls the degree of morphogenic response observed, and unregulated production of cytokinins can result in unwanted pleiotropic effects. With the constructs identified above, undesirable effects included complete inhibition of root formation in tobacco, and stunted cucumber plantlets that did not survive. (Smigocki et al. (supra); Klee et al., Annual Rev. Plant Physiol. 38:467-486 (1987))

Attempts followed to express the ipt gene in a more controlled fashion. Medford et al. (*The Plant Cell* 1:403-413 (1989)) reported placing the *Agrobacterium* ipt gene under the control of a heat-inducible promoter and expressing same in transgenic rooted tobacco plants. Levels of cytokinin rose dramatically following heat treatment, and effects observed in transgenics included significant reductions in height, xylem content, and leaf size. In both tobacco and *Arabidopsis*, transgenics displayed slower root growth, disorderly root development, and increased axillary bud growth relative to wild-type plants. In addition, the experimental constructs were not satisfactory because the plants exhibited phenotypes associated with excess cytokinin levels, including reduced height, leaf area, and stem width, even in the absence of thermal induction. Further, certain changes were observed in both wild-type and transgenic plants and could be attributed to the heat induction per se.

Schmulling, T. et al. (*FEBS Letters* 249(2):401-406(1989)) transformed tobacco with the *Agrobacterium* ipt gene under control of the *Drosophila* hsp70 promoter, which provides a very low level of expression at normal temperatures and a rapid increase in expression after heat shock. Most heat-shocked transgenic calli were greener, had higher cytokinin concentrations, and grew at a more rapid rate than control calli. Plants regenerated from the heat-shocked transgenic calli were described as "fairly normal" and cytokinin levels in these plants did not differ from those measured in wild-type plants. Plants regenerated from uninduced transgenic calli did not differ from controls in either plant phenotype or cytokinin content. A second experiment created callus tissue transgenic for the ipt gene driven by its native promoter. In shoots regenerated from these calli, high cytokinin levels inhibited root formation. These shoots, grafted onto wild-type tobacco stems, displayed tiny leaves and a stunted, highly-branched growth habit. Thus, transformation either resulted in negative phenotypic changes or had no impact.

In PCT Patent Application Publication No. WO91/01323, 7 Feb. 1991, and U.S. Pat. Nos. 5,177,307, and 4,943,674, tomato plants transformed with the ipt gene linked to fruit-specific promoters (2AII, Z130 and Z70) exhibited modified ripening characteristics. Fruits were described as roughened at immature stages, and as mottled, blotchy, and patchy during ripening. See also U.S. Pat. No. 6,329,570, which discloses transformation of cotton with ipt and a seed-tissue-preferred promoter to modify boll set and fiber quality.

In PCT Patent Application Publication. No. WO93/07272, the ipt gene was fused to the chalcone synthase (chs) promoter from *Antirrhinum maius* and expressed in potato. Phenotypic alterations of transformants included increased tuber yield, plant height and leaf size, thickened stems and delayed leaf senescence. Wang et al. (Australian J of Plant Phys 24(5): 661-672 and 673-683, 1997) reported increased cytokinin levels in leaf laminae and upper stems of tobacco transformed with ipt driven by a chs promoter, as well as release of axillary buds, inhibition of root development, retardation of leaf senescence, elevation of chlorophyll levels, delay in onset of flowering, retardation of flower development, growth of leafy shoots from the primary root, change in leaf shape, enlarged leaf midribs, enlarged veins, thicker stems, greater node number, and increased transpiration rates. Expression of chalcone synthase genes is complex and regulated by a variety of factors, including light, fungal elicitors, wounding, and microbial pathogens. In addition, chs expression may be tissue-preferred, occurring in pigmented flowers and roots, and developmentally specific, occurring during early germination. (Ito et al., Mol. Gen. Gen. 255:28-37 (1997); Shimizu et al., Plant Molecular Biology 39(4)785-95 (1999))

Additional ipt gene/promoter constructions have been reported.

Smigocki et al., in WO 94/24848 and U.S. Pat. Nos. 5,496,732 and 5,792,934, disclosed a gene construct capable of conferring enhanced insect resistance comprising a wound-inducible promoter fused to an ipt gene. The study was focused on insect resistance and did not report changes in plant morphology.

Houck et al., in U.S. Pat. Nos. 4,943,674 and 5,177,307, disclosed several promoters (2AII, Z130 and Z70) coupled with genes encoding enzymes in the cytokinin metabolic pathway, in particular ipt for expression of such enzymes in tomato fruit.

Amasino et al., in PCT Patent Application Publication WO96/29858 disclosed two senescence-specific promoters, including SAG12, operably linked to an ipt gene to inhibit leaf senescence in tobacco. Transformants developed normally, with enhanced biomass and flower and seed production, perhaps owing to the extended developmental period created by the delay in senescence. See also: U.S. Pat. Nos. 5,689,042 and 6,359,197; Gan, S. et al., (*Science* 270:1986-1988 (1995)). Jordi et al., *Plant, Cell and Environment* 23(3): 279-289 (2000), studied the physiological effects of the SAG12:ipt construct in tobacco. While older leaves benefited by retaining chlorophyll, Rubisco, and protein, remobilization of nutrients from older leaves to younger leaves may have been reduced, leading to limited photosynthesis in the upper leaves and restricting potential increases in biomass of these plants, particularly under stress conditions.

Roeckel, P. et al., (*Transgenic Res*. 6(2):133-141 (1997)) transformed canola and tobacco with an ipt gene under the control of the developmentally-regulated, seed-specific 2S albumin promoter from *Agrobacterium*. While ipt mRNA was found only in seeds, and cytokinin levels were evaluated only in seeds, effects of the construct were not limited to seeds: tobacco had reduced roots; canola plants were "surprisingly" (p. 139) taller and had more branches and more seed-bearing structures. However, yield was not affected, nor was leaf type, leaf number, days to first flower, or days to bolting, in either species.

Transformation of tobacco with ipt linked to a copper-inducible, root-specific promoter provided, in 28 of 31 cases, a controlled system for evaluating effects of increased cytokinin production. Morphological changes upon induction included release of apical dominance, increases in total plant leaf number, and delay of leaf senescence. (McKenzie et al., *Plant Physiol*. 116:969-977 (1998)) Several transgenic lines, however, exhibited uncontrolled cytokinin expression and a radically different, undesirable phenotype, lacking root development and elongation of stems.

Ivic et al. (*Plant Cell Reports* 20:770-773 (2001)) reported that expression of ipt in transgenic sugarbeet resulted in severe inhibition of root development, along with undesirable changes in leaf and shoot morphology. Transformed plantlets formed roots slowly or not at all and had a very low survival rate when transferred to soil.

Sa et al. (Transgenic Research 11(3):269-278, 2002) reported that transformation of tobacco with ipt from *Agrobacterium* under the control of a TA29 promoter, which specifically expresses in anthers, resulted in perturbation in the development of anthers and pollen. About 80% of the T0 transgenic plants exhibited a significant decrease in the rate of pollen germination, and up to 20% of the T0 transgenic plants were male-sterile. In addition, abnormal styles and stamens were found in the transgenic plants.

Such negative effects resulting from directed expression of transgenic IPT were noted in PCT Publication WO 00/52169: "These approaches also produce undesirable side-effects in the plant and, even in cases where ipt or roIC is expressed under the control of tissue-specific promoters, these side-effects are observed in other tissues, presumably because the cytokinin is transported readily between cells and tissues of the plant." (emphasis added)

Thus, there still exists a need for nucleic acid constructs and methods useful in controlling and directing temporally- and spatially-regulated expression of cytokinin metabolic genes in plants, including plant seed and those maternal tissues in which seed development takes place, or in modulating plant sensing of and/or response to cytokinins, in order to improve plant vigor and yield without such detrimental effects as reduced root development or aberrant shoot morphology. This invention provides several such useful nucleic acid constructs and methods to modulate cytokinin activity in plants, including effective levels of cytokinin in plant seeds, developing plant seeds, and related maternal reproductive tissues. Further, the need exists for constructs and methods which can provide said improvements in plant vigor and yield under favorable or unfavorable growing conditions. This invention provides tools and reagents that allow the skilled artisan, by the application of, inter alia, transgenic methodologies, to so influence the level of cytokinin activity, including the metabolic flux in respect to the cytokinin metabolic pathway in seed. This influence may be either anabolic or catabolic, by which is meant the influence may act to increase the biosynthesis of cytokinin and/or decrease the degradation. A combination of both approaches is also contemplated by this invention. Further combinations may include targeted modulation of expression of isolated polynucleotides encoding polypeptides involved in cytokinin recognition and cellular response to provide enhanced cytokinin activity as defined herein.

SUMMARY OF THE INVENTION

Certain embodiments of the present invention provide plants, particularly transgenic maize, which have enhanced cytokinin activity, relative to an otherwise isogenic plant, without corresponding detrimental effects. Said enhancement relative to an otherwise isogenic plant may occur under favorable environmental conditions, unfavorable environmental conditions, or both. Enhanced cytokinin activity may encompass levels of cytokinins in the seed, the developing seed, and the maternal tissues associated with seed development. Alternatively or additionally, enhanced cytokinin activity may result from improved perception of, and response to, cytokinins by said plant. Enhanced cytokinin activity may act as a metabolic buffer to ameliorate the effects of transient stresses, particularly during the lag phase of seed development, to thus improve corn stress tolerance and yield stability. Enhanced cytokinin activity may also be manifested in improved plant vigor and/or increased seed yield. Such embodiments comprise a nucleic acid construct stably integrated into the genome thereof, said construct capable of the temporally- or spatially-regulated modulation of cytokinin levels.

Certain embodiments of the present invention provide transgenic plant lines with heritable phenotypes which are useful in breeding programs designed to produce commercial products with improved performance, which may include plant vigor, improved seed size, decreased tip kernel abortion and/or increased seed set during favorable or unfavorable environmental conditions. Such commercial products are further embodiments of the invention.

Some embodiments of the invention provide a fertile transgenic plant comprising a nucleic acid construct stably integrated into the genome thereof, said construct capable of effecting modulation of cytokinin activity in said plant.

Certain embodiments of the invention provide an isolated recombinant DNA molecule comprising a promoter directing temporally- or spatially-regulated expression of an operably-linked cytokinin-modulating gene and optionally comprising one or more enhancer elements from a highly-expressed gene.

In some embodiments the invention provides a method for improving stress tolerance and yield stability in plants, comprising stably introducing into plant cells a nucleic acid construct capable of effecting modulation of cytokinin activity, and from said cells, regenerating said plants with improved stress tolerance and yield stability. Said construct may result in preferential expression of cytokinin modulating genes during the lag phase of plant seed development.

Embodiments also provide a method for producing fertile, transgenic plants capable of the regulated expression of a cytokinin modulating gene in developing seeds, comprising introducing into plant host cells a nucleic acid construct capable of preferential temporal and/or spatial expression of a cytokinin-modulating gene in developing seed and the maternal tissues associated with seed development, under conditions sufficient for the stable integration of the construct into the genome of said cells, and regenerating and recovering said fertile transgenic plants.

Further embodiments of the invention provide a method for producing fertile, transgenic plants with enhanced vigor, comprising introducing into plant host cells a nucleic acid construct capable of effecting modulation of cytokinin activity, under conditions sufficient for the stable integration of said construct into the genome of said cells, and regenerating and recovering said fertile transgenic plants.

In accordance with these aspects of the invention, there are provided isolated nucleic acid molecules encoding cytokinin metabolic enzymes, including mRNAs, cDNAs, genomic DNAs and biologically useful variants, analogs or derivatives thereof, including fragments of the variants, analogs and derivatives. Other embodiments of the invention are naturally occurring allelic variants of the nucleic acid molecules in the sequences provided which encode cytokinin metabolic enzymes. Also provided are polypeptides that comprise cytokinin metabolic enzymes as well as biologically or diagnostically useful fragments thereof, as well as variants, derivatives and analogs of the foregoing and fragments thereof. For example, specifically provided are cytokinin metabolic polypeptides, particularly ipt (for example, SEQ ID NOS: 1 and 2) and cytokinin oxidase (for example, SEQ ID NOS: 26-37), that may be employed for modulation of cytokinin levels in seed and related female reproductive tissues, particularly meristematic regions of female reproductive tissues.

Certain embodiments of the invention provide methods for producing the polypeptides of interest, comprising culturing host cells having expressibly incorporated therein a polynucleotide under conditions for the temporal and/or spatial expression of cytokinin metabolic enzymes in seed and related female reproductive tissues, and then optionally recovering the expressed polypeptide.

Also provided in certain embodiments are probes that hybridize to cytokinin metabolic enzyme polynucleotide sequences useful as molecular markers in breeding programs.

Other embodiments of the invention provide products, compositions, processes and methods that utilize the aforementioned polypeptides and polynucleotides for research, biological and agricultural purposes.

Other embodiments of the invention provide inhibitors to such polypeptides, useful for modulating the activity and/or expression of the polypeptides. In particular, there are provided antibodies against such polypeptides.

In certain embodiments of this aspect of the invention there are provided antibodies against the cytokinin catabolic enzymes. The antibodies may be selective for the entire class of the cytokinin catabolic enzymes, irrespective of species of origin, as well as species-specific antibodies.

Yet other embodiments provide cytokinin enzyme antagonists and agonists. Among preferred antagonists are those which bind to cytokinin catabolic enzymes (e.g., to cytokinin oxidase) so as to inhibit the binding of binding molecules, or to destabilize the complex formed between the cytokinin catabolic enzyme and the binding molecule, to prevent further biological activity arising from the cytokinin catabolic enzyme. Among preferred agonists are molecules that bind to or interact with cytokinin biosynthetic enzymes so as to stimulate one or more effects of a particular cytokinin biosynthetic enzyme or which enhance expression of the enzyme and which also preferably result in a modulation of cytokinin accumulation.

Effective constructs result in cytokinin modulation within meristematic tissues, particularly those within female reproductive tissues, providing the observed improvement in vigor. The invention encompasses the particular constructs described herein, and other such constructs which may provide expression of cytokinin-modulating genes to result in improved plant vigor without significant detrimental effects. In any case, and without being limited to any particular theory, the modulation of cytokinin activity in the female reproductive tissues of said plant, to result in enhanced plant vigor without significant detrimental effects, is claimed.

Expression of isolated DNA sequences in a plant host is dependent upon the presence of operably linked regulatory elements that are functional within the plant host. Choice of the regulatory sequences will determine when and where within the organism the isolated DNA sequence is expressed. Where continuous expression is desired in all or nearly all cells of a plant throughout development, constitutive promoters are utilized. In contrast, where gene expression in response to a stimulus is desired, inducible promoters are the regulatory element of choice. Where expression in particular tissues or organs is desired, sometimes at specific stages of development, tissue-preferred promoters and/or terminators are used. That is, these regulatory elements can drive expression in specific tissues or organs, at specific stages. Additional regulatory sequences upstream and/or downstream from the core sequences can be included in expression cassettes of transformation vectors to bring about varying levels of expression of isolated nucleotide sequences in a transgenic plant.

Seed development involves embryogenesis and maturation events as well as physiological adaptation processes that occur within the seed to insure progeny survival. Developing plant seeds accumulate and store carbohydrate, lipid, and protein that are subsequently used during germination. Generally, the expression patterns of seed proteins are highly regulated. This regulation includes spatial and temporal regulation during seed development. A variety of proteins accumulate and decay during embryogenesis and seed development and provide an excellent system for investigating different aspects of gene regulation as well as for providing regulatory sequences for use in genetic manipulation of plants.

As the field of plant bioengineering develops, and more genes become accessible, a greater need exists for transforming with multiple genes. These multiple exogenous genes typically need to be controlled by separate regulatory sequences. Some genes should be regulated constitutively, whereas other genes should be expressed at certain developmental stages or locations in the transgenic organism. Accordingly, a variety of regulatory sequences having diverse effects are needed.

Another reason diverse regulatory sequences are needed is that undesirable biochemical interactions may result from using the same regulatory sequence to control more than one gene. For example, transformation with multiple copies of a regulatory element may cause homologous recombination between two or more expression systems, formation of hairpin loops resulting from two copies of the same promoter or enhancer in opposite orientation in close proximity, competition between identical expression systems for binding to common promoter-specific regulatory factors, and inappropriate expression levels of an exogenous gene due to trans effects of a second promoter or enhancer.

In view of these considerations, a goal in this field has been the detection and characterization of new regulatory sequences for transgenic control of DNA constructs.

Isolation and characterization of seed-preferred promoters and terminators that can serve as regulatory elements for expression of isolated nucleotide sequences of interest in a seed-preferred manner are needed for improving seed traits in plants. In particular, early kernel development is a stage critical in drought-induced ear tip abortion. Maintaining an active pool of plant cytokinins has been proven critical in sustaining kernel growth and development under transient drought stress. In addition, genes that contribute to stress responses in general, such as those involved in ABA responses, and also genes that maintain cell expansion and division, play essential roles in reproductive development under stress. Early stage endosperm has emerged as an important target tissue for transgene expression as it surrounds and nurtures developing embryos. EEP1 and EEP2 promoters address the need for directing transgene expression in the early endosperm tissue.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1A-E*mbryo*: This Figure shows that embryo-preferred overexpression of ipt increases embryo cytokinin levels, particularly ZR and Z9G (range of 2 to 8-fold difference). In contrast, Z levels are unchanged and IPAR is not detectable at either developmental stage. Abbreviations: Z=zeatin, ZR (or [9R]Z)=zeatin riboside, Z9G (or [9G]Z)=zeatin-9-glucoside, IPA or [9R]iP=isopentenyladenosine, IPAR (or [9R-5'P] iP)=isopentenyladenosine-5'-monophosphate, and DAP=Days After Pollination.

FIG. 1B-E*ndosperm*: This Figure shows that embryo-preferred ipt overexpression altered endosperm cytokinin levels but less than those in the embryo (range of only 10 to 30% difference). Abbreviations used as in FIG. 1A.

FIG. 10 shows increased plant biomass for event TC15850.

Figure 1A:
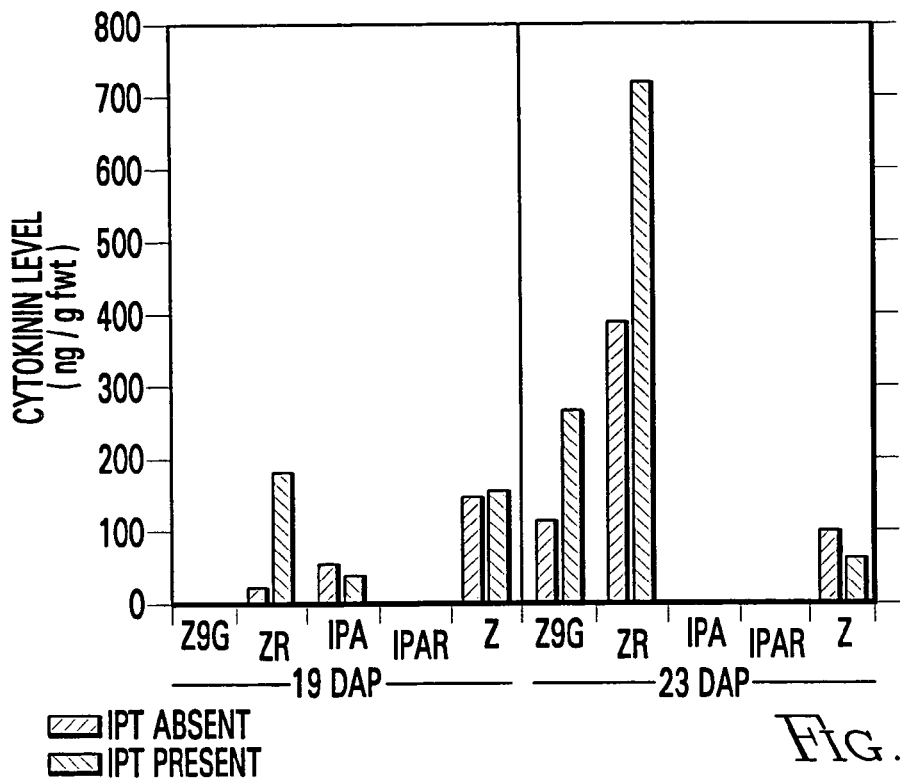

| | Sequence Listing Description |
|---|---|
| 1 | Agro ipt (pnt) |
| 2 | Agro ipt (ppt) |
| 3 | zag2.1 |
| 4 | CaMV35s enhancer |
| 5 | ZmMADS = ZAP |
| 6 | promoter ckx1-2 |
| 7 | eep1 |
| 8 | end2 |
| 9 | lec1 |
| 10 | F3.7 promoter |
| 11 | GSP1 primer for eep1 |
| 12 | GSP 2 primer for eep1 |
| 13 | Primer for eep1 |
| 14 | Primer for eep1 |
| 15 | Clontech AP1 primer |
| 16 | Clontech AP2 primer |
| 17 | tb1 promoter |
| 18 | eep2 promoter |
| 19 | trx1 or thxH promoter (thioredoxin H) |
| 20 | Zm40 promoter |
| 21 | GSP 1 primer for eep2 |
| 22 | GSP2 primer for eep2 |
| 23 | mLIP15 |
| 24 | ESR promoter |
| 25 | PCNA2 promoter |
| 26 | ZmCkx2 pnt |
| 27 | ZmCkx2 ppt |
| 28 | ZmCkx3 pnt |
| 29 | ZmCkx3 ppt |
| 30 | ZmCkx4 pnt |
| 31 | ZmCkx4 ppt |
| 32 | ZmCkx5 pnt |
| 33 | ZmCkx5 ppt |
| 34 | ZmCkx2 promoter |
| 35 | ZmCkx3 promoter |
| 36 | ZmCkx4 promoter |
| 37 | ZmCkx5 promoter |
| 38 | Primer for ipt gene isolation |
| 39 | Primer for ipt gene isolation |

GLOSSARY

The following illustrative explanations are provided to facilitate understanding of certain terms used frequently herein, particularly in the Examples. The explanations are provided as a convenience and not to limit the invention.

CYTOKININ ACTIVITY, as used herein, encompasses levels of active cytokinins within a plant, as well as the plant's perception of and response to cytokinins. Thus, cytokinin biosynthetic enzymes and cytokinin degrading enzymes are examples of enzymes capable of modulating cytokinin activity. "Cytokinin-modulating genes" comprises polynucleotides encoding such enzymes as well as polynucleotides encoding proteins involved in cytokinin perception and plant response, including transcription factors associated with the cytokinin response. The "active cytokinin pool" refers to the accumulation of active cytokinins at any one time within a cell or plant part or entire plant, as appropriate. Stabilizing the active cytokinin pool may involve down-regulation of cytokinin degradation or conjugation, or up-regulation of cytokinin biosynthesis.

CYTOKININ METABOLIC ENZYME-BINDING MOLECULE, as used herein, refers to molecules or ions which bind or interact specifically with cytokinin metabolic enzyme polypeptides or polynucleotides of the present invention, including, for example enzyme substrates, cell membrane components and classical receptors. Binding between polypeptides of the invention and such molecules, including binding or interaction molecules, may be exclusive to polypeptides of the invention, or it may be highly specific for polypeptides of the invention, or it may be highly specific to a group of proteins that includes polypeptides of the invention, or it may be specific to several groups of proteins at least one of which includes a polypeptide of the invention. Binding molecules also include antibodies and antibody-derived reagents that bind specifically to polypeptides of the invention.

CYTOKININ RESPONSIVE COMPONENT, as used herein, generally means a cellular constituent that binds to or otherwise interacts with a cytokinin resulting in the transmission of an intra- or inter-cellular signal and eliciting one or more cellular responses to the presence or absence or fluctuation in the levels of cytokinins.

DEVELOPING PLANT SEEDS, as used herein, generally means the maternal plant tissues which after pollination are capable of giving rise to a plant seed. This maternal plant tissue includes such tissue as female florets, ovaries, aleurone, pedicel, and pedicel-forming region.

DETRIMENTAL effects, as generally understood and as used herein, are those which are obviously harmful or damaging. Significant detrimental effects, in the context of this application, refer to phenotypic changes which would contribute to a net negative effect on plant productivity or vigor.

GENE SILENCING refers to posttranscriptional interference with gene expression. Techniques such as antisense, co-suppression, and RNA interference (RNAi), for example, have been shown to be effective in gene silencing. (For reviews, see Arndt and Rank, Genome 40(6):785-797, 1997; Turner and Schuch, Journal of Chemical Technology and Biotechnology 75(10):869-882, 2000; Klink and Wolniak, Journal of Plant Growth Regulation 19(4):371-384, 2000)

GENETIC ELEMENT, as used herein, generally means a polynucleotide comprising a region that encodes a polypeptide, or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

GERMPLASM, as used herein, means a set of genetic entities, which may be used in a breeding program to develop new plant varieties.

HIGH CYTOKININ TRANSGENIC, as used herein, means an entity, which, as a result of recombinant genetic manipulation, produces seed with a heritable increase in cytokinin and/or decrease in auxin.

HOST CELL, as used herein, is a cell which has been transformed or transfected, or is capable of transformation or transfection by an exogenous polynucleotide sequence. "Exogenous polynucleotide sequence" is defined to mean a sequence not naturally in the cell, or which is naturally present in the cell but at a different genetic locus, in different copy number, or under direction of a different regulatory element.

IDENTITY and SIMILARITY, as used herein, and as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity or similarity between two sequences include, but are not limited to those disclosed in Carillo, H., and Lipman, D., SIAM *J. Applied Math.*, 48:1073 (1988). Preferred methods to determine identity are designed to give the largest match between the two sequences tested. Methods to determine identity and similarity are codified in computer programs. Typical computer program methods to determine identity and similarity between two sequences include: GCG® program package (Accelrys, Inc., San Diego, Calif.; Devereux, J., et al, *Nucleic Acids Research* 12(1):387 (1984)), BLASTP, BLASTN, FASTA and TFASTA (Atschul, S. F. et al., *J. Mol. Biol.* 215:403 (1990)).

ISOLATED, as used herein, means altered "by the hand of man" from its natural state; i.e., that, if it occurs in nature, it has been changed or removed from its original environment, or both. For example, a naturally-occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally-occurring form or environment. Similarly, the polynucleotides and polypeptides may occur in a composition, such as media formulations or solutions for introduction into cells, or compositions or solutions for chemical or enzymatic reactions, which are not naturally occurring compositions, and, therein such polynucleotides or polypeptides remain isolated within the meaning of that term as it is employed herein.

LIGATION, as used herein, refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., *MOLECULAR CLONING, A LABORATORY MANUAL*, 2nd Ed.; Cold Spring Harbor Laboratory Press, Cold Spring Harbor, N.Y. (1989) and Maniatis et al., pg. 146, as cited below.

LOW-LEVEL CONSTITUTIVE EXPRESSION refers to gene expression in essentially all tissues of a plant and at most or all stages of development, at a level less than that of a gene driven by the CaMV35S promoter. Low-level constitutive expression of a polynucleotide may result from operable linkage to a promoter that normally drives such expression, such as F3.7 (SEQ ID NO: 10) or from a combination of a promoter operably linked to a gene the combination of which is further in proximity to an enhancer element, such as the CaMV35s enhancer. (See, for example, Mol. Gen. Gen. 261:635-643 (1999)) Promoters driving expression preferentially in meristematic tissues, such as zag2.1 (SEQ ID NO: 3), may also provide a low level of constitutive expression.

OLIGONUCLEOTIDE(S), as used herein, refers to short polynucleotides. Often the term refers to single-stranded deoxyribonucleotides, but it can refer as well to single- or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and expression of DNAs in cells and organisms. Initially, chemically-synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically-synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

OPERABLY LINKED, as used herein, includes reference to a functional linkage between a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

PLANT, as used herein, includes reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants, including, for example, maize, soybean, and canola.

PLASMIDS, as used herein, generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well-known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent from the present disclosure to those of skill.

POLYNUCLEOTIDE(S), as used herein, generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically-, enzymatically- or metabolically-modified forms of polynucleotides, as well as the chemical forms of DNA and RNA characteristic of viruses and cells, including inter alia, simple and complex cells.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally-occurring amino acids, and that many amino acids, including the terminal amino acids, may be modified in a given polypeptide, not only by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS—STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1-12 in *POSTTRANSLATIONAL COVALENT MODIFICATION OF PROTEINS*, B. C. Johnson, Ed., Academic Press, New York (1983); Seifter et al., *Meth. Enzymol.* 182:626-646 (1990) and Rattan et al., *Protein Synthesis: Posttranslational Modifications and Aging, Ann. N.Y. Acad. Sci.* 663:48-62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing events and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell post-translational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized by expressing a polynucleotide in a host cell.

PROMOTER, as used herein, includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells, such as *Agrobacterium* or *Rhizobium*. Examples of promoters under developmental control include promoters that preferentially initiate transcription in certain tissues, such as leaves, roots, or seeds or spatially in regions such as endosperm, embryo, or meristematic regions. Such promoters are referred to as "tissue-preferred". Promoters that initiate transcription only in certain tissue are referred to as "tissue-specific". A temporally regulated promoter drives expression at particular times, such as between 0-25 days after pollination. A "cell-type-preferred" promoter primarily drives expression in certain cell types in one or more organs, for example, vascular cells in roots or leaves. An "inducible" promoter is a promoter that is under environmental control and may be inducible or de-repressible. Examples of environmental conditions that may effect transcription by inducible promoters include anaerobic conditions or the presence of light. Tissue-specific, tissue-preferred, cell-type-specific, and inducible promoters constitute the class of "non-constitutive" promoters. A "constitutive" promoter is a promoter that is active under most environmental conditions and in all or nearly all tissues, at all or nearly all stages of development.

RECOMBINANT EXPRESSION CASSETTE, as used herein, refers to a nucleic acid construct, generated recombinantly or synthetically, with a series of specified genetic elements that permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter, and may optionally comprise additional elements, such as an enhancer.

RELATED FEMALE REPRODUCTIVE TISSUE, as used herein, includes maternal plant tissues, such as female florets, ovaries, aleurone, pedicel, and pedicel-forming region, either pre-pollination or upon pollination. Pre-pollination seed tissues can also be referred to as "grain initials" or "seed initials".

TRANSFORMATION, as used herein, is the process by which a cell is "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to higher eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. With reference to polynucleotides, generally, differences are limited such that the nucleotide sequences of the reference and the variant are closely similar overall and, in many regions, identical. As noted below, changes in the nucleotide sequence of the variant may be silent; that is, they may not alter the amino acids encoded by the polynucleotide. Where alterations are limited to silent changes of this type, a variant will encode a polypeptide with the same amino acid sequence as the reference. In other cases, as noted below, changes in the nucleotide sequence of the variant may alter the amino acid sequence of a polypeptide encoded by the reference polynucleotide. Such nucleotide changes may result in one or more amino acid substitutions, additions, deletions, fusions and truncations in the polypeptide encoded by the reference sequence, as discussed below. With reference to variant polypeptides generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

VIGOR of a plant, as used herein, refers to the relative health, productivity, and rate of growth of the plant and/or of certain plant parts, and may be reflected in various developmental attributes, including, but not limited to, concentration of chlorophyll, photosynthetic rate, total biomass, root biomass, grain quality, and/or grain yield. In *Zea mays* in particular, vigor may also be reflected in ear growth rate, ear size, and/or expansiveness of silk exsertion. Vigor may be determined with reference to different genotypes under similar environmental conditions, or with reference to the same or different genotypes under different environmental conditions.

YIELD STABILITY, as known in the art and as used herein, refers to consistent yield performance of a given genotype across environments, including environments of stress.

DETAILED DESCRIPTION OF THE INVENTION

This invention relates, in part, to nucleic acid constructs useful for modulation of cytokinin activity in plants, including the temporal and/or spatial expression of cytokinin genes in seed and related female reproductive tissue, and to associated polynucleotides and polypeptides; variants and derivatives of these polynucleotides and polypeptides; processes for making these polynucleotides and these polypeptides, and their variants and derivatives; agonists and antagonists of the polypeptides; products comprising these polynucleotides and polypeptides, and their variants and derivatives; and uses of these polynucleotides, polypeptides, variants, derivatives, agonists and antagonists, and uses of the products comprising same. In particular, in these and in other regards, the invention relates to polynucleotides and polypeptides of the cytokinin metabolic pathway, including the enzymes ipt and cytokinin oxidase and genes encoding same, and their use singly or in combination with each other and/or in combinations with various other isolated polynucleotides and polypeptides affecting cytokinin activity. Targeted modulation of expression to improve plant vigor and seed yield is described.

As mentioned above, the invention provides the reagents necessary for the development of transgenic plants characterized by enhanced cytokinin activity. As used herein, the phrase "cytokinin activity" is a relative one and refers to the cytokinin activity in a control plant without the cytokinin-affecting transgene as compared to a plant with such a functioning transgene. The relative levels may also be measured employing only the transgenic plant but measured in the presence and absence of expression of the subject transgene. Accordingly, any structural gene, the regulated expression of which has the effect of enhancing cytokinin activity in plants, particularly seeds, is useful for the practice of this invention. Genes that direct the expression of proteins that act to increase the biosynthesis of cytokinin (e.g., ipt or tzs) or genes encoding cytokinin degrading enzymes, the expression of which is inhibited, may be used in the practice of this invention. However, the use of other genes is also contemplated by this invention. In addition to genes that affect the absolute levels of cytokinin, genes that affect the ratio of cytokinin to auxin are also useful. Auxin-lowering genes such as iaa-1 and gene-5 may also be employed in the practice of this invention. Additionally or alternatively, targeted modulation of expression of isolated polynucleotides encoding polypeptides involved in cytokinin recognition and cellular reponse may provide enhanced cytokinin activity as defined herein. Combinations of these approaches, comprising changes in expression of one or more cytokinin-modulating genes, are also contemplated.

As mentioned above, the present invention relates to novel constructions of cytokinin metabolic polypeptides and polynucleotides encoding same, among other things, as described in greater detail below. The polypeptides particularly useful for the practice of this invention include, but are not limited to, ipt and cytokinin oxidase. The nucleic acids, and fragments thereof, encoding the above-mentioned enzymes are useful to generate enzyme-producing transgenics. For example, a single gene or gene fragment (or combinations of several genes) may be incorporated into an appropriate expression cassette (using for example the globulin-1 [glb1] promoter for embryo-preferred expression, or the 27 kd gamma zein promoter for endosperm-preferred expression in seed) and transformed into corn along with an appropriate selectable marker (such as the BAR and PAT genes). Certain embodiments comprise a promoter driving expression in female reproductive meristematic tissue operably linked to a poynucleotide encoding a cytokinin biosynthetic enzyme. Examples of promoters useful in such an embodiment include zag2.1, Zap (also known as ZmMADS), tb1, and PCNA2, as shown in SEQ ID NOS: 3, 5, 17, and 25.

In certain situations it may be preferable to silence or down-regulate certain genes, such as the cytokinin oxidase. Relevant literature describing the application of homology-dependent gene silencing include: Jorgensen, Trends Biotechnol. 8 (12):340-344 (1990); Flavell, Proc. Nat'l. Acad. Sci. (USA) 91:3490-3496 (1994); Finnegan et al., Bio/Technology 12: 883-888 (1994); Neuhuber et al., Mol. Gen. Genet. 244:230-241 (1994); Flavell et al. (1994) Proc. Natl. Acad. Sci. USA 91:3490-3496; Jorgensen et al. (1996) Plant Mol. Biol. 31:957-973; Johansen and Carrington (2001) Plant Physiol. 126:930-938; Broin et al. (2002) Plant Cell 14:1417-1432; Stoutjesdijk et al. (2002) Plant Physiol. 129:1723-1731; Yu et al. (2003) Phytochemistry 63:753-763; and U.S. Pat. Nos. 5,034,323, 5,283,184, and 5,942,657. Alternatively, another approach to gene silencing can be with the use of antisense technology (Rothstein et al. in Plant Mol. Cell. Biol. 6:221-246 (1989); Liu et al. (2002) Plant Physiol. 129:1732-1743 and U.S. Pat. Nos. 5,759,829 and 5,942,657. Methods and constructs for down-regulating expression of cytokinin oxidase are described in co-pending US provisional patent application, Cytokinin Oxidase-Like Sequences and Methods of Use, 60/559,252, filed Apr. 2, 2004.

Certain embodiments may comprise both increased cytokinin biosynthesis and reduced cytokinin degradation to result in improved cytokinin activity.

Polynucleotides

In accordance with one aspect of the present invention, there are provided the isolated polynucleotides of SEQ ID NOS: 26, 28, 30, and 32, which encode the cytokinin metabolic enzyme maize cytokinin oxidase, having the deduced amino acid sequences shown herein as SEQ ID NOS: 27, 29, 31, and 33, as disclosed in co-pending provisional application, Cytokinin Oxidase-Like Sequences and Methods of Use, 60/559,252, filed Apr. 2, 2004; as well as maize cytokinin oxidase of SEQ ID NO:38, encoding SEQ ID NO: 39, as disclosed in U.S. Pat. No. 6,229,066 and WO99/06571. Use of the isolated polynucleotide encoding ipt (isopentenyl transferase), as provided at Molecular and General Genetics 216:388-394 (1989) and provided herein as SEQ ID NO: 1, and its deduced amino acid sequence SEQ ID NO: 2, is also contemplated by this invention, as is use of other cytokinin biosynthetic genes (e.g., ipt) isolated from other organisms, such as Arabidopsis or maize, for example.

In accordance with one aspect of the present invention, there are provided the isolated Agrobacterium tumefaciens polynucleotide encoding isopentenyl transferase, SEQ ID NO: 1, and its deduced amino acid sequence, SEQ ID NO: 2 (Strabala, et al., Mol. Gen. Genet. 216, 388-394 (1989); GenBank Accession X14410); maize Zag2.1 promoter, SEQ ID NO: 3 (GenBank X80206); CaMV 35s enhancer, SEQ ID NO: 4; maize Zap promoter, SEQ ID NO: 5 (also known as ZmMADS; U.S. patent application Ser. No. 10/387,937; WO 03/078590); maize ckx1-2 promoter, SEQ ID NO: 6 (U.S. patent publication 2002-0152500 A1; WO 02/0078438); maize eep1 promoter, SEQ ID NO: 7 (U.S. provisional patent application 60/460,718); maize end2 promoter, SEQ ID NO: 8 (U.S. Pat. No. 6,528,704 and U.S. patent application Ser. No. 10/310,191); maize lec1 promoter, SEQ ID NO: 9 (U.S. patent application Ser. No. 09/718,754); maize F3.7 promoter, SEQ ID NO: 10 (Baszczynski et al., Maydica 42:189-201 (1997); maize tb1 promoter, SEQ ID NO: 17(Hubbarda et al., Genetics 162: 1927-1935, December 2002); maize eep2 promoter, SEQ ID NO: 18; maize thioredoxinH promoter, SEQ ID NO: 19, U.S. provisional Patent Application 60/514,123); maize Zm40 promoter, SEQ ID NO: 20 (U.S. Pat. No. 6,403,862 and WO 01/2178); maize mLIP15 promoter, SEQ ID NO: 23 (U.S. Pat. No. 6,479,734); maize ESR promoter, SEQ ID NO: 24 (U.S. application Ser. No. 10/786,679, filed Feb. 25, 2004); maize PCNA2 promoter, SEQ ID NO:25 (U.S. application Ser. No. 10/388,359 filed Mar. 13, 2003); maize cytokinin oxidases and promoters, SEQ ID NOS: 26-37 (co-pending provisional application, Cytokinin Oxidase-Like Sequences and Methods of Use, 60/559,252, filed Apr. 2, 2004).

The maize gene ZAG2 was isolated based on homology to the *Arabidopsis* AGAMOUS gene, which directs floral development. (Schmidt et al., Plant Cell 5(7):729-737, 1993) ZAG2 is normally expressed primarily in developing female florets. The ZAG2 coding sequence and approximately 2.1 kb of 5' sequence were deposited in GenBank as accession no. X80206 in September 1995. A portion of the ZAG2 5' region is included herein as SEQ ID NO: 3 and referred to as the ZAG2.1 promoter.

Using the information provided herein, such as the polynucleotide sequences set out below, a polynucleotide of the present invention encoding cytokinin metabolic enzyme polypeptides may be obtained using standard cloning and screening procedures. To obtain the polynucleotide encoding the protein using the DNA sequences given below, oligonucleotide primers can be synthesized that are complementary to the known polynucleotide sequence. These primers can then be used in PCR to amplify the polynucleotide from template derived from mRNA or genomic DNA isolated from the desired source material. The resulting amplified products can then be cloned into commercially available cloning vectors, such as the TA series of vectors from InVitrogen. By sequencing the individual clones thus identified with sequencing primers designed from the original sequence, it is then possible to extend the sequence in both directions to determine the full gene sequence. Such sequencing is performed using denatured double stranded DNA prepared from a plasmid clone. Suitable techniques are described by Maniatis, T., Fritsch, E. F. and Sambrook, J. in MOLECULAR CLONING, A Laboratory Manual (2nd edition 1989 Cold Spring Harbor Laboratory. See Sequencing Denatured Double-Stranded DNA Templates 13.70.

Isolation of ipt Gene:

The isopentenyl transferases (ipts) of the present invention may be obtained from sources including, but not limited to, *Zea mays, Agrobacterium, Psuedomonas savastano, Rhodococcus* and *Erwinia*. The complete sequence of an ipt gene is provided in Strabala, T. J., et al., *Isolation and characterization of an ipt gene from the Ti plasmid Bo*542, Mol. Gen. Genet. 216, 388-94 (1989). A copy of such gene can be prepared synthetically employing DNA synthesis protocols well known to those skilled in the art of gene synthesis. Alternatively, a copy of the gene may be isolated directly from an organism harboring an ipt gene, for example by PCR cloning as described in WO 00/63401, herein incorporated by reference.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the antisense strand.

The coding sequence that encodes the polypeptide may be identical to the coding sequence of the polynucleotides shown below. It also may be a polynucleotide with a different sequence, which, as a result of the redundancy (degeneracy) of the genetic code, encodes the polypeptides shown below. As discussed more fully below, these alternative coding sequences are an important source of sequences for codon optimization.

Polynucleotides of the present invention which encode the polypeptides listed below may include, but are not limited to, the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to, non-coding 5' and 3' sequences, such as the transcribed, non-translated sequences that play a role in transcription (including termination signals, for example), ribosome binding, mRNA stability elements, and additional coding sequences which encode additional amino acids, such as those which provide additional functionalities.

The DNA may also comprise promoter regions that function to direct the transcription of the DNA encoding heterologous cytokinin-modulating enzymes of this invention. Heterologous is defined as a sequence that is not naturally occurring with the promoter sequence. While the nucleotide sequence is heterologous to the promoter sequence, it may be homologous (native) or heterologous (foreign) to the plant host.

Furthermore, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.) and the pET series of vectors (Novagen), among others, many of which are commercially available. As described in Gentz et al., *Proc. Nat'l. Acad. Sci., (USA)* 86:821-824 (1989), for instance, hexa-histidine provides for convenient purification of the fusion protein. The HA tag may also be used to create fusion proteins and corresponds to an epitope derived of influenza hemagglutinin protein, which has been described by Wilson et al, *Cell* 37:767 (1984), for instance.

In accordance with the foregoing, the term "polynucleotide encoding a polypeptide" as used herein encompasses polynucleotides which include a sequence encoding a polypeptide of the present invention, particularly cytokinin modulating enzymes having the amino acid sequences set out below. The term encompasses polynucleotides that include a single continuous region or discontinuous regions encoding the polypeptide (for example, interrupted by integrated phage or insertion sequence or editing) together with additional regions that also may contain coding and/or non-coding sequences.

The present invention further relates to variants of the present polynucleotides that encode for fragments, analogs and derivatives of the polypeptides having the deduced amino acid sequence below. A variant of the polynucleotide may be a naturally occurring variant such as a naturally occurring allelic variant, or it may be a variant that is not known to occur naturally. Such non-naturally-occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions may involve one or more nucleotides. The variants may be altered in coding or non-coding regions or both. Alterations in the coding regions may produce conservative or non-conservative amino acid substitutions, deletions or additions.

Among the embodiments of the invention in this regard are polynucleotides encoding polypeptides having the amino acid sequences set out below; variants, analogs, derivatives and fragments thereof.

Further in this regard are polynucleotides encoding cytokinin biosynthetic enzyme variants, analogs, derivatives and fragments, and variants, analogs and derivatives of the fragments, which have the amino acid sequences below in which several, a few, 1 to 10, 1 to 5, 1 to 3, 2, 1 or no amino acid residues are substituted, deleted or added, in any combination. Among these are polynucleotides comprising silent substitutions, additions and deletions, which do not alter the properties and activities of the cytokinin biosynthetic enzymes; conservative substitutions; and polynucleotides encoding polypeptides having the amino acid sequence below, without substitutions.

Further embodiments of the invention comprise polynucleotides that are greater than 79%, at least 80%, or at least 85% identical to a polynucleotide encoding a polypeptide having an amino acid sequence set out below, and polynucleotides that are complementary to such polynucleotides. Certain embodiments, moreover, are polynucleotides which encode polypeptides which retain substantially the same, or even exhibit a increase in, biological function or activity as compared to that of the mature polypeptide encoded by the polynucleotides set out below.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80% identity between the sequences.

The terms "stringent conditions" or "stringent hybridization conditions" include reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, often less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding cytokinin biosynthetic enzymes and to isolate cDNA and genomic clones of other genes that have a high sequence similarity to the genes. Such probes generally will comprise between about 15 and 50 bases.

The polynucleotides and polypeptides of the present invention may be employed as research reagents and materials for discovery of transgenic plants with modulated cytokinin activity. The polynucleotides of the invention that are oligonucleotides derived from the sequences below may be used as PCR primers in the process herein described to determine whether or not the genes identified herein in whole or in part are transcribed in cytokinin accumulating tissue.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences, may be an inactive form of the polypeptide. When prosequences are removed, such inactive precursors generally are activated.

Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to polypeptides that have the deduced amino acid sequences below. The polypeptide of the present invention may be a recombinant polypeptide, a natural polypeptide or a synthetic polypeptide. In certain embodiments it is a recombinant polypeptide.

The invention also relates to fragments, analogs and derivatives of these polypeptides. The terms "fragment," "derivative" and "analog", when referring to the polypeptides, mean a polypeptide which retains at least 90% of, at least 95% of, or essentially the same biological function or activity as such polypeptide. Thus, an analog includes a proprotein that can be activated by cleavage of the proprotein portion to produce an active mature polypeptide. Among the embodiments of the invention in this regard are polypeptides having the amino acid sequence of cytokinin modulating enzymes set out below, variants, analogs, derivatives and fragments thereof, and variants, analogs and derivatives of the fragments.

The fragment, derivative or analog of the polypeptides below may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be obtained by those of ordinary skill in the art, from the teachings herein.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and lie; interchange of the hydroxyl residues Ser and Thr, exchange of the acidic residues Asp and Glu, substitution between the amide residues Asn and Gin, exchange of the basic residues Lys and Arg; and replacements among the aromatic residues Phe, Tyr.

Further particularly preferred in this regard are variants, analogs, derivatives and fragments, and variants, analogs and derivatives of the fragments, having the amino acid sequences below, in which several, a few, 1 to 10, 1 to 5, 1 to 3, 2, 1 or no amino acid residues are substituted, deleted or added, in any combination. Especially preferred among these are silent substitutions, additions and deletions, which do not alter the properties and activities of the cytokinin biosynthetic enzymes. Also especially preferred in this regard are conservative substitutions. Most highly preferred are polypeptides having the amino acid sequences below without substitutions.

The polypeptides and polynucleotides of the present invention are preferably provided in an isolated form, and may be purified to homogeneity.

Vectors, Host Cells, Expression

The present invention also relates to vectors comprising the polynucleotides of the present invention, host cells that incorporate the vectors of the invention, and the production of polypeptides of the invention by recombinant techniques.

Vectors

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors, also may be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host, operably linked to the polynucleotide to be expressed. Appropriate trans-acting factors are supplied by the host, supplied by a complementing vector or supplied by the vector itself upon introduction into the host.

In certain preferred embodiments in this regard, the vectors provide for preferred expression. Such preferred expression may be inducible expression or temporally limited or restricted to predominantly certain types of cells or any combination of the above. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids and binaries used for *Agrobacterum*-mediated transformations. All may be used for expression in accordance with this aspect of the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Useful plant binary vectors include BIN19 and its derivatives available from Clontech.

These vectors are listed solely by way of illustration of the many commercially available and well-known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention, several of which are disclosed in more detail below.

In general, expression constructs will contain sites for transcription initiation and termination, and, in the transcribed region, a ribosome-binding site for translation. The coding portion of the mature transcripts expressed by the constructs will include a translation-initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination signals, among others. For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell et al., *Plant Mol. Biol.* 10:263-72 (1988), and an enhancer from an opine gene as described by Fromm et al., *Plant Cell* 1:977 (1989). The enhancer may affect the tissue-specificity and/or temporal specificity of expression of sequences included in the vector. For example, a construct may comprise the CaMV 35s enhancer (SEQ ID NO: 4) in a "head to head" orientation with respect to the zag2.1 promoter (SEQ ID NO: 3) driving ipt (SEQ ID NO: 1).

Termination regions also facilitate effective expression by ending transcription at appropriate points. Useful terminators for practicing this invention include, but are not limited to, pinII (See An et al., Plant Cell 1(1): 115-122 (1989)), glb1 (See Genbank Accession #L22345), gz (See gzw64a terminator, Genbank Accession #S78780), and the nos terminator from *Agrobacterium*.

Among known eukaryotic promoters suitable for generalized expression are the CMV immediate early promoter, the HSV thymidine kinase promoter, the early and late SV40 promoters, the promoters of retroviral LTRs, such as those of the Rous sarcoma virus ("RSV"), metallothionein promoters, such as the mouse metallothionein-I promoter and various plant promoters, such as globulin-1. When available, the native promoters of the cytokinin modulating enzyme genes may be used. Representatives of prokaryotic promoters include the phage lambda PL promoter, the *E. coli* lac, trp and tac promoters to name just a few of the well-known promoters.

With respect to plants, examples of seed-preferred promoters include promoters of seed storage proteins which express these proteins in seeds in a highly regulated manner (Thompson, et al.; *BioEssays*;. 10:108 (1989)), such as, for dicotyledonous plants, a bean β-phaseolin promoter, a napin promoter, a β-conglycinin promoter, and a soybean lectin promoter. For monocotyledonous plants, promoters useful in the practice of the invention include, but are not limited to, a maize 15 kD zein promoter, a 22 kD zein promoter, a 27 Kd γ-zein promoter (such as gzw64A promoter, see Genbank Accession #S78780), a waxy promoter, a shrunken-1 promoter, a globulin 1 promoter (See Genbank Accession # L22344), an ltp2 promoter (Kalla, et al., Plant Journal 6:849-860 (1994); U.S. Pat. No. 5,525,716), cim1 promoter (see U.S. Pat. No. 6,225,529) maize end1 and end2 promoters (See U.S. Pat. No. 6,528,704 and application Ser. No. 10/310,191, filed Dec. 4, 2002); nuc1 promoter (U.S. Pat. No. 6,407,315); Zm40 promoter (U.S. Pat. No. 6,403,862); eep1 (SEQ ID NO: 7) and eep2 (SEQ ID NO: 18); lec1 (U.S. patent application Ser. No. 09/718,754); thioredoxinH promoter (U.S. provisional patent application 60/514,123); mlip15 promoter (U.S. Pat. No. 6,479,734); PCNA2 promoter, SEQ ID NO: 25; and the shrunken-2 promoter. (Shaw et al., Plant Phys 98:1214-1216, 1992; Zhong Chen et al., PNAS USA 100:3525-3530, 2003) However, other promoters useful in the practice of the invention are known to those of skill in the art such as nucellain promoter (See C. Linnestad, et al, *Nucellain, A Barley Homolog of the Dicot Vacuolar—Processing Proteasem Is Localized in Nucellar Cell Walls*, Plant Physiol. 118:1169-80 (1998), kn1 promoter (See S. Hake and N. Ori, *The Role of knotted1 in Meristem Functions*, B8: INTERACTIONS AND INTERSECTIONS IN PLANT PATHWAYS, COEUR D'ALENE, IDAHO, KEYSTONE SYMPOSIA, Feb. 8-14, 1999, at 27.), and F3.7 promoter (Baszczynski et al., Maydica 42:189-201 (1997); SEQ ID NO: 10). Spatially acting promoters such as glb1, an embryo-preferred promoter; or gamma zein, an endosperm-preferred promoter; or a promoter active in the embryo-surrounding region (see U.S. patent application Ser. No. 10/786,679, filed Feb. 25, 2004), or BETL1 (See G. Hueros, et al., Plant Physiology 121:1143-1152 (1999) and Plant Cell 7:747-57 (June 1995)), are particularly useful, including promoters preferentially active in female reproductive tissues, and those active in meristematic tissues, particularly in meristematic female reproductive tissues.

The use of temporally-acting promoters is also contemplated by this invention. Promoters that act from 0-25 days after pollination (DAP) are preferred, as are those acting from 4-21, 4-12, or 8-12 DAP. In this regard, promoters such as cim1 and ltp2 are preferred. Promoters that act from -14 to 0 days after pollination can also be used, such as SAG12 (See WO 96/29858, Richard M. Amasino, published 3 Oct. 1996) and ZAG1 or ZAG2 (See R. J. Schmidt, et al., *Identification and Molecular Characterization of ZAG1, the Maize Homolog of the Arabidopsis Floral Homeotic Gene AGAMOUS*, Plant-Cell 5(7): 729-37 (July 1993). See also SEQ ID NO: 3).

Useful promoters include maize zag2.1 (SEQ ID NO: 3), Zap (SEQ ID NO: 5, also known as ZmMADS; U.S. patent application Ser. No. 10/387,937; WO 03/078590); maize tb1 promoter (SEQ ID NO: 17; see also Hubbarda et al., Genetics 162:1927-1935, 2002).

Examples of suitable promoters for generalized expression in plants are the promoter for the small subunit of ribulose-1,5-bis-phosphate carboxylase, promoters from tumor-inducing plasmids of *Agrobacterium tumefaciens*, such as the nopaline synthase and octopine synthase promoters, and viral promoters such as the cauliflower mosaic virus (CaMV) 19S and 35S promoters or the figwort mosaic virus 35S promoter.

It will be understood that numerous promoters not mentioned are suitable for use in this aspect of the invention, are well known and readily may be employed by those of skill in the manner illustrated by the discussion and the examples herein. For example, this invention contemplates using, when appropriate, the native cytokinin biosynthetic enzyme promoters to drive the expression of the enzyme in a recombinant environment.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing E. coli and other prokaryotes. Kanamycin and herbicide resistance genes (PAT and BAR) are generally useful in plant systems.

Selectable marker genes, in physical proximity to the introduced DNA segment, are used to allow transformed cells to be recovered by either positive genetic selection or screening. The selectable marker genes also allow for maintaining selection pressure on a transgenic plant population, to ensure that the introduced DNA segment, and its controlling promoters and enhancers, are retained by the transgenic plant.

Many of the commonly used positive selectable marker genes for plant transformation have been isolated from bacteria and code for enzymes that metabolically detoxify a selective chemical agent which may be an antibiotic or a herbicide. Other positive selection marker genes encode an altered target which is insensitive to the inhibitor.

An example of a selection marker gene for plant transformation is the BAR or PAT gene, which is used with the selecting agent bialaphos. Spencer et al., J. Theor. Appl'd Genetics 79:625-631 (1990). Another useful selection marker gene is the neomycin phosphotransferase II (nptII) gene, isolated from Tn5, which confers resistance to kanamycin when placed under the control of plant regulatory signals. Fraley et al, Proc. Nat'l Acad. Sci. (USA) 80:4803 (1983). The hygromycin phosphotransferase gene, which confers resistance to the antibiotic hygromycin, is a further example of a useful selectable marker. Vanden Elzen et al., Plant Mol. Biol. 5:299 (1985). Additional positive selectable marker genes of bacterial origin that confer resistance to antibiotics include gentamicin acetyl transferase, streptomycin phosphotransferase, aminoglycoside-3'-adenyl transferase and the bleomycin resistance determinant. Hayford et al., Plant Physiol. 86:1216 (1988); Jones et al., Mol. Gen. Genet. 210:86 (1987); Svab et al., Plant Mol. Biol. 14:197 (1990); Hille et al., Plant Mol. Biol. 7:171 (1986).

Other positive selectable marker genes for plant transformation are not of bacterial origin. These genes include mouse dihydrofolate reductase, plant 5-enolpyruvylshikimate-3-phosphate synthase and plant acetolactate synthase. Eichholtz et al, Somatic Cell Mol. Genet. 13:67 (1987); Shah et al., Science 233:478 (1986); Charest et al., Plant Cell Rep. 8:643 (1990).

Another class of useful marker genes for plant transformation with the DNA sequence requires screening of presumptively transformed plant cells rather than direct genetic selection of transformed cells for resistance to a toxic substance such as an antibiotic. These genes are particularly useful to quantitate or visualize the spatial pattern of expression of the DNA sequence in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase. Jefferson, Plant Mol. Biol. Rep. 5:387 (1987); Teeri et al., EMBO J. 8:343 (1989); Koncz et al., Proc. Nat'l Acad. Sci. (USA) 84:131 (1987); De Block et al., EMBO J. 3:1681 (1984). Another approach to the identification of relatively rare transformation events has been use of a gene that encodes a dominant constitutive regulator of the Zea mays anthocyanin pigmentation pathway(Ludwig et al, Science 247:449 (1990)).

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. The sequence may be inserted in a forward or reverse orientation. Procedures for restriction and ligation that can be used to this end are well known and routine to those of skill. Suitable procedures in this regard, and for constructing expression vectors using alternative techniques, which also are well known and routine to those of skill, are set forth in great detail in Sambrook et al., MOLECULAR CLONING, A LABORATORY MANUAL, 2nd Ed.; Cold Spring Harbor Laboratory Press, Cold Spring Harbor, N.Y. (1989).

A polynucleotide of the invention, encoding the heterologous structural sequence of a polypeptide of the invention, generally will be inserted into the vector using standard techniques so that it is operably linked to the promoter for expression. The polynucleotide will be positioned so that the transcription start site is located appropriately 5' to a ribosome binding site. The ribosome-binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signals appropriately disposed at the 3' end of the transcribed region may also be included in the polynucleotide construct.

The vector containing the appropriate DNA sequence as described elsewhere herein, as well as an appropriate promoter, and other appropriate control sequences, may be introduced into an appropriate host using a variety of well-known techniques suitable to expression therein of a desired polypeptide. The present invention also relates to host cells containing the above-described constructs. The host cell can be a higher eukaryotic cell, such as a plant cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al, MOLECULAR CLONING: A LABORATORY MANUAL, 2nd Ed., Cold Spring Harbor Laboratory Press, Cold Spring Harbor, N.Y. (1989).

Representative examples of appropriate hosts include bacterial cells, such as *streptococci, staphylococci, E. coli, streptomyces* and *Salmonella typhimurium* cells; fungal cells, such as yeast cells and *Aspergillus* cells; insect cells such as *Drosophila* S2 and *Spodoptera* Sf9 cells; animal cells such as CHO, COS and Bowes melanoma cells; and plant cells. The plant cells may be derived from a broad range of plant types, particularly monocots such as the species of the Family Graminiae including *Sorghum bicolor* and *Zea mays*, as well as dicots such as soybean (*Glycine max*) and canola (*Brassica napus, Brassica rapa* ssp.). Preferably, plants include maize, soybean, sunflower, safflower, canola, wheat, barley, rye, alfalfa, and sorghum; however, the isolated nucleic acid and proteins of the present invention can be used in species from the genera: *Ananas, Antirrhinum, Arabidopsis, Arachis, Asparagus, Atropa, Avena, Brassica, Bromus, Browaalia, Camellia, Capsicum, Ciahorium, Citrus, Cocos, Cofea, Cucumis, Cucurbita, Datura, Daucus, Digitalis, Ficus, Fragaria, Geranium, Glycine, Gossypium, Helianthus, Heterocallis, Hordeum, Hyoscyamus, Ipomoea, Juglans, Lactuca, Linum, Lolium, Lotus, Lycopersicon, Majorana, Mangifera, Manihot, Medicago, Musa, Nemesis, Nicotiana, Olea, Onobrychis, Oryza, Panieum, Pelargonium, Pennisetum, Persea, Petunia, Phaseolus, Pisum, Psidium, Ranunculus, Raphanus, Rosa, Salpiglossis, Secale, Senecio, Solanum, Sinapis, Sorghum, Theobroma, Triticum, Trifolium, Trigonella, Vigna, Vitis,* and *Zea.*

The promoter regions of the invention may be isolated from any plant, including, but not limited to, maize (corn; *Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include maize, soybean, sunflower, safflower, canola, wheat, barley, rye, alfalfa, and sorghum.

Hosts for a great variety of expression constructs are well known, and those of skill will be enabled by the present disclosure readily to select a host for expressing a polypeptide in accordance with this aspect of the present invention.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

Mature proteins can be expressed in mammalian cells, yeast, bacteria, or other cells under the control of appropriate promoters. Cell-free translation systems can also be employed to produce such proteins using RNAs derived from the DNA constructs of the present invention.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well know to those skilled in the art.

Plant Transformation Methods:

Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22: 421-477 (1988). For example, the DNA construct may be introduced directly into the genomic DNA of the plant cell using techniques such as electroporation, PEG poration, particle bombardment, silicon fiber delivery, or microinjection of plant cell protoplasts or embryogenic callus. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3: 2717-2722 (1984). Electroporation techniques are described in Fromm et al., *Proc. Natl. Acad. Sci* (USA) 82: 5824 (1985). Ballistic transformation techniques are described in Klein et al, *Nature* 327: 70-73 (1987) and by Tomes, D. et al., IN: Plant Cell, Tissue and Organ Culture: Fundamental Methods, Eds. O. L. Gamborg and G. C. Phillips, Chapter 8, pgs. 197-213 (1995). (See also Tomes et al., U.S. Pat. Nos. 5,886,244; 6,258,999; 6,570,067; 5,879,918)

*Agrobacterium tumefaciens*-meditated transformation techniques are well described in the scientific literature. See, for example Horsch et al., *Science* 233: 496-498 (1984), and Fraley et al., *Proc. Natl. Acad. Sci*(USA) 80: 4803 (1983). Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985),Application PCT/ US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25: 1353, 1984), (3) the vortexing method (see, e.g., Kindle, *Proc. Nat'l. Acad. Sci.*(*USA*) 87: 1228, (1990).

DNA can also be introduced into plants by direct DNA transfer into pollen as described by Zhou et al., *Methods in Enzymology*, 101:433 (1983); D. Hess, *Intern. Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature* 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo*. 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus.

Regeneration of Transformed Plants

Transformed plant cells that are derived by any of the above transformation techniques can be cultured to regenerate a whole plant that possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of maize see, for example, U.S. Pat. No. 5,736,369.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* from leaf explants can be achieved as described by Horsch et al., *Science*, 227:1229-1231 (1985). In this procedure, transformants are grown in the presence of a selection agent and in a medium that induces the regeneration of shoots in the plant species being transformed as described by Fraley et al., *Proc. Nat'l. Acad. Sci. (U.S.A).*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys*. 38: 467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed-propagated crops, mature transgenic plants can be self-crossed to produce a homozygous inbred plant. The inbred plant produces seed containing the newly introduced heterologous nucleic acid. These seeds can be grown to produce plants that would produce the selected phenotype. Mature transgenic plants can also be crossed with other appropriate plants, generally another inbred or hybrid, including, for example, an isogenic untransformed inbred.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these plants comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Some embodiments comprise a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous (aka hemizygous) transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant, or with a plant transgenic for the same or another trait or traits, are also contemplated.

It is also expected that the transformed plants will be used in traditional breeding programs, including TOPCROSS pollination systems as disclosed in U.S. Pat Nos. 5,706,603 and 5,704,160, the disclosure of each of which is incorporated herein by reference.

Polynucleotide Assays

This invention is also related to the use of the cytokinin biosynthetic enzyme polynucleotides in markers to assist in a breeding program, as described for example in PCT publication US89/00709. The DNA may be used directly for detection or may be amplified enzymatically by using PCR (Saiki et al., *Nature* 324:163-166 (1986)) prior to analysis. RNA or cDNA may also be used in the same ways. As an example, PCR primers complementary to the nucleic acid encoding the cytokinin biosynthetic enzymes can be used to identify and analyze cytokinin biosynthetic enzyme presence and expression. Using PCR, characterization of the gene present in a particular tissue or plant variety may be made by an analysis of the genotype of the tissue or variety. For example, deletions and insertions can be detected by a change in size of the amplified product in comparison to the genotype of a reference sequence. Point mutations can be identified by hybridizing amplified DNA to radiolabeled cytokinin biosynthetic enzyme RNA or alternatively, radiolabeled cytokinin biosynthetic enzyme antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide tags or by automatic sequencing procedures with fluorescent tags.

Genetic typing of various varieties of plants based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations also may be revealed by nuclease protection assays, such as RNase and S1 protection or the chemical cleavage method (e.g., Cotton et al., *Proc. Nat'l. Acad. Sci.*, (*USA*), 85:4397-4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP")) and Southern blotting of genomic DNA.

In addition to more conventional gel-electrophoresis and DNA sequencing, mutations also can be detected by in situ analysis.

A mutation may be ascertained, for example, by a DNA sequencing assay. Samples are processed by methods known in the art to capture the RNA. First strand cDNA is synthesized from the RNA samples by adding an oligonucleotide primer consisting of sequences that hybridize to a region on the mRNA. Reverse transcriptase and deoxynucleotides are added to allow synthesis of the first strand cDNA. Primer sequences are synthesized based on the DNA sequences of the cytokinin modulating enzymes of the invention. The primer sequence is generally comprised of at least 15 consecutive bases, and may contain at least 30 or even 50 consecutive bases.

Cells carrying mutations or polymorphisms in the gene of the present invention may also be detected at the DNA level by a variety of techniques. The DNA may be used directly for detection or may be amplified enzymatically by using PCR (Saiki et al., *Nature*, 324:163-166 (1986)) prior to analysis.

RT-PCR can also be used to detect mutations. It is particularly preferred to use RT-PCR in conjunction with automated detection systems, such as, for example, GeneScan. RNA or cDNA may also be used for the same purpose, PCR or RT-PCR. As an example, PCR primers complementary to the nucleic acid encoding cytokinin biosynthetic enzymes can be used to identify and analyze mutations. Examples of representative primers are shown below. For example, deletions and insertions can be detected by a change in size of the amplified product in comparison to the normal genotype. Point mutations can be identified by hybridizing amplified DNA to radiolabeled RNA, or alternatively, radiolabeled antisense DNA sequences. While perfectly matched sequences can be distinguished from mismatched duplexes by RNase A digestion or by differences in melting temperatures, preferably point mutations are identified by sequence analysis.

Primers used for detection of mutations or polymorphisms in the ipt gene:

```
                                            (SEQ ID NO: 40)
        5'GCGTCCAATGCTGTCCTCAACTA 3'

(SEQ ID NO: 41)
        5'GCTCTCCTCGTCTGCTAACTCGT 3'
```

The above primers may be used for amplifying cytokinin biosynthetic enzyme cDNA or genomic clones isolated from a sample derived from an individual plant. The invention also provides the primers above with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be identified.

Polypeptide Assays

The present invention also relates to diagnostic assays such as quantitative and diagnostic assays for detecting levels of cytokinin biosynthetic enzymes in cells and tissues, including determination of normal and abnormal levels. Thus, for instance, a diagnostic assay in accordance with the invention for detecting expression of cytokinin biosynthetic enzymes compared to normal control tissue samples may be used to detect unacceptable levels of expression. Assay techniques that can be used to determine levels of polypeptides of the present invention in a sample derived from a plant source are well-known to those of skill in the art. Such assay methods include radioimmunoassays, competitive-binding assays, Western Blot analysis and ELISA assays. Among these, ELISAs frequently are preferred. An ELISA assay initially comprises preparing an antibody specific to the polypeptide, preferably a monoclonal antibody. In addition, a reporter antibody generally is prepared which binds to the monoclonal antibody. The reporter antibody is attached to a detectable reagent such as a radioactive, fluorescent or enzymatic reagent, in this example horseradish peroxidase enzyme.

To carry out an ELISA, a sample is removed from a host and incubated on a solid support, e.g., a polystyrene dish, which binds the proteins in the sample. Any free protein binding sites on the dish are then covered by incubating with a non-specific protein such as bovine serum albumin. Next, the monoclonal antibody is incubated in the dish, during which time the monoclonal antibodies attach to any cytokinin biosynthetic enzymes attached to the polystyrene dish. Unbound monoclonal antibody is washed out with buffer. The reporter antibody linked to horseradish peroxidase is placed in the dish, resulting in binding of the reporter antibody to any monoclonal antibody bound to cytokinin biosynthetic enzyme. Unattached reporter antibody is then washed out. Reagents for peroxidase activity, including a colorimetric substrate, are then added to the dish. Immobilized peroxidase, linked to cytokinin biosynthetic enzyme through the primary and secondary antibodies, produces a colored reaction product. The amount of color developed in a given time period indicates the amount of cytokinin biosynthetic enzyme present in the sample. Quantitative results typically are obtained by reference to a standard curve.

A competition assay may be employed wherein antibodies specific to cytokinin biosynthetic enzymes are attached to a solid support, and labeled enzyme derived from the host ispassed over the solid support. The amount of label detected attached to the solid support can be correlated to a quantity of cytokinin biosynthetic enzyme in the sample.

Antibodies

The polypeptides, their fragments or other derivatives, or analogs thereof, or cells expressing them can be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal, or by administering the polypeptides to an animal, preferably a nonhuman. The antibody so obtained will then bind the polypeptides itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique that provides antibodies produced by continuous cell line cultures can be used. Examples include the hybridoma technique (Kohler, G. and Milstein, C., *Nature* 256:495-497 (1975)), the trioma technique, the human B-cell hybridoma technique (Kozbor et al., *Immunology Today* 4:72 (1983)) and the EBV-hybridoma technique to produce human monoclonal antibodies (Cole et al., pg. 77-96 in *MONOCLONAL ANTIBODIES AND CANCER THERAPY*, Alan R. Liss, Inc. (1985)).

Hybridoma cell lines secreting the monoclonal antibody are another aspect of this invention.

Techniques described for the production of single-chain antibodies (U.S. Pat. No. 4,946,778) can be adapted to produce single-chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or identify clones expressing the polypeptide or to purify the polypeptide of the present invention by attachment of the antibody to a solid support for isolation and/or purification by affinity chromatography.

Polypeptide derivatives include antigenically or immunologically equivalent derivatives that form a particular aspect of this invention.

The term 'antigenically equivalent derivative' as used herein encompasses a polypeptide or its equivalent which will be specifically recognized by certain antibodies which, when raised to the protein or polypeptide according to the present invention, interfere with the immediate physical interaction between the antibody and its cognate antigen.

The term "immunologically equivalent derivative" as used herein encompasses a peptide or its equivalent which, when used in a suitable formulation to raise antibodies in a vertebrate, results in antibodies which act to interfere with the immediate physical interaction between the antibody and its cognate antigen.

The polypeptide, such as an antigenically or immunologically equivalent derivative or a fusion protein thereof, is used as an antigen to immunize a mouse or other animal, such as a rat, guinea pig, goat, rabbit, sheep, bovine or chicken. The fusion protein may provide stability to the polypeptide. The antigen may be associated, for example by conjugation, with an immunogenic carrier protein, for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof, may be sufficiently antigenic to improve immunogenicity so as to obviate the use of a carrier.

Alternatively, phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), *Nature* 348:552-554; Marks, J. et al., (1992) *Biotechnology* 10:779-783). The affinity of these antibodies can also be improved by chain shuffling (Clackson, T. et al., (1991) *Nature* 352:624-628).

The antibody should be screened again for high affinity to the polypeptide and/or fusion protein.

As mentioned above, a fragment of the final antibody may be prepared.

The antibody may be either intact antibody of $M_r$ approximately 150,000 or a derivative of it, for example a Fab fragment or a Fv fragment as described in Sierra, A and Pluckthun, A., *Science* 240:1038-1040 (1988). If two antigen binding domains are present, each domain may be directed against a different epitope—termed 'bispecific' antibodies.

The antibody of the invention, as mentioned above, may be prepared by conventional means, for example by established monoclonal antibody technology (Kohler, G. and Milstein, C., *Nature*, 256:495-497 (1975)) or using recombinant means e.g. combinatorial libraries, for example as described in Huse, W. D. et al., *Science* 246:1275-1281 (1989).

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or *Streptomyces* sp. or a eukaryotic cell, such as a mouse C127, mouse myeloma, human HeLa, Chinese hamster ovary, filamentous or unicellular fungi or insect cell. The host may also be a transgenic animal or a transgenic plant for example as described in Hiatt, A. et al, *Nature* 340:76-78 (1989). Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.

Cytokinin Biosynthetic Enzyme Binding Molecules and Assays

This invention also provides a method for identification of molecules, such as binding molecules, that bind the cytokinin biosynthetic enzymes. Genes encoding proteins that bind the enzymes, such as binding proteins, can be identified by numerous methods known to those of skill in the art, for example, ligand panning and FACS sorting. Such methods are described in many laboratory manuals such as, for instance, Coligan et al., *Current Protocols in Immunology* 1(2): Chapter 5 (1991).

For instance, expression cloning may be employed for this purpose. To this end, polyadenylated RNA is prepared from a cell expressing the cytokinin biosynthetic enzymes, a cDNA library is created from this RNA, the library is divided into pools, and the pools are transfected individually into cells that are not expressing the enzyme. The transfected cells then are exposed to labeled enzyme. The enzyme can be labeled by a variety of well-known techniques, including standard methods of radio-iodination or inclusion of a recognition site for a site-specific protein kinase. Following exposure, the cells are fixed and binding of enzyme is determined. These procedures conveniently are carried out on glass slides.

Pools are identified of cDNA that produced cytokinin biosynthetic enzyme-binding cells. Sub-pools are prepared from these positives, transfected into host cells and screened as described above. Using an iterative sub-pooling and re-screening process, one or more single clones that encode the putative binding molecule can be isolated.

Alternatively, a labeled ligand can be photoaffinity linked to a cell extract, such as a membrane or a membrane extract, prepared from cells that express a molecule that it binds, such as a binding molecule. Cross-linked material is resolved by polyacrylamide gel electrophoresis ("PAGE") and exposed to X-ray film. The labeled complex containing the ligand-binding can be excised, resolved into peptide fragments, and subjected to protein microsequencing. The amino acid sequence obtained from microsequencing can be used to design unique or degenerate oligonucleotide probes to screen cDNA libraries to identify genes encoding the putative binding molecule.

Polypeptides of the invention also can be used to assess cytokinin biosynthetic enzyme binding capacity of cytokinin biosynthetic enzyme binding molecules, such as binding molecules, in cells or in cell-free preparations.

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics.

Anti-cytokinin biosynthetic enzyme antibodies represent a useful class of binding molecules contemplated by this invention.

Antagonists and Agonists—Assays and Molecules

The invention also provides a method of screening compounds to identify those that enhance or block the action of cytokinin biosynthetic enzymes on cells, such as interaction with substrate molecules. An antagonist is a compound that decreases the natural biological functions of the enzymes. A particular enzyme to be targeted in this regard is cytokinin oxidase.

Potential antagonists include small organic molecules, peptides, polypeptides and antibodies that bind to cytokinin oxidase and thereby inhibit or extinguish its activity. Potential antagonists also may be small organic molecules, a peptide, a polypeptide such as a closely related protein or antibody, that binds the same sites on a binding molecule, such as a cytokinin oxidase binding molecule, without inducing cytokinin metabolic enzyme-induced activities, thereby preventing the action of the enzyme by excluding the enzyme from binding.

Potential antagonists include a small molecule that binds to and occupies the binding site of the polypeptide thereby preventing binding to cellular binding molecules, such as binding molecules, such that normal biological activity is prevented. Examples of small molecules include but are not limited to small organic molecules, peptides or peptide-like molecules.

Other potential antagonists include molecules that affect the expression of the gene encoding cytokinin biosynthetic enzymes (e.g. transactivation inhibitors). Other potential antagonists include antisense molecules. Antisense technology can be used to control gene expression through antisense DNA or RNA or through double- or triple-helix formation. Antisense techniques are discussed, for example, in—Okano, J. Neurochem. 56: 560 (1991); *OLIGODEOXYNUCLE-OTIDES AS ANTISENSE INHIBITORS OF GENE EXPRESSION*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription, thereby preventing transcription and the production of cytokinin biosynthetic enzymes. The antisense RNA oligonucleotide hybridizes to the mRNA in vivo and blocks translation of the mRNA molecule into cytokinin biosynthetic enzymes. The oligonucleotides described above can also be delivered to cells such that the antisense RNA or DNA may be expressed in vivo to inhibit production of cytokinin biosynthetic enzymes.

The DNAs of this invention may also be employed to co-suppress or silence the cytokinin metabolic enzyme genes; for example, as described in PCT Patent Application Publication WO 98/36083.

The antagonists may be employed for instance to increase the levels of cytokinin and/or decrease the available auxin in plant cells.

Alternatively, this invention provides methods for screening for agonists, those molecules that act to increase the natural biological function of enzymes. Targets in this regard include enzymes such ipt, β-glucosidase, and iaa-1.

Potential agonists include small organic molecules, peptides, polypeptides and antibodies that bind to a biosynthetic enzyme and thereby stimulate or increase its activity. Potential agonists also may be small organic molecules, a peptide, a polypeptide such as a closely related protein or antibody that binds to sites on a binding molecule, such as a ipt binding molecule and promotes cytokinin metabolic enzyme-induced activities, thereby enhancing the action of the enzyme.

Potential agonists include small molecules that bind to and occupy the allosteric sites of the enzyme thereby promoting binding to cellular binding molecules, such as substrates, such that normal biological activity is enhanced. Examples of small molecules include but are not limited to small organic molecules, peptides or peptide-like molecules.

Other potential agonists include molecules that affect the expression of the gene encoding cytokinin biosynthetic enzymes (e.g. transactivatiors).

"Stacking" of Constructs and Traits

In certain embodiments the nucleic acid sequences of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression affecting cytokinin activity. For example, up-regulation of cytokinin synthesis may be combined with down-regulation of cytokinin oxidase expression. Other combinations may be designed to produce plants with a variety of desired traits, including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., Bacillus thuringiensis toxic proteins (U.S. Pat. Nos. 5,366,892; 5,747,450; 5,737,514; 5,723,756; 5,593,881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5.602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or over-expression cassettes to generate the desired combination of traits in the plant.

Use in Breeding Methods

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield, and better agronomic quality. With mechanical harvesting of many crops, uniformity of plant characteristics such as germination and stand establishment, growth rate, maturity, and plant and ear height, is desirable. Traditional plant breeding is an important tool in developing new and improved commercial crops. This invention encompasses methods for producing a maize plant by crossing a first parent maize plant with a second parent maize plant wherein one or both of the parent maize plants is a transformed plant displaying enhanced vigor, as described herein.

Plant breeding techniques known in the art and used in a maize plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular maize plant using transformation techniques, could be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant. As used herein, "crossing" can refer to a simple X by Y cross, or the process of backcrossing, depending on the context.

The development of a maize hybrid in a maize plant breeding program involves three steps: (1) the selection of plants from various germplasm pools for initial breeding crosses; (2)

the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

In accordance with the invention, nucleotide sequences are provided that allow initiation of transcription in seed. The sequences of the invention comprise transcriptional initiation regions associated with seed formation and seed tissues. Thus, the compositions of the present invention comprise novel nucleotide sequences for regulatory sequences.

A method for expressing an isolated nucleotide sequence in a plant using the transcriptional initiation sequences disclosed herein is provided. Suitable techniques are described by Maniatis, T., Fritsch, E. F. and Sambrook, J. in MOLECULAR CLONING, A Laboratory Manual (2nd edition 1989 Cold Spring Harbor Laboratory). The method comprises transforming a plant cell with a transformation vector that comprises an isolated nucleotide sequence operably linked to the promoter of the present invention and regenerating a stably transformed plant from the transformed plant cell. In this manner, the promoter is useful for controlling the expression of endogenous as well as exogenous products in a seed-preferred manner.

Under the transcriptional initiation regulation of the seed-preferred promoter region will be a sequence of interest, which will provide for modification of the phenotype of the seed. Such modification includes modulating the production of an endogenous product, as to amount, relative distribution, or the like, or production of an exogenous expression product to provide for a novel function or product in the seed.

By "seed-preferred" is intended favored expression in the seed, including at least one of embryo, kernel, pericarp, endosperm, nucellus, aleurone, pedicel, and the like.

By "regulatory element" is intended sequences responsible for tissue-preferred and temporally-preferred expression of the associated coding sequence, including promoters, terminators, enhancers, introns, and the like.

By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein is generally further defined by comprising upstream regulatory elements such as those responsible for tissue-preferred and temporally-preferred expression of the coding sequence, enhancers, and the like. In the same manner, the promoter elements that enable expression in the desired tissue such as the seed can be identified, isolated, and used with other core promoters to confirm seed-preferred expression.

The isolated promoter sequences of the present invention can be modified to provide for a range of expression levels of the isolated nucleotide sequence. Less than the entire promoter region can be utilized and the ability to drive seed-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

A promoter of the present invention can be isolated from the 5' untranslated region flanking the transcription initiation site of its respective coding sequence. Likewise, the terminator can be isolated from the 3' untranslated region flanking the stop codon of its respective coding sequence.

The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art. A sequence for the promoter region eep1 is set forth in SEQ ID NO: 7. A sequence for the promoter region eep2 is set forth in SEQ ID NO: 18.

The eep1 promoter set forth in SEQ ID NO: 7 is 960 nucleotides in length A putative CAAT motif is found 308 bp upstream of the start of translation and a putative TATA motif is found 139 bp upstream form the start of translation. The promoter was isolated from EST sequences found in maize tissue libraries of 4 and 6 DAP embryo sacs, as well as 5 and 7 DAP whole kernels. The eep1 promoter can address expression problems by providing expression in seed tissues during early stages of seed development.

The eep2 promoter set forth in SEQ ID NO: 18 is 1027 nucleotides in length. The promoter was isolated from an EST sequence found in maize tissue libraries of 4 DAP (days after pollination) embryo sacs and is highly specific for early kernel and endosperm expression, as determined by EST distribution among libraries and by Lynx MPSS profiling.

The promoter regions of the invention may be isolated from any plant, including, but not limited to, maize (corn; *Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea ameficana*), fig (*Ficus casica*), guava (*Psidium guajava*), mango (*Mangifera indica*), olive (*Olea europaea*), oats, barley, vegetables, ornamentals, and conifers. Preferably, plants include maize, soybean, sunflower, safflower, canola, wheat, barley, rye, alfalfa, and sorghum.

Promoter sequences from other plants may be isolated according to well-known techniques based on their sequence homology to the promoter sequences set forth herein. In these techniques, all or part of the known promoter sequence is used as a probe which selectively hybridizes to other sequences present in a population of cloned genomic DNA fragments (i.e. genomic libraries) from a chosen organism. Methods that are readily available in the art for the hybridization of nucleic acid sequences may be used to obtain sequences which correspond to the promoter of the present invention.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990) *PCR Protocols, A Guide to Methods and Applications*, eds., Academic Press).

In general, sequences that correspond to the promoter sequence of the present invention and hybridize to the promoter sequence disclosed herein will be at least 50% homologous, 55% homologous, 60% homologous, 65% homologous, 70% homologous, 75% homologous, 80% homologous, 85% homologous, 90% homologous, 95% homologous and even 98% homologous or more with the disclosed sequence.

The following terms are used to describe the sequence relationships between two or more nucleic acids or polynucleotides: (a) "reference sequence", (b) "comparison window", (c) "percentage of sequence identity", and (d) "substantial identity".

(a) As used herein, "reference sequence" is a defined sequence used as a basis for sequence comparison. A reference sequence may be a subset or the entirety of a specified sequence; for example, a segment of a full-length promoter sequence, or the complete promoter sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length and optionally can be 30, 40, 50, 100, or more contiguous nucleotides in length. Those of skill in the art understand that to avoid a high similarity to a reference sequence due to inclusion of gaps in the polynucleotide sequence a gap penalty is typically introduced and is subtracted from the number of matches.

(c) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

(d) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters.

Methods of aligning sequences for comparison are well known in the art. Gene comparisons can be determined by conducting BLAST (Basic Local Alignment Search Tool; Altschul, S. F., et al., (1993) *J. Mol. Biol.* 215:403-410; see also www.ncbi.nlm.nih.gov/BLAST/) searches under default parameters for identity to sequences contained in the BLAST "GENEMBL" database. A sequence can be analyzed for identity to all publicly available DNA sequences contained in the GENEMBL database using the BLASTN algorithm under the default parameters. Identity to the sequence of the present invention would mean a polynucleotide sequence having at least 65% sequence identity, more preferably at least 70% sequence identity, more preferably at least 75% sequence identity, more preferably at least 80% identity, more preferably at least 85% sequence identity, more preferably at least 90% sequence identity and most preferably at least 95% sequence identity wherein the percent sequence identity is based on the entire promoter region.

For purposes of defining the present invention, GAP (Global Alignment Program) is used. GAP uses the algorithm of Needleman and Wunsch (J. Mol. Biol. 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Package® (Accelrys, Inc., San Diego, Calif.) is BLOSUM62 (see Henikoff & Henikoff (1989) *Proc. Natl. Acad. Sci. USA* 89:10915).

Sequence fragments with high percent identity to the sequences of the present invention also refer to those fragments of a particular promoter sequence disclosed herein that operate to promote the seed-preferred expression of an operably-linked isolated nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments can be obtained by use of restriction enzymes to cleave the naturally occurring promoter sequences disclosed herein; by synthesizing a nucleotide sequence from the naturally-occurring DNA sequence; or through the use of PCR technology. See particularly, Mullis et al. (1987) *Methods Enzymol.* 155:335-350, and Erlich, ed. (1989) *PCR Technology* (Stockton Press, New York). Again, variants of these fragments, such as those resulting from site-directed mutagenesis, are encompassed by the compositions of the present invention.

Nucleotide sequences comprising at least about 20 contiguous sequences of the sequence set forth in SEQ ID NO:10 are encompassed. These sequences can be isolated by hybridization, PCR, and the like. Such sequences encompass fragments capable of driving seed-preferred expression, fragments useful as probes to identify similar sequences, as well as elements responsible for temporal or tissue specificity.

Biologically active variants of the promoter sequence are also encompassed by the compositions of the present invention. A regulatory "variant" is a modified form of a promoter wherein one or more bases have been modified, removed or added. For example, a routine way to remove part of a DNA sequence is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produce unidirectional nested deletions.

One example of a regulatory sequence variant is a promoter formed by causing one or more deletions in a larger promoter. The 5' portion of a promoter up to the TATA box near the transcription start site can be deleted without abolishing promoter activity, as described by Zhu et al., *The Plant Cell* 7: 1681-89 (1995). Such variants should retain promoter activity, particularly the ability to drive expression in seed or seed tissues. Biologically active variants include, for example, the native regulatory sequences of the invention having one or more nucleotide substitutions, deletions or insertions. Activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

The nucleotide sequences for the seed-preferred promoter disclosed in the present invention, as well as variants and fragments thereof, are useful in the genetic manipulation of any plant when operably linked with an isolated nucleotide sequence whose expression is to be controlled to achieve a desired phenotypic response. By "operably linked" is intended that the transcription or translation of the isolated nucleotide sequence is under the influence of the regulatory sequence. In this manner, a nucleotide sequence for the promoter of the invention may be provided in an expression cassette along with an isolated nucleotide sequence for expression in the plant of interest, more particularly in the seed of the plant. Such an expression cassette is provided with a plurality of restriction sites for insertion of the nucleotide sequence to be under the transcriptional control of the promoter.

The genes of interest expressed under the direction of the promoter of the invention can be used for varying the phenotype of seeds. This can be achieved by increasing expression of endogenous or exogenous products in seeds. Alternatively, results can be achieved by providing for a reduction of expression of one or more endogenous products, particularly enzymes or cofactors in the seed. These modifications result in a change in phenotype of the transformed seed. It is recognized that the promoter may be used with its native coding sequence to increase or decrease expression, resulting in a change in phenotype in the transformed seed.

General categories of genes of interest for the purposes of the present invention include for example, those genes involved in information, such as Zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms. It is recognized that any gene of interest, including the native coding sequence, can be operably linked to the regulatory elements of the invention and expressed in the seed.

Modifications that affect grain traits include increasing the content of oleic acid, or altering levels of saturated and unsaturated fatty acids. Likewise, increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997; the disclosures of which are incorporated herein by reference. Another example is lysine and/or sulfur-rich seed protein encoded by the soybean 2S albumin described in WO 9735023 filed Mar. 20, 1996, and the chymotrypsin inhibitor from barley, Williamson et al. (1987) *Eur. J. Biochem.* 165:99-106, the disclosures of each are incorporated by reference.

Derivatives of the following genes can be made by site-directed mutagenesis to increase the level of preselected amino acids in the encoded polypeptide. For example, the gene encoding the barley high lysine polypeptide (BHL), is derived from barley chymotrypsin inhibitor, WO 9820133 filed Nov. 1, 1996 the disclosure of which is incorporated herein by reference. Other proteins include methionine-rich plant proteins such as from sunflower seed, Lilley et al. (1989) *Proceedings of the World Congress on Vegetable Protein Utilization in Human Foods and Animal Feedstuffs*; Applewhite, H. (ed.); American Oil Chemists Soc., Champaign, Ill. :497-502, incorporated herein by reference; corn, Pedersen et al. (1986) *J. Biol. Chem.* 261:6279; Kirihara et al. (1988) *Gene* 71:359, both incorporated herein by reference; and rice, Musumura et al. (1989) *Plant Mol. Biol.* 12:123, incorporated herein by reference. Other important genes encode glucans, Floury 2, growth factors, seed storage factors and transcription factors.

Agronomic traits in seeds can be improved by altering expression of genes that: affect the response of seed growth and development during environmental stress, Cheikh-N et al (1994) *Plant Physiol.* 106(1):45-51) and genes controlling carbohydrate metabolism to reduce kernel abortion in maize, Zinselmeier et al. (1995) *Plant Physiol.* 107(2):385-391. These include, for example, genes encoding cytokinin biosynthesis enzymes, such as isopentenyl transferase; genes encoding cytokinin catabolic enzymes, such as cytokinin oxidase; genes encoding polypeptides involved in regulation of the cell cycle, such as CyclinD or cdc25; genes encoding cytokinin receptors or sensors, such as CRE1, CKI1, and CKI2, histidine phospho-transmitters, or cytokinin response regulators.

Insect resistance genes may encode resistance to pests that have great yield drag such as rootworm, cutworm, European Corn Borer, and the like. Such genes include, for example: *Bacillus thuringiensis* endotoxin genes, U.S. Pat. Nos. 5,366,892; 5,747,450; 5,737,514; 5,723,756; 5,593,881; Geiser et al. (1986) *Gene* 48:109; lectins, Van Damme et al. (1994) *Plant Mol. Biol.* 24:825; and the like.

Genes encoding disease resistance traits include: detoxification genes, such as against fumonosin (WO 9606175 filed Jun. 7, 1995); avirulence (avr) and disease resistance (R) genes, Jones et al. (1994) *Science* 266:789; Martin et al. (1993) *Science* 262:1432; Mindrinos et al. (1994) *Cell* 78:1089; and the like.

Commercial traits can also be encoded on a gene(s) which could alter or increase for example, starch for the production of paper, textiles and ethanol, or provide expression of proteins with other commercial uses. Another important commercial use of transformed plants is the production of polymers and bioplastics such as described in U.S. Pat. No. 5,602,321 issued Feb. 11, 1997. Genes such as B-Ketothiolase, PHBase (polyhydroxyburyrate synthase) and acetoacetyl-CoA reductase (see Schubert et al. (1988) *J. Bacteriol* 170 (12):5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed can be increased. This is achieved by the expression of such proteins having enhanced amino acid content.

The nucleotide sequence operably linked to the regulatory elements disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant seed.

The expression cassette will also include, at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

Other convenient termination regions are available from the Ti-plasmid of *A. tumefaciens*, such as the octopine synthase and nopaline synthase termination regions. See also: Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences.

Such leader sequences can act to enhance translation. Translation leaders are known in the art and include: picornavirus leaders, for example: EMCV leader (Encephalomyocarditis 5' noncoding region), Elroy-Stein et al. (1989) *Proc. Nat Acad. Sci.* USA 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA*, pages 237-256; and maize chlorotic mottle virus leader (MCMV) Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have the expressed product of the isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector, comprising the promoter of the present invention operably linked to an isolated nucleotide sequence in an expression cassette, can also contain at least one additional nucleotide sequence for a gene to be co-transformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example: Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) *EMBO J.* 2:987-992; methotrexate, Herrera Estrella et al. (1983) Nature 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) Science 233:478-481; phosphinothricin, DeBlock et al (1987) *EMBO J.* 6:2513-2518.

Other genes that could serve utility in the recovery of transgenic events but might not be required in the final product would include, but are not limited to: GUS (β-glucoronidase), Jefferson (1987) *Plant Mol. Biol. Rep.* 5:387); GFP (green florescence protein), Chalfie et al. (1994) *Science* 263: 802; luciferase, Teeri et al. (1989) *EMBO J.* 8:343; and the maize genes encoding for anthocyanin production, Ludwig et al. (1990) *Science* 247:449.

The transformation vector comprising the particular regulatory sequences of the present invention, operably linked to an isolated nucleotide sequence of interest in an expression cassette, can be used to transform any plant. In this manner, genetically modified plants, plant cells, plant tissue, seed, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320-334; electroporation, Riggs et al. (1986) *Proc. Natl. Acad. Sci.* USA 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Biotechnology* 8:736-740 (rice); Klein et al. (1988) *Proc. Natl. Acad. Sci.* USA 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci.* USA 84:5345-5349 (Liliaceae); De Wet et al. (1985) in *The Experimental Manipulation of Ovule Tissues*, ed. G. P. Chapman et al. (Longman, N.Y.), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed can be grown into plants in accordance with conventional ways. See, for example, McCormick et al. (1986) *Plant Cell Reports* 5:81-84. These plants can then be grown and pollinated with the same transformed strain or different strains, and resulting plants having seed-preferred expression of the desired phenotypic characteristic can then be identified. Two or more generations can be grown to ensure that seed-preferred expression of the desired phenotypic characteristic is stably maintained and inherited.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention. It will be obvious that certain changes and modifications may be practiced within the scope of the appended claims.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

All parts or amounts set out in the following examples are by weight, unless otherwise specified.

Unless otherwise stated, size separation of fragments in the examples below was carried out using standard techniques of agarose and polyacrylamide gel electrophoresis ("PAGE") in Sambrook et al., *MOLECULAR CLONING: A LABORATORY MANUAL*, 2nd Ed., Cold Spring Harbor Laboratory Press, Cold Spring Harbor, N.Y. (1989) and numerous other references such as, for instance, by Goeddel et a., *Nucleic Acids Res*. 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 microgram of DNA.

Example 1

Construction of Vectors System for Temporal and Spatial Seed Preferred Expression of Cytokinin Biosynthetic Enzymes Construction of PHP 11466 and PHP 11467 and their Cointegrates PHP11551 and PHP11552, Respectively PPH 11466 and PHP 11467 were employed in particle gun transformation protocols even though they have the right and left border for the tDNA. The versions designated PHP11551 and PHP11552 were used in Agro-mediated transformation protocols.

The ipt coding sequence was obtained as a 732 bp BamHI/HpaI fragment and inserted into a GLB1 expression cassette (BamHI/HpaI, 4.9 kb) to give PHP11310. The maize GLB1 promoter (Genbank Accession # L22344 L22295) and terminator (Genbank Accession # L22345 L22295) in PHP3303 comprise the GLB1 expression cassette. The pGLB1:ipt: GLB1 3' cassette was moved as two pieces (HindIII/BamHI 1401 bp and BamHI/EcoRI 1618 bp) into a T-DNA vector digested with EcoRI+HindIII (6.33 kb) to give PHP11363. Finally, a selectable marker gene (pUBI:UBIINTRON1: maize-optimized PAT:35S 3') was added as a 2.84 kb HindIII fragment into HindIII-digested PHP11363 (9.35 kb). In PHP11466, the two genes are in opposite orientation relative to each other. In PHP11467, the two genes are oriented in the same direction. After triparental mating the cointegrate of PHP11466/PHP10523 was designated PHP11551. Likewise, the cointegrate of PHP11467/PHP10523 was designated PHP11552.

Construction of PHP11404 and PHP11550

PHP 11404 was used with the biolistics-mediated transformation protocol. The plasmid has all the features of the Agro version. The plasmid that was actually used with the Agro-mediated transformation protocols was is PHP11550. Using the plasmid PHP9063 (pUBI:UBIINTRON1:ipt:pinII 3'), an NcoI restriction site was created at the start codon of ipt using site-directed mutagenesis (specifically, the MORPH™ Kit of 5 Prime→3 Prime, Inc.). The resulting plasmid was designated PHP11362. The ipt coding sequence was then moved as a 724 bp NcoI/HpaI fragment into PHP8001 (BamHI-cut, treated with Klenow to fill in the overhang to a blunt then cut with NcoI, 4.9 kb) to give PHP11401. PHP8001 contains the GZ-W64A promoter and terminator from the 27 KD zein gene of *Z. mays* (Genbank Accession # S78780). PHP11401 was digested with PacI+KpnI and a 1.35 kb fragment inserted into PHP11287 (PacI/KpnI-digested, 10.87 kb) to give PHP11404. PHP11287 is a T-DNA vector that already carries the above-described pUBI:UBIINTRON1:maize-optimized PAT:35S 3' selectable marker. After triparental mating the cointegrate of PHP11404/PHP10523 was designated PHP11550.

Construction of PHP12975

The CIM1 promoter is described in U.S. patent application Ser. No. 09/377,648, filed Aug. 19, 1999. Site-directed mutagenesis was used to create an NcoI site at the CIM1 translational start (PHP12699). The promoter was cut out as a 1.69 kb SacI/NcoI fragment and ligated to the ipt coding sequence and pinII terminator from PHP11362 to form PHP12800. The CIM1:ipt:pinII transcriptional unit was then moved as a 2.8 kb BstEII fragment into BstEII-digested PHP12515 (9.5 kb), a binary vector already carrying the UBI:UBIINTRON1:MO-PAT:35S selectable marker between the border sequences. The resulting plasmid was designated PHP12866. Triparental mating into *A. tumefaciens* LBA4404 (PHP10523) gave the cointegrate plasmid PHP12975.

Construction of PHP12425

Plasmid PHP11404 (described above) was used as a starting plasmid to replace the GZ-W64A promoter with the LTP2 promoter from *H. vulgare*. PHP11404 DNA was digested with NotI and KpnI (9.46 kb fragment) and separately with NcoI plus KpnI (1.24 kb fragment). These two fragments were mixed with a 1.52 kb NotI/NcoI fragment from PHP8219 containing the LTP2 promoter and ligated. The resulting plasmid product was designated PHP12333. Triparental mating of this plasmid into *A. tumefaciens* LBA4404 (PHP10523) gave the cointegrate plasmid PHP12425.

Triparental Mating and Selectable Marker 35s:bar:pinII:

All vectors were constructed using standard molecular biology techniques. The T-DNA region for transformation consists of the T-DNA border sequences flanking a reporter gene and a selectable marker. The reporter is inserted proximal to the right T-DNA border and consists of the 2.0 kb PstI fragment of the maize ubiquitin promoter Ubi-1 (Christensen et al., 1992) with flanking 5' HindIII and 3' BamHI restriction sites. The ubiquitin promoter was ligated to the 5' BamHI site of a beta-glucuronidase (GUS) reporter gene (Jefferson et al., 1986), containing the second intron from potato ST-LS1 (Vancanneyt et al., 1990). The potato proteinase II (pinII) terminator (bases 2 to 310 from An et al., Plant Cell 1(1):115-122 (1989)) was blunt-end ligated downstream of the GUS coding sequence. On the 3' end of the terminator is a NotI restriction site.

The selectable marker consists of an enhanced cauliflower mosaic virus 35S promoter (bases −421 to −90 and −421 to + 2 from Gardner, R. C., et al, Nucl. Acids Res. 9:2871-88 (1981).)) with a flanking 5' NotI site and 3' PstI site. A PstI/SalI fragment containing the 79 bp tobacco mosaic virus leader (Gallie, D. R., et al., Nucl. Acids Res. 15:3257-73 (1987).)) is inserted downstream of the promoter followed by a SalI/BamHI fragment containing the first intron of maize alcohol dehydrogenase ADH1-S (Dennis et al., 1984). The BAR coding sequence (Thompson, C. J., et al., Embo J. 6:2519-23 (1987).)) was cloned into the BamHI site, with the pinII terminator ligated downstream. The pinII signal is flanked by a 3' SacI site.

The T-DNA of PHP8904 was integrated into the super binary plasmid pSB1 (Ishida et al. 1996) by homologous recombination between the two plasmids. E. coli strain HB101 containing PHP8904 was mated with Agrobacterium strain LBA4404 harboring pSB1 to create the cointegrate plasmid in Agrobacterium designated LBA4404(PHP10525) (by the method Ditta, G., et al., Proc. Natl. Acad. Sci. USA 77:7347-51 (1980).) LBA4404(PHP10525) was selected for by Agrobacterium resistance to spectinomycin and verified as a recombinant by a SalI restriction digest of the plasmid.

Example 2

Transformation of Maize

Biolistics:

The inventive polynucleotides contained within a vector are transformed into embryogenic maize callus by particle bombardment, generally as described by Tomes, D. et al., IN: Plant Cell, Tissue and Organ Culture: Fundamental Methods, Eds. O. L. Gamborg and G. C. Phillips, Chapter 8, pgs. 197-213 (1995) and is briefly outlined below. Transgenic maize plants are produced by bombardment of embryogenically responsive immature embryos with tungsten particles associated with DNA plasmids. The plasmids consist of a selectable and an unselected structural gene.

Preparation of Particles:

Fifteen mg of tungsten particles (General Electric), 0.5 to 1.8 µ, preferably 1 to 1.8 µ, and most preferably 1 µ, are added to 2 ml of concentrated nitric acid. This suspension was sonicated at 0° C. for 20 minutes (Branson Sonifier Model 450, 40% output, constant duty cycle). Tungsten particles are pelleted by centrifugation at 10000 rpm (Biofuge) for one minute, and the supernatant is removed. Two milliliters of sterile distilled water are added to the pellet, and brief sonication is used to resuspend the particles. The suspension is pelleted, one milliliter of absolute ethanol is added to the pellet, and brief sonication is used to resuspend the particles. Rinsing, pelleting, and resuspending of the particles is performed two more times with sterile distilled water, and finally the particles are resuspended in two milliliters of sterile distilled water. The particles are subdivided into 250-ml aliquots and stored frozen.

Preparation of Particle-Plasmid DNA Association:

The stock of tungsten particles are sonicated briefly in a water bath sonicator (Branson Sonifier Model 450, 20% output, constant duty cycle) and 50 ml is transferred to a microfuge tube. All the vectors were cis: that is the selectable marker and the gene of interest were on the same plasmid. These vectors were then transformed either singly or in combination.

Plasmid DNA was added to the particles for a final DNA amount of 0.1 to 10 µg in 10 µL total volume, and briefly sonicated. Preferably, 10 µg (1 µg/µL in TE buffer) total DNA is used to mix DNA and particles for bombardment. Specifically, 1.0 µg of PHP 11404, 11466, and/or 11467 (1µg/µL), where any cytokinin biosynthetic enzyme polynucleotide can replace ipt were used per bombardment. Fifty microliters (50 µL) of sterile aqueous 2.5 M $CaCl_2$ are added, and the mixture is briefly sonicated and vortexed. Twenty microliters (20 µL) of sterile aqueous 0.1 M spermidine are added and the mixture is briefly sonicated and vortexed. The mixture is incubated at room temperature for 20 minutes with intermittent brief sonication. The particle suspension is centrifuged, and the supernatant is removed. Two hundred fifty microliters (250 µL) of absolute ethanol are added to the pellet, followed by brief sonication. The suspension is pelleted, the supernatant is removed, and 60 ml of absolute ethanol are added. The suspension is sonicated briefly before loading the particle-DNA agglomeration onto macrocarriers.

Preparation of Tissue

Immature embryos of maize variety High Type II are the target for particle bombardment-mediated transformation. This genotype is the $F_1$ of two purebred genetic lines, parents A and B, derived from the cross of two know maize inbreds, A188 and B73. Both parents are selected for high competence of somatic embryogenesis, according to Armstrong et al, Maize Genetics Coop. News 65:92 (1991).

Ears from $F_1$ plants are selfed or sibbed, and embryos are aseptically dissected from developing caryopses when the scutellum first becomes opaque. This stage occurs about 9-13 days post-pollination, and most generally about 10 days post-pollination, depending on growth conditions. The embryos are about 0.75 to 1.5 millimeters long. Ears are surface sterilized with 20-50% Clorox for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l $AgNO_3$. Chu et al., Sci. Sin. 18:659 (1975); Eriksson, Physiol. Plant 18:976 (1965). The medium is sterilized by autoclaving at 121° C. for 15 minutes and dispensed into 100×25 mm Petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3-16 hour, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 ml are deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used, with 650 to 1100 psi being preferred, and about 900 psi being most highly preferred. Multiple disks are used to effect a range of rupture pressures.

The shelf containing the plate with embryos is placed 5.1 cm below the bottom of the macrocarrier plafform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferates from about 7% of the bombarded embryos. Putative transgenic tissue is rescued, and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the cytokinin biosynthetic enzymes and non-cytokinin biosynthetic enzyme portion of the plasmid. Embryogenic tissue with amplifiable sequence is advanced to plant regeneration.

For regeneration of transgenic plants, embryogenic tissue is subcultured to a medium comprising MS salts and vitamins (Murashige & Skoog, *Physiol. Plant* 15: 473 (1962)), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm Petri dishes, and is incubated in darkness at 28° C. until the development of well-formed, matured somatic embryos can be seen. This requires about 14 days. Well-formed somatic embryos are opaque and cream-colored, and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite in 100×25 mm Petri dishes and incubated under a 16 hour light:8 hour dark photoperiod and 40 meinsteinsm$^{-2}$ sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hour light:8 hour dark photoperiod and 40 meinsteinsm$^{-2}$ sec$^{-1}$ from cool-white fluorescent tubes. After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

*Agrobacterium*-mediated:

When *Agrobacterium*-mediated transformation is used, the method of Zhao is employed as in PCT patent publication WO98/32326, the contents of which are hereby incorporated by reference. Briefly, immature embryos are isolated from maize and the embryos contacted with a suspension of *Agrobacterium* (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants.

Example 3

Identification of High Cytokinin Transgenic Corn Lines

The resulting transformants are screened for elevated levels of cytokinin using a combination of direct measurements and in vivo correlates.

Vivipary Experiments (glb1:ipt constructs):

Because it is appreciated that seed dormancy is controlled by the ratio of ABA:cytokinin, an elevated cytokinin level in the seed could induce a viviparous phenotype.

Glb1::ipt transformants were initiated using GS3 embryos and either *Agrobacterium*—(inventive polynucleotides 11551 and 11552) or biolistic—(inventive polynucleotides 11466 and 11467) mediated transformation. Plantlets were regenerated 2-3 months later and these plantlets (T0's) were transferred to the greenhouse after an additional 2-3 months. At anthesis, T0's were crossed with HG11 and vivipary was detected in the developing T1 seed approximately 30 days later. Developing T1 seed that exhibited the viviparous phenotype was rescued by replanting without seed drying. Viable plants were analyzed by PCR and leaf-painting to determine if the ipt gene and the selectable marker (PAT gene) were present. T1 plants flowered and ears were selfed to create T2 seed. Those plants carrying the ipt gene (PCR- and leaf paint-positive) produced seed that were segregating 3:1 for the gene, whereas the plants that were PCR- and leaf paint-negative did not segregate.

Figure 1B:
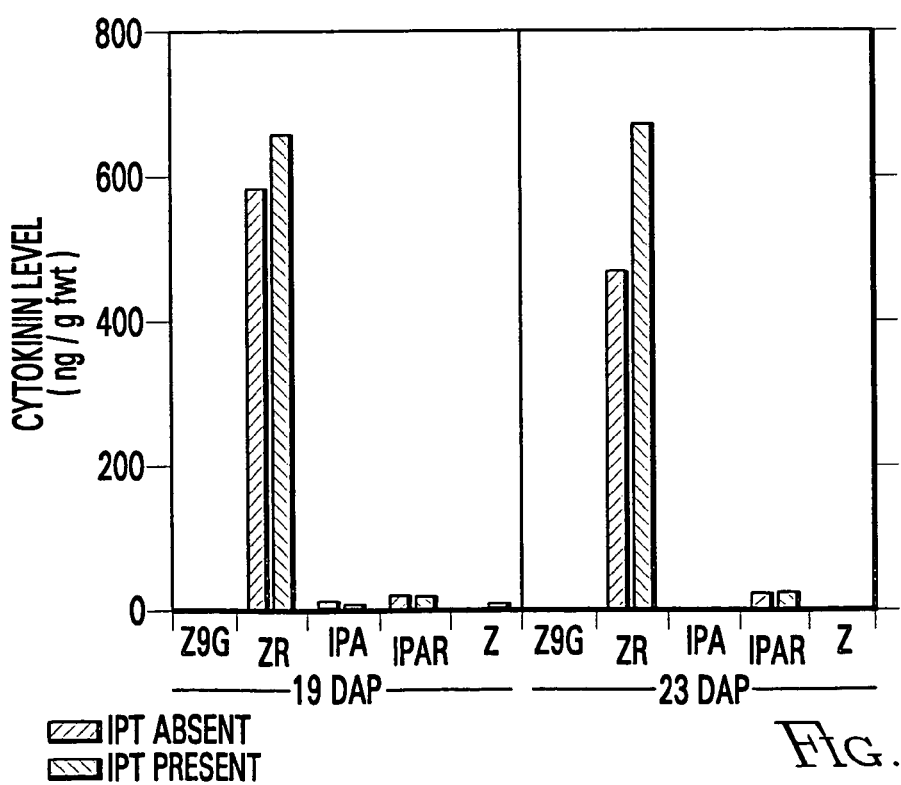

Cytokinin Determinations:

t 19 and 23 days after pollination (DAP), ten seeds were harvested from each of four replications per event (11551 and 11552). Seeds were then separated into embryo and endosperm and frozen in liquid nitrogen. At each sampling date, embryo tissue from the four replications was pooled and cytokinin levels were determined. Endosperm tissue was processed in an similar manner. The results are presented in FIG. 1.

glb1::ipt Seed Propagation:

In order to propagate the viviparous seed, half of the remaining plants within each event were harvested at 25 DAP. Ears were placed in dryer boxes and ambient air (22 to 25 C) was blown across them for three days to slowly dry the seed. Dryer boxes containing the transgenic ears were then transferred to a growth chamber and seeds were dried to ~12% moisture by blowing 35 C air across them for 3 to 5 days. Individual ears were then shelled and the seeds stored at 10 C and 50%RH.

Phenotype Determination:

To determine the proportion of seed exhibiting vivipary, ears from the remaining half of the plants were harvested at approximately 45 DAP and seed scored for degree of vivipary. The four classes of vivipary were defined as:

Class 1: No apparent swelling of coleoptile.

Class 2: Visible swelling of coleoptile, but no elongation.

Class 3: Visible swelling of coleoptile with elongation past the scutellum, but no rupture of pericarp.

Class 4: Visible swelling of coleoptile with elongation past the scutellum and rupture of pericarp.

The results are shown below in Table 1.

TABLE 1

| Event | SID # | PCR Result | Leaf Paint Result | T2 Phenotype Vivipary Result | Vivipary Characterization at 45 DAP Class 1 | Class 2 | Class 3 | Class 4 | Total Seed # |
|---|---|---|---|---|---|---|---|---|---|
| 11551 | 751412 | + | + | + | 4 | 4 | 7 | 4 | 19 |
|  | 751415 | + | + | + | 0 | 169 | 34 | 2 | 205 |
|  | 751416 | + | + | + | 99 | 28 | 18 | 59 | 204 |
|  | 751417 | + | + | + | 167 | 55 | 39 | 18 | 279 |
|  | 751420 | + | + | + | 2 | 193 | 47 | 0 | 242 |
|  | 751422 | + | + | + | 0 | 141 | 93 | 11 | 245 |
|  | Sum |  |  |  | 272 | 590 | 238 | 94 | 1194 |
| 11551 | 751425 | + | + | + | 50 | 57 | 85 | 4 | 196 |
|  | 751426 | + | + | + | 0 | 75 | 64 | 12 | 151 |
|  | 751429 | + | + | + | 66 | 40 | 19 | 4 | 129 |
|  | 751432 | + | + | + | 41 | 16 | 14 | 4 | 75 |
|  | Sum |  |  |  | 157 | 188 | 182 | 24 | 551 |
| 11551 | 751433 | − | − |  |  |  |  |  |  |
|  | 751434 | − | − | − | 438 | 0 | 0 | 0 | 438 |
|  | 751435 | − | − |  | 405 | 0 | 0 | 0 | 405 |
|  | 751436 | − | − |  | 375 | 0 | 0 | 0 | 375 |
|  | Sum |  |  |  | 406 | 0 | 0 | 0 | 406 |
| 11551 | 751437 | + | + | + | 14 | 50 | 78 | 19 | 161 |
|  | 751438 | − | + | + | 52 | 37 | 128 | 10 | 227 |
|  | 751439 | + | + | + | 128 | 92 | 101 | 9 | 330 |
|  | 751443 | + | + | + | 70 | 84 | 89 | 4 | 247 |
|  | Sum |  |  |  | 264 | 263 | 396 | 42 | 965 |
| 11551 | 751441 | − | − | − | 375 | 0 | 0 | 0 | 375 |
|  | 751442 | + | − |  |  |  |  |  |  |
|  | 751444 | − | − | − | 343 | 0 | 0 | 0 | 343 |
|  | Sum |  |  |  | 359 | 0 | 0 | 0 | 359 |
| 11551 | 751445 |  |  | + | 158 | 76 | 38 | 9 | 281 |
|  | 751448 | − | + | + | 4 | 126 | 79 | 3 | 212 |
|  | 751450 | + | + | + | 101 | 83 | 44 | 14 | 242 |
|  | 751451 | + | + | + | 101 | 33 | 48 | 1 | 183 |
|  | Sum |  |  |  | 364 | 318 | 209 | 27 | 918 |
| 11552 | 752902 |  | + | + | 16 | 53 | 62 | 4 | 135 |
|  | 752908 | + | + | + | 35 | 74 | 24 | 4 | 137 |
|  | 752910 | + | + | + | 9 | 132 | 14 | 0 | 155 |
|  | 752911 | + | + | + | 2 | 148 | 39 | 3 | 192 |
|  | 752912 | + | + | + | 0 | 40 | 27 | 2 | 69 |
|  | 752913 | + | + | + | 49 | 36 | 36 | 8 | 129 |
|  | 752914 | + |  | + | 75 | 47 | 12 | 21 | 155 |
|  | 752919 |  | + | + | 25 | 72 | 80 | 16 | 193 |
|  | Sum |  |  |  | 211 | 602 | 294 | 58 | 1165 |
| 11551 | 752924 | + | + | + | 109 | 57 | 98 | 16 | 280 |
|  | 752930 | + | + | + | 6 | 27 | 22 | 10 | 65 |
|  | 752936 | + | + | + | 53 | 60 | 47 | 3 | 163 |
|  | 752937 | + | + | + | 53 | 36 | 70 | 10 | 169 |
|  | 752939 | + | + | + | 58 | 48 | 68 | 6 | 180 |
|  | 752940 | + | + |  | 0 | 1 | 0 | 0 |  |
|  | Sum |  |  |  | 279 | 229 | 305 | 45 | 857 |

The results of the phenotypic evaluation demonstrated that the presence of the ipt gene resulted in a greater occurrence of vivipary (Classes 2 through 4), relative to the plants without the gene.

Increased Seed Dry Unit Mass (gz:ipt constructs):

Because kernel mass is a function of the number of endosperm cells and amyloplasts, and cytokinins have been implicated in increasing endosperm cell number and in the differentiation of amyloplasts from proplastids, seeds exhibiting an increased level of cytokinin should yield a corresponding increase in seed dry unit mass.

Gz::ipt transformants were initiated using GS3 embryos and *Agrobacterium*-mediated transformation (inventive polynucleotide 11550). Plantlets were regenerated in 2-3 months in 1997 and these plantlets (T0's) were transferred to the greenhouse after an additional 2-3 months. At anthesis, T0's were crossed with HG11 and at maturity the ears were harvested, shelled and the seed used for additional seed propagation (both backcrossing to HG11 and self-pollinating). T2 seed (both BC2 generation and selfs) was then planted. The T2 plants were analyzed by using PCR and leaf painting to determine if the ipt gene and the selectable marker (PAT gene) were present, respectively. Subsets of these plants were self-pollinated for cytokinin determinations, or allowed to open pollinate for phenotype determinations (yield and yield components).

Cytokinin Determinations:

Samples can be collected and analyzed as follows. At 10, 16 and 22 DAP, 50 to 100 seeds can be collected from two replications per event (each replication was composed of two subsamples) and the pedicel removed. For the 10 DAP samples, the remaining seed tissue can be placed directly into liquid nitrogen (tissue defined as "seed," composed primarily of pericarp, aleurone, endosperm and nucellus). In contrast, at 16 and 22 DAP, the embryo can be first dissected from the remaining seed tissue (tissue defined as "seed minus embryo," and composed primarily of pericarp, aleurone and endosperm) and then both tissues placed directly into liquid nitrogen.

Phenotype Determination:

To determine the effect of the gz::ipt construct on seed mass, individual plants are hand harvested at physiological maturity (visible black layer), the seed shelled and oven dried to a constant mass (104 C, minimum of 3 days). Yield (g plant) and the components of yield (ears per plant, seeds per ear and wt per seed) are determined on primary and secondary ears.

Increased Frequency Of Seed Set And Increased Number Of Seeds (ltp2:ipt constructs):

Because yield is a combination of both frequency of seed set and number of seeds per ear, seeds exhibiting an increased level of cytokinin in the early stages of seed set and formation should have ears with a corresponding increase in seed set and numbers.

Ltp2::ipt transformants were initiated using GS3 embryos and *Agrobacterium*-mediated transformation (12425). Plantlets were regenerated in 2-3 months in 1998 and these plantlets (T0's) were transferred to the greenhouse after an additional 2-3 months. At anthesis, T0's were crossed with HG11 and at maturity the ears were harvested, shelled and the seed used for additional seed propagation (both backcrossing to HG11 and self-pollinating). The number of seeds per T0 event, and the number of events which set seed were compared to a number of other transgenic events with promoter:gene combinations other than ltp2:ipt. These are shown in Table 2.

TABLE 2

Seed set average of T0 events of ltp2:ipt gene compared to other genes in T0 plants grown under identical green house conditions in 1998 in Johnston, IA.

| Inventive polynucleotide | gene description | number T0's | % T0 w/seed | average # seeds |
|---|---|---|---|---|
| 12425 | ltp2:ipt | 35 | 82.9 | 198 |
| 12384 | lignin | 92 | 22.8 | 145 |
| 12417 | carbohydrate | 40 | 55.0 | 156 |
| 12427 | maturity | 35 | 45.7 | 69 |
| 12428 | lignin | 29 | 75.9 | 174 |
| 12723 | lignin | 35 | 62.9 | 184 |
| 12724 | lignin | 35 | 45.7 | 161 |

Compared to % seed set and average # seeds per T0 plant, ltp2:ipt, had both the highest % of T0 plants which set seed and the highest numerical average # of seeds compared to six other transgenic combinations in T0 plants grown at the same time and under the same greenhouse conditions. These results indicate that expression of cytokinin in the aleurone layer of early seed development may increase yield by increasing both the percentage of plants that set seed, and the number of seeds set per ear.

Subsequent generations will be grown at different field locations to determine their seed set and seed number characteristics and seed yield compared to non-transgenic controls of the same genetic background. Cytokinin levels will also be measured on transgenic and non-transgenic kernels of similar genetic background.

Cytokinin Determinations:

Samples can be collected and analyzed as follows. At 2, 6 and 22 DAP, 50 to 100 seeds can be collected from two replications per event (each replication composed of two subsamples) and the pedicel removed. For the 2, 6, and 22 DAP samples, the remaining seed tissue can be placed directly into liquid nitrogen (tissue defined as "seed," composed primarily of pericarp, aleurone, endosperm and nucellus).

EXAMPLE NO. 4

Isolation of ipt and Isolation of ckx1-2

Briefly, PCR primers preferably containing convenient restriction endonuclease sites are constructed. Two useful primers are shown below:

SEQ ID NO: 38 (Upper primer with Bam H1 site)
5'caucaucaucauggatccaccaatggatctacgtctaattttcggtcc aac 3'

SEQ ID NO: 39 (Lower primer with HpaI site)
5'cuacuacuacuagttaactcacattcgaaatggtggtccttc 3'

The introduced restriction sites are bolded. The portion of the primer that binds to the template extends from nucleotides 22 and 19 to the 3' terminus, respectively. A BamHI site "ggatcc" (bolded) and a Kozak consensus sequence were introduced before the start codon and a HpaI site "gttaac" (also bolded) was introduced after the stop.

The *Agrobacterium tumefaciens* strain carrying the tumor-inducing plasmid pTi Bo542 was obtained (See Guyon, P., et al., *Agropine in null-type crown gall tumors: Evidence for generality of the opine concept*, Proceedings of the National Academy of Sciences (U.S.) 77(5): 2693-97 (1980); Chilton, W. S., et al. *Absolute stereochemistry of leucinopine, a crown gall opine*, Phytochemistry (Oxford) 24(2): 221-24 (1985); Strabala, T. J., et al., *Isolation and characterization of an ipt gene from the Ti plasmid* Bo542, Molecular & General Genetics 216: 388-94 (1989)) and live bacteria were used for the PCR template. Standard PCR conditions were used. An example of such conditions follows: Volume per reaction of 100 µL, with 0.5 µL of 10 ng/µL target plasmid, 0.05 Unit/µL Taq Polymerase, 0.5 µM each of primers, 0.8 mM dNTP's 1× Buffer in a thin walled tube. Mix reagents, keep on ice. Add target plasmid to tube and then add the 100 µL of reaction mix to each tube. Pre-incubate in a thermocycler at 95° C. for 3 minutes. Then cycle five times at 95° C. for 35 seconds, 55° C. for 1 minute, and 72° C. for 1 minute. Follow with 30 cycles at 95° C. for 35 seconds, 65° C. for 1 minute, and 72° C. for 1 minute. Finalize reaction by dwelling for 10 minutes at 72° C. and allowing to soak at 6° C. PCR product was then cloned into DH5α cells using a kit made by Life Technologies according to manufacturer's instructions. DNA was extracted from putative transformants, cut with BamHI and HpaI, and run on gel to confirm transformation. This insert was then gel purified and transformed into a convenient expression vector, such as 7921 vector DNA containing a Ubi promoter and pinII terminator.

A preferred DNA sequence is provided in Molecular and General Genetics 216:388-394 (1989). It contains an open reading frame encoding a protein of 239 amino acid residues, with a deduced molecular weight of about 26.3 kDa (Calculated as the number of amino acid residues×110).

Isolation of Maize Cytokinin Oxidase Gene, cytox 1-2

Another preferred DNA sequence is set out below as SEQ. I.D. NO:1. It contains an open reading frame encoding a protein of about 535 amino acid residues, SEQ ID NO.:2, with a deduced molecular weight of about 58.9 kDa (Calculated as the number of amino acid residues×110). A copy of cytokinin oxidase can be prepared synthetically employing DNA synthesis protocols well known to those skilled in the art of gene synthesis. Alternatively, a copy of the gene may be isolated directly from a cytokinin oxidase harboring organism by PCR cloning. A maize cytokinin oxidase gene (ckx1) was cloned by Roy Morris of the University of Missouri and the sequence deposited in Genbank. (Morris et al., 1999. Isolation of a gene encoding a glycosylated cytokinin oxidase from maize. Biochem. Biophys. Res. Commun. 255(2):328-333. See also Houba-Herin et al., 1999. Cytokinin oxidase from *Zea mays*: purification, cDNA cloning and expression in moss protoplasts. Plant J. (6):615-626.) PCR primers preferably containing convenient restriction endonuclease sites are constructed: Two useful primers are shown below:

```
                                          (SEQ ID NO: 42)
5' CATGCCATGGCGGTGGTTTATTACCTGCT 3'
(with NcoI site at 5' end)

(SEQ ID NO: 43)
5' CGGGATCCTCATCATCAGTTGAAGATGTCCT 3'
(with BamHI site at 3' end)
```

These primers were designed against the sequence of ckx1 and reverse transcriptase PCR (RT-PCR) was utilized to isolate cytokinin oxidase genes from several different tissues of developing maize kernels. DNA fragments were amplified from the following tissues: 10 DAP, 13 DAP, 18 DAP, and 20 DAP endosperms; as well as 10 DAP, 18 DAP, and 20 DAP embryos, where DAP is days after pollination. Fragments from all tissues migrated to 1.6 Kb in the gel, which is equal to that of the published sequence. We selected one of the fragments (from 18 DAP embryos) and sequenced the DNA. This fragment is referred to herein as Cytox1-2 and its full-length sequence is set out below in SEQ ID NO.: 1. At the amino acid level, there is a 98% homology between the ckx1 gene and cytox1-2, therefore, one of skill in the art would recognize that cytox1-2 is a cytokinin oxidase gene from maize.

Example 5

Expression of Transgenes in Monocots

A plasmid vector is constructed comprising the Zag2.1 promoter (SEQ ID NO: 3) or Zap promoter (SEQ ID NO: 5, also known as ZmMADS) or tb1 promoter (SEQ ID NO: 17) operably linked to a an isolated polynucleotide encoding ipt (SEQ ID NO: 1). This construct can then be introduced into maize cells by the following procedure.

Immature maize embryos are dissected from developing caryopses derived from crosses of maize lines. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus, consisting of undifferentiated masses of cells with somatic proembryoids and ermbryoids borne on suspensor structures, proliferates from the scutellum of these immature embryos. The embryogenic callus isolated from the primary explant can be cultured on N6 medium and sub-cultured on this medium every 2 to 3 weeks.

The plasmid p35S/Ac (Hoechst Ag, Frankfurt, Germany) or equivalent may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and comprises the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton flying disc (Bio-Rad Labs). The particles are then accelerated into the corn tissue with a Biolistic PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 6

Expression of Transgenes in Dicots

Soybean embryos are bombarded with a plasmid comprising the Zag2.1 promoter operably linked to a heterologous nucleotide sequence encoding ipt, as follows. To induce somatic embryos, cotyledons of 3-5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are sub-cultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) Gene 25:179-188), and the 3' region of the nopaline synthase gene from the T-DNA of the Ti plasmid of *Agrobacterium tumefaciens*. The expression cassette of interest, comprising the Zag2.1 promoter and a heterologous polynucleotide encoding ipt, can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Analysis of Ear Growth Rate of T1 (D2F1 Hemizygous) Plants Under Non-Stress Conditions Transformation of maize with the zag2.1::ipt construct was performed as described in Example 5. Regenerated plants were pollinated with one of the parent genotypes to create D2F1 seed (D2 referring to two doses of a parent; also known as T1 seed). Of 17 original transformants, nine were selected for advancement based on favorable genetic complexity (i.e., single- to low-copy number as determined by Southern blot analysis), intactness of the plant transcriptional unit (as determined by Southern blot analysis), and adequate seed numbers.

Figure 2:
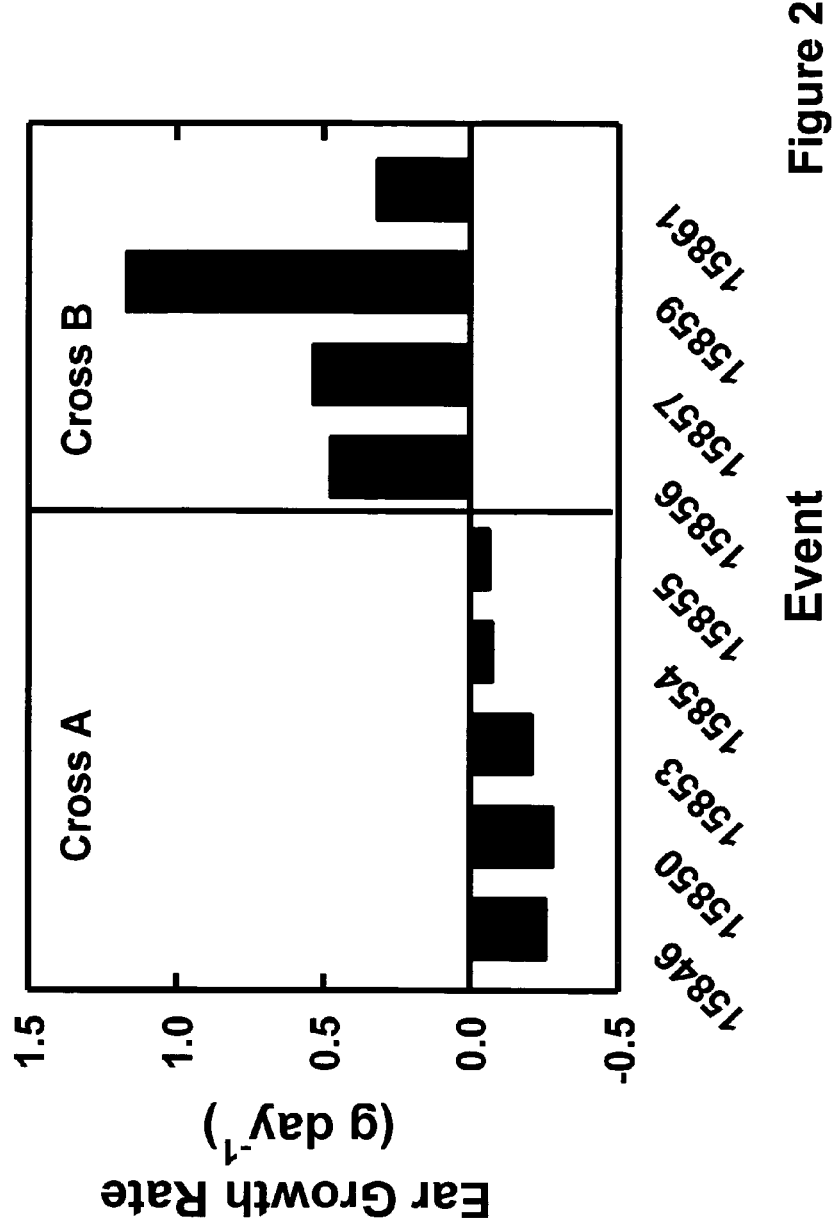
FIG. 2 presents ear growth rate data for D2F1 hemizygous plants under non-stress conditions.

The D2F1 seed was planted in a replicated, well-watered field trial in Johnston, Iowa. Dry mass of unpollinated ears was measured at initial silk emergence and seven days later. Ear growth rate (EGR) was calculated as the difference in dry mass divided by the number of days. As shown in FIG. 2, four of the nine events tested showed an increase in ear growth rate, relative to transgene-negative sibs planted as controls. Presence of the ipt transcript in developing ears representing all nine events was confirmed via RT-PCR.

However, space constraints in the field prohibited direct comparisons of transgene-positive and transgene-negative plants of the same event and same genotype. Instead, control plants in this example were grown from a bulked sample of segregating T1 seed. Control plots were thinned to standard density; also, transgene-positive plants, identified via leaf painting with herbicide, were rogued. As a result of the bulking across events and genotypes, and the variation in field conditions for transgenic vs. control plants, the differences in EGR between transgenic and control plants were muted and the results were inconclusive. Therefore, all nine events were carried forward for yield analysis the following year.

Ear growth rate differences are expected for the transgenic events and can be properly evaluated with direct comparisons in which genetic background and field growing conditions are held constant.

Example 8

Analysis of Yield of T2 (D3F1 Hemizygous) Plants Under Non-Stress Conditions

T2 seed representing the nine selected events (derived from pollination of T1 plants with a recurrent parent) was planted in an unreplicated, well-watered field trial in Johnston, Iowa. Presence of the ipt transcript in developing ears was confirmed via Northern blot analysis. Transgene-negative sibs of each event were planted as controls and a pair-wise analysis of each event was conducted (a difference analysis) as well as an event average analysis. All subject plants were detasseled and pollinated by a mixed non-transgenic male parent.

Figure 3:
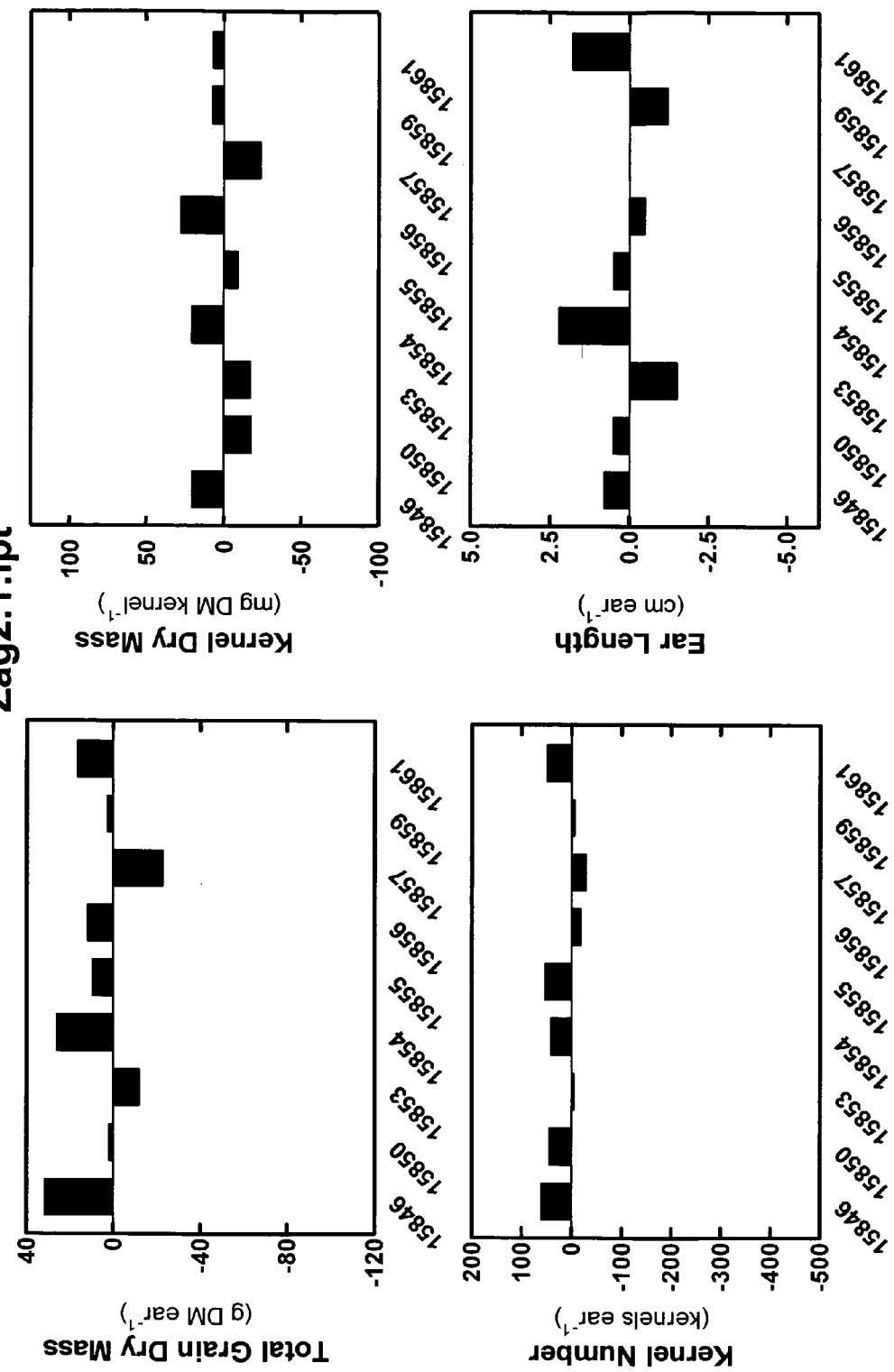
FIG. 3 presents grain yield, kernel number, kernel dry mass, and ear length data for D3F1 hemizygous plants under non-stress conditions.

Yield was determined by collecting primary ears. Grain was bulked by event and by the presence or absence of the transgene; grain was then oven-dried and measured for total dry mass. Results are shown in FIG. 3. Grain yield of seven of the nine events was greater than that of controls. Kernel number, ear length, and kernel mass were also measured; results for transgenics exceeded those for non-transgenic sibs in five out of nine events for ear length; and in five out of nine events for both kernel number and dry matter per kernel.

Example 9

Analysis of D4F3 Homozygous Plants for Yield and Plant Height

Next-generation progeny of the nine selected events were evaluated in a replicated, well-watered field trial in Johnston, Iowa, in 2002. Transgene-negative sibs were planted as controls. All subject plants were detasseled; a mix of non-transgenic plants served as the pollen source.

Figure 4:
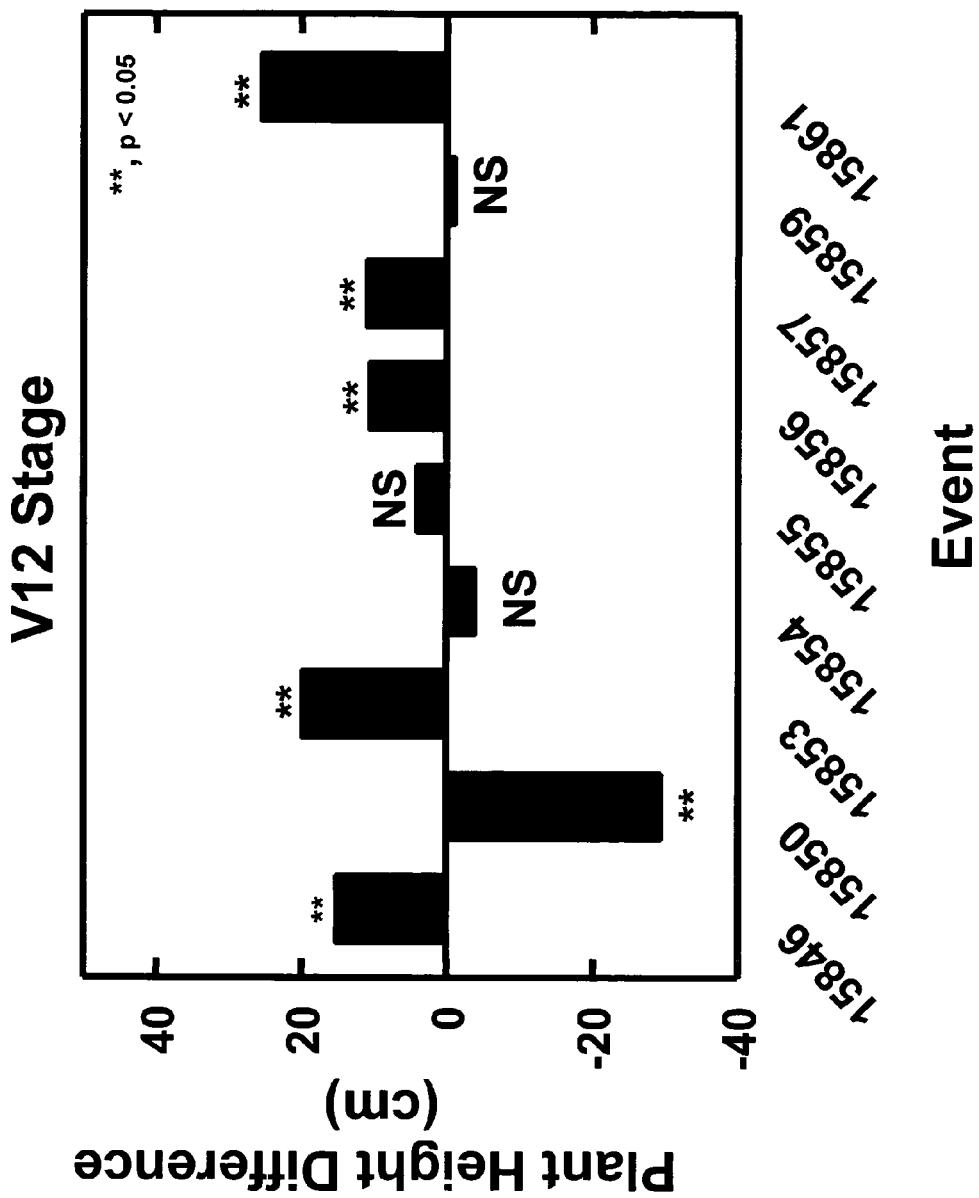
FIG. 4 presents plant height data for D4F3 homozygous plants under non-stress conditions.

Plant heights were measured at V10 and V12. (For growth stages, see *How a Corn Plant Develops*, Iowa State University of Science and Technology Cooperative Extension Service Special Report No. 48, Reprinted June 1993.) Five of the nine events showed a statistically significant increase in plant height, as shown in FIG. 4.

Figure 5:
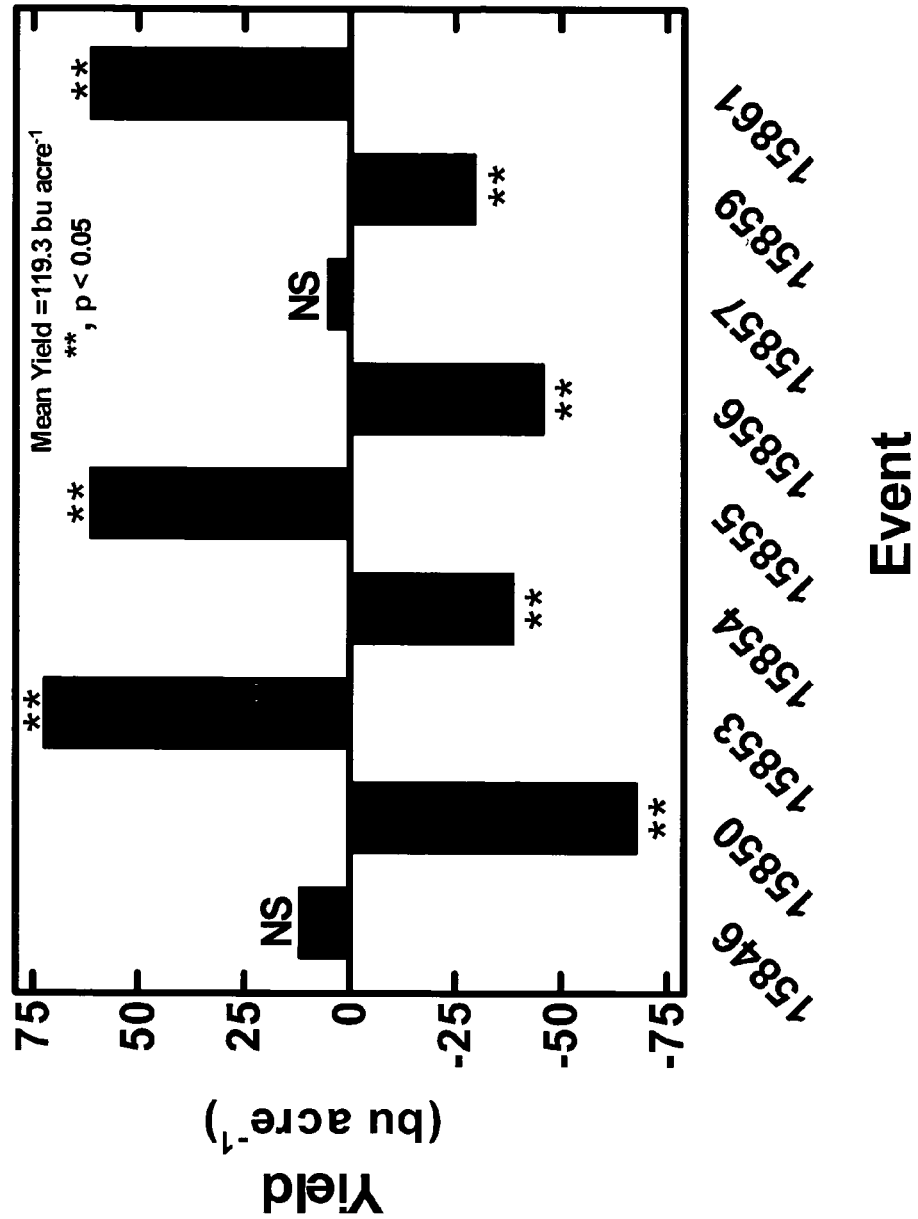
FIG. 5 presents yield data for D4F3 homozygous plants under non-stress conditions.
Figure 6:
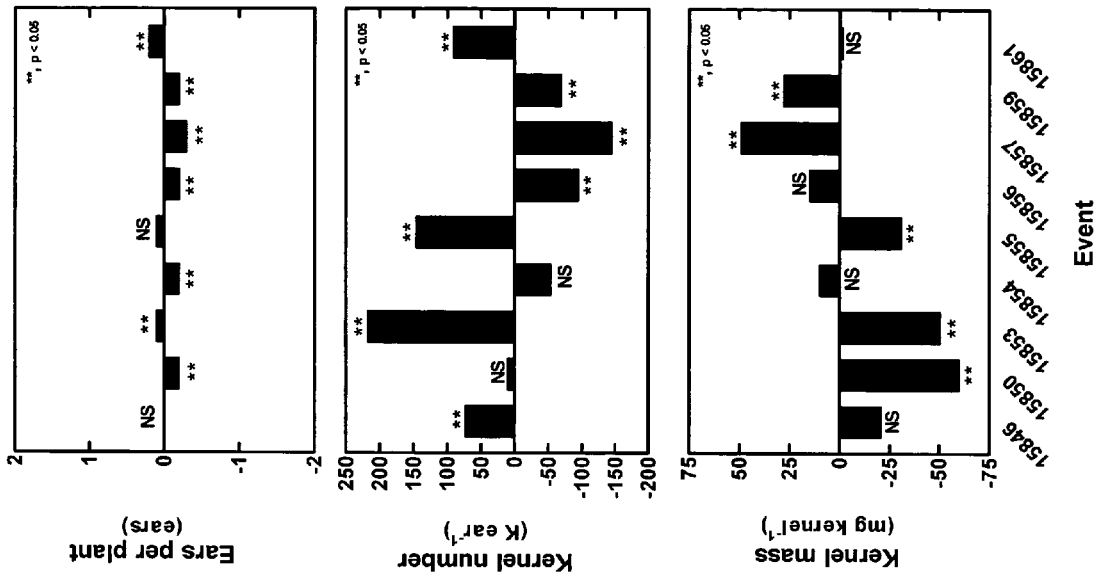
FIG. 6 provides yield component data for D4F3 homozygous plants under non-stress conditions.

Yield was determined by collecting all grain-bearing ears. Grain was bulked as appropriate, oven-dried, and measured for total dry mass. As shown in FIG. 5, three of the nine events showed a statistically significant increase in yield, including two of the events also showing increased plant height. Ear number, kernel number, and kernel mass were also measured, as shown in FIG. 6.

Example 10

Analysis of Yield, Plant Height, Leaf Greenness, Biomass, and Transgene Expression of D4F3 Plants Under Drought Stress Homozygous progeny of the nine events were evaluated under drought conditions in a replicated field trial at Woodland, Calif., in 2002. Supplemental irrigation was withheld to target a stress during anthesis sufficient to decrease yield 40% to 50%. To do this, water was withheld begininning at 920 GDUs (growing degree units) post planting and resumed at 1860 GDUs. All subject plants were detasseled and pollinated by a mixed non-transgenic male parent. Presence of the ipt transcript was determined by Northern blot analysis of developing stem, leaf, and tassel.

Figure 7:
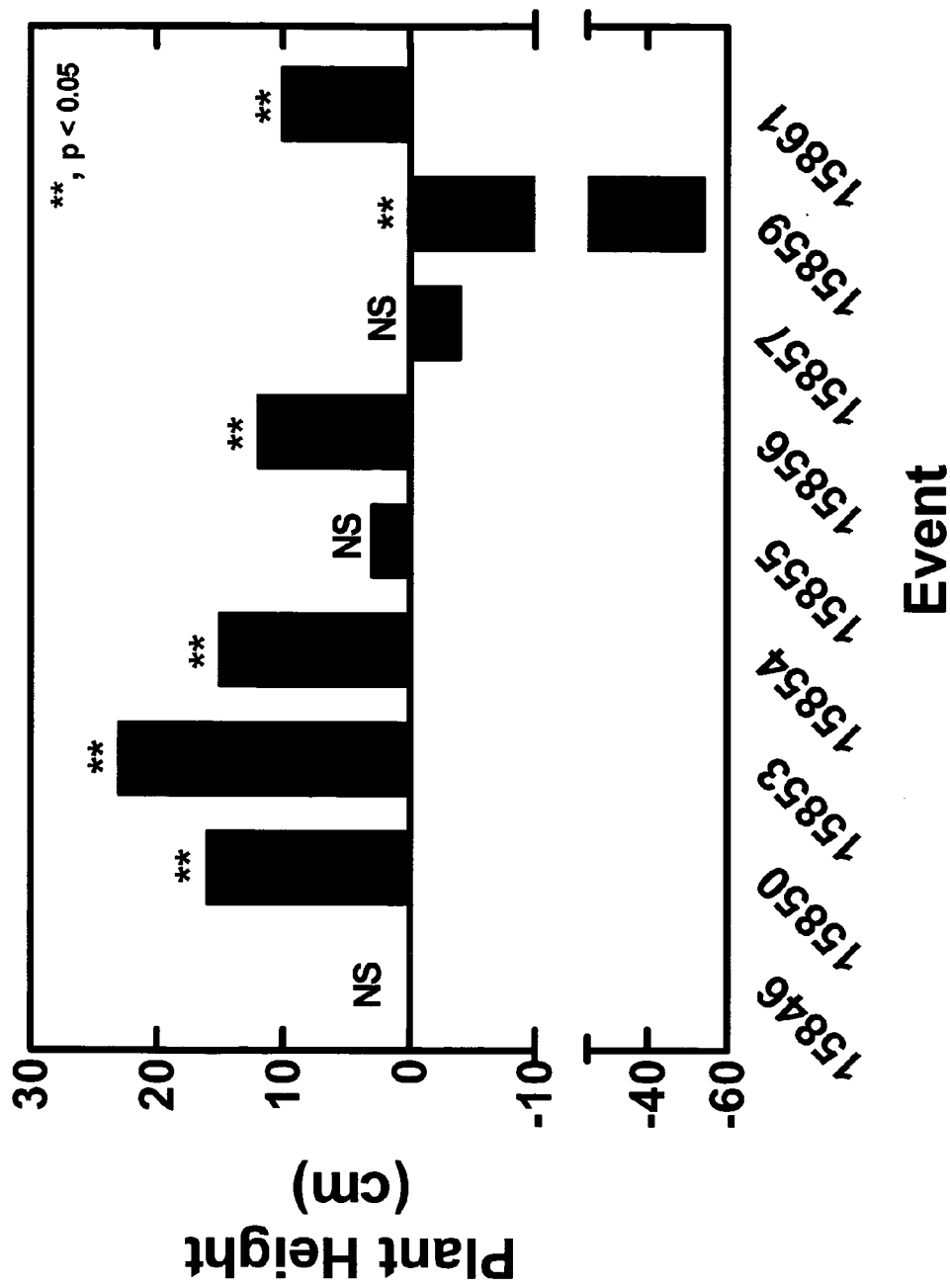
FIG. 7 provides plant height data for drought-stressed D4F3 plants.
Figure 8:
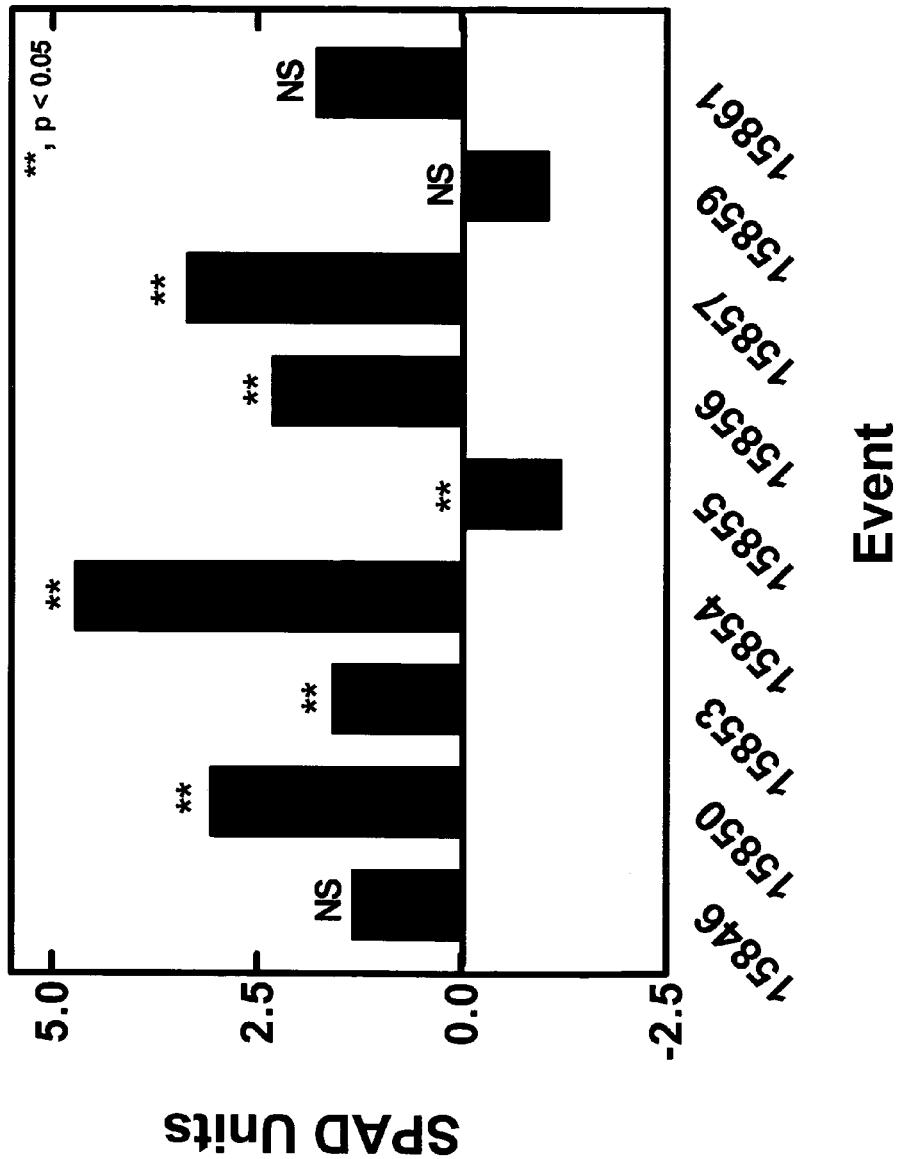
FIG. 8 provides leaf greenness data for drought-stressed D4F3 plants.

Leaf greenness was measured approximately one week prior to flowering with a Minolta SPAD chlorophyll meter. Plant height was measured at the same time. Five of the nine events showed a statistically significant increase in plant height, as shown in FIG. 7. Four of these five, and one additional event, showed increased leaf greenness, as shown in FIG. 8.

Figure 9:
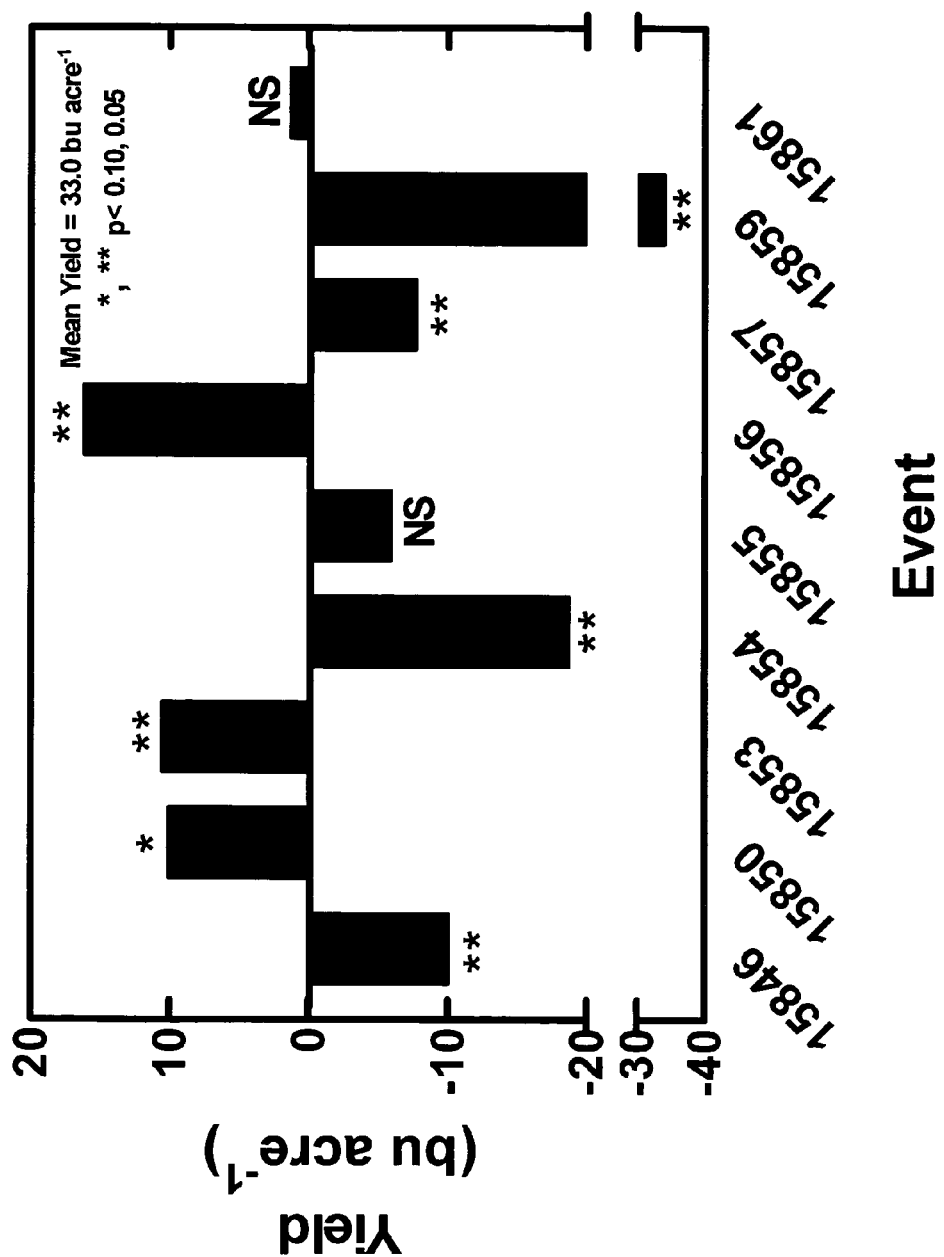
FIG. 9 provides yield data for drought-stressed D4F3 plants.

Yield was determined by collecting all grain-bearing ears. Grain was bulked as appropriate, oven-dried, and measured for total dry mass. Kernel number, ear number, and kernel mass were also measured. Three of the nine events gave improved yield results, as shown in FIG. 9; all three of these events had also displayed increased plant height and leaf greenness. The increase in plant biomass for one of these events is shown in FIG. 10. In addition, in all events tested, the transgene positive plants showed an increase in steady-state levels of ipt transcripts in various vegetative and reproductive tissues relative to that in transgene negative plants.

Example 11

Analysis of Transgene Effect on Yield of in Non-Stress Conditions

Several constructs were tested for their impact upon yield in a preliminary screen at one location with supplemental irrigation as required. All constructs were evaluated as multiple events, dose 2 elite parent, and tested for per se yield with two reps per event. Only transgene-positive plants were harvested and then all events were compared against each other for their yield advantage. The results are shown in Table 2, where the different constructs are ranked by yield, highest at the top and lowest yielding at the bottom. The second column records the raw yield, whereas the third column records the difference between that entry and the mean of all of the constructs.

TABLE 2

| PHP | Bu/acr | Construct minus mean of other constructs bu/acr | S.E. | P value |
|---|---|---|---|---|
| PHP19698 | 138.0 | 13.05 | 5.81 | 0.0248 |
| PHP19020 | 137.4 | 12.54 | 5.54 | 0.0236 |
| PHP19874 | 135.8 | 10.87 | 5.06 | 0.0318 |
| PHP15418 | 132.0 | 9.00 | 1.85 | <.0001 |
| PHP16036 | 131.2 | 6.23 | 4.86 | 0.2006 |
| PHP19304 | 129.4 | 4.42 | 4.17 | 0.2895 |
| PHP19369 | 128.6 | 3.57 | 4.17 | 0.3925 |
| PHP19512 | 126.4 | 1.30 | 4.17 | 0.7543 |
| PHP19513 | 126.0 | 0.85 | 4.22 | 0.8399 |
| PHP19815 | 124.3 | −0.89 | 4.35 | 0.8375 |
| PHP19380 | 124.1 | −1.07 | 4.17 | 0.7977 |
| PHP16889 | 124.0 | −1.18 | 7.79 | 0.8794 |
| PHP17897 | 123.3 | −1.87 | 5.67 | 0.7416 |
| PHP16037 | 122.9 | −2.34 | 4.97 | 0.6378 |
| PHP19699 | 122.7 | −2.58 | 4.32 | 0.5497 |
| PHP18070 | 122.1 | −3.11 | 4.97 | 0.5315 |
| PHP16176 | 121.7 | −3.52 | 5.22 | 0.5011 |
| PHP16178 | 121.5 | −3.74 | 6.08 | 0.5385 |
| PHP16172 | 120.8 | −4.45 | 5.58 | 0.4258 |
| PHP19523 | 120.5 | −4.82 | 4.20 | 0.2478 |
| PHP19814 | 120.3 | −5.04 | 4.37 | 0.2504 |
| PHP19368 | 118.4 | −6.92 | 4.17 | 0.0968 |
| PHP19514 | 118.1 | −7.31 | 4.20 | 0.0812 |
| PHP19822 | 117.4 | −8.23 | 4.91 | 0.0936 |

It can be seen that four constructs at the top of the table were significantly higher yielding than any of the other constructs tested. Similarly, three constructs exhibited a significantly lower yield than any of the other constructs in this test. The remainder was not sufficiently distinguished from each other and it can be assumed that their transgene does not create an impact obviously different from just the background genotype. In this test, there were four IPT constructs that were driven in expression by either Zag2.1 or Zap and this group represent the four highest yielding constructs in this test: PHP19698 Zap::IPT, PHP19020 Zag:IPT with Ubi:BAR, PHP19874 Zag::IPT with 35s BAR (head-to-head), and PHP15418 the original Zag::IPT construct with 35s BAR (head-to-tail). While the rest of these constructs were tested with 10 events per construct, in fact the re-make of PHP15418 contained over 90 events. These results clearly show the impact of coupling the IPT gene with a promoter/regulatory sequence with expression focused around female meristems.

Example 12

Analysis of zag2:ipt Expression in Soybean

Soybean embryogenic suspension cultures were transformed by the method of particle gun bombardment using procedures known in the art (Klein et al. (1987) Nature (London) 327:70-73; U.S. Pat. No. 4,945,050; Hazel, et al. (1998) Plant Cell. Rep. 17:765-772; Samoylov, et al. (1998) In Vitro Cell Dev. Biol.-Plant 34:8-13).

In particle gun bombardment procedures it is possible to use purified 1) entire plasmid DNA or, 2) DNA fragments containing only the recombinant DNA expression cassette(s) of interest. In this example, the recombinant DNA fragments were isolated from the entire plasmid before being used for bombardment. For every eight bombardments of soybean tissue, 30 μl of solution were prepared with 3 mg of 0.6 μm gold particles and up to 100 picograms (pg) of DNA fragment per base pair of DNA fragment.

The soybean transformation experiments were carried out using two recombinant DNA fragments. The recombinant DNA fragment used to express the IPT gene was on a separate recombinant DNA fragment from the selectable marker gene providing resistance to sulfonylurea herbicides. Both recombinant DNA fragments were co-precipitated onto gold particles.

Stock tissue for these transformation experiments was obtained by initiation from soybean immature seeds. Secondary embryos were excised from explants after 6 to 8 weeks on culture initiation medium. The initiation medium was an agar-solidifed modified MS (Murashige and Skoog (1962) Physiol. Plant 15:473-497) medium supplemented with vitamins, 2,4-D and glucose. Secondary embryos were placed in flasks in liquid culture maintenance medium and maintained for 7-9 days on a gyratory shaker at 26 +/−2° C. under ~80 μEm-2s-1 light intensity. The culture maintenance medium was a modified MS medium supplemented with vitamins, 2,4-D, sucrose and asparagine. Prior to bombardment, clumps of tissue were removed from the flasks and moved to an empty 60×15 mm petri dish for bombardment. Tissue was dried by blotting on Whatman #2 filter paper. Approximately 100-200 mg of tissue corresponding to 10-20 clumps (1-5 mm in size each) were used per plate of bombarded tissue. After bombardment, tissue from each bombarded plate was divided and placed into two flasks of liquid culture maintenance medium per plate of bombarded tissue. Seven days post bombardment, the liquid medium in each flask was replaced with fresh culture maintenance medium supplemented with 100 ng/ml selective agent (selection medium). For selection of transformed soybean cells the selective agent used was a sulfonylurea (SU) compound with the chemical name, 2-chloro-N-((4-methoxy-6 methy-1,3,5-triazine-2-yl)aminocarbonyl) benzenesulfonamide (common names: DPX-W4189 and chlorsulfuron). Chlorsulfuron is the active ingredient in the DuPont sulfonylurea herbicide, GLEAN®. The selection medium containing SU was replaced every week for 6-8 weeks. After the 6-8 week selection period, islands of green, transformed tissue were observed growing from untransformed, necrotic embryogenic clusters. These putative transgenic events were isolated and kept in media with SU at 100 ng/ml for another 2-6 weeks with media changes every 1-2 weeks to generate new, clonally propagated, transformed embryogenic suspension cultures. Embryos spent a total of around 8-12 weeks in SU. Suspension cultures were subcultured and maintained as clusters of immature embryos and also regenerated into whole plants by maturation and germination of individual somatic embryos.

In the greenhouse, 1400 T1 plants derived from 42 zag2:ipt::ALS transgenic events were grown at a high density (1400 plants in a space designed for 480). Eighteen plants of variety 'Jack' grown in the same environment were used as controls. Plants were grown to maturity and visually selected for unusual pod clusters, or increased pod load. Eighty three (83) zag2:ipt::ALS plants, and 18 Jack plants were measured for the number of pods per plant, number of seed per plant, and seed weight (converted to 100-seed weight). Data were subject to ANOVA using the PROC GLM procedure in SAS, and means separation were completed using the PROC MEANS function of SAS.

The null hypothesis tested was to determine if zag2: ipt::ALS plants visually selected for unusual pod clustering or apparent increased pod load were significantly different from the untransformed control (Jack). Plants from 34 events were selected, and the pod number data across all events selected was significantly different (p=0.05) between the ipt plants and Jack. Across all events, the selected zag2:ipt::ALS plants averaged 32.1 pods, which was significantly more (LSD=5.2 pods) compared to the 25.4 pods that Jack averaged.

Five events were identified that were significantly different than Jack at the 0.05 level, and at least 2 plants from each event were measured. When the pod data for these events was subject to ANOVA, the zag2:ipt::ALS plants were statistically different from the Jack plants. The plants from the 5 selected events had an average of 42.3 pods, which was statistically greater (LSD=5.9 pods) of the control.

Seed number was counted from all threshed plants of the two events with the highest average pod number (AFS 3579.7.1 and AFS 3586.1.2). The Zag2:ipt::ALS plants averaged 73.6 seed per plant, which was significantly more (LSD=11.7 seed) than average seed per plant of Jack (44.7 seed) (Table 5). The events were not statistically different from each other.

Seed of each individual zag2:ipt::ALS plant and individual Jack plants were weighed to determine if seed size was affected by the increased pod load. The 10—seed weight of individual plants from AFS 3579.7.1 and AFS 3586.1.2 was 16.6 grams, which was not statistically different (LSD=1.1 gram) from the 100 seed weight of the control Jack plants (16.2 grams).

The data examined suggest that the zag2:ipt::ALS construct potentially may influence pod number and seed per plant. In addition, seed size for the zag2:ipt::ALS plants measured was not statistically different from the non-transformed Jack control. A high level of variability existed in the greenhouse environment; however, these preliminary data suggest that the zag2:ipt::ALS construct may increase pod retention and seed per plant without a statistical difference in seed size.

Example 13

Isolation of eep1 Promoter Sequences

The procedure for promoter isolation is described in the User Manual for the Universal Genome Walker kit sold by Clontech Laboratories, Inc., Palo Alto, Calif. Genomic DNA was prepared by grinding 10-day-old *Zea mays* seedling leaves in liquid nitrogen, and the DNA prepared using the DNeasy Plant Kit (Qiagen, Valencia, Calif.). The DNA was then used exactly as described in the Genome Walker User Manual (Clontech PT3042-1 version PR68687). Briefly, the DNA was digested separately with restriction enzymes DraI, EcoRV, PvuII, ScaI, and StuI, all blunt-end cutters. In addition to the blunt enzymes suggested by Clontech, three other blunt enzymes, EcoICRI, XmnI, and SspI were also used in separate digestions. The DNA was extracted with phenol, then chloroform, then ethanol precipitated. The Genome Walker adapters were ligated onto the ends of the restricted DNA, to create a "Genome Walker Library."

For isolation of specific promoter regions, two nonoverlapping gene-specific primers (26-30 bp in length) were designed complementary to the 5' end of the maize genes identified from sequence databases. The primers were designed to amplify the region upstream of the coding sequence, i.e. the 5' untranslated region and promoter of the chosen gene. The sequences of the primers are given below. The first round of PCR was performed on each Genome Walker library with Clontech primer AP1 (SEQ ID NO:15) and the gene-specific primer (gsp)1 with the sequence shown in SEQ ID NO:11.

PCR was performed in a model iCycler thermal cycler from Bio-Rad (Hercules, Calif.) using reagents supplied with the Genome Walker kit. The following cycle parameters were used: 7 cycles of 94° C. for 2 seconds, then 68° C. for 3 minutes, followed by 32 cycles of 94° C. for 2 seconds and 67° C. for 3 minutes. Finally, the samples were held at 67° C. for 4 minutes and then at 4° C. until further analysis.

As described in the User Manual, the DNA from the first round of PCR was then diluted and used as a template in a second round of PCR using the Clontech AP2 primer (SEQ ID NO:16) and gene-specific primer (gsp)2 with the sequence shown in SEQ ID NO:12.

The cycle parameters for the second round were: 5 cycles of 94° C. for 4 seconds, then 70° C. for 3 minutes, followed by 20 cycles of 94° C. for 4 seconds, then 68° C. for 3 minutes. Finally, the samples were held at 67° C. for 4 minutes and then held at 4° C. Approximately 10 ml of each reaction were run on 0.8% agarose gel, and bands (usually 500bp or larger) were excised, purified with the Qiaquick Gel Extraction Kit (Qiagen, Valencia, Calif.) and cloned into the TA vector pGEMTeasy (Promega, Madison, Wis.). Clones were sequenced for verification.

The band produced from the XmnI Genome Walker library contained 1.5kb of sequence upstream of the gene specific primer in SEQ ID NO:12. The eep1 promoter region was obtained using primers SEQ ID NOS:13 and 14, created from this sequence to amplify 1 kb of genomic DNA from maize line A63. These primers added a HindIII site at the 5' end, an NcoI at the start of translation, and an EcoRV site just upstream of the NcoI site. These were added to aid in future vector construction. The PCR reaction was performed in a Bio-Rad iCycler (Hercules, Calif.) thermal cycler using PCR supermix High fidelity (Cat# 10790020, Invitrogen, Carlsbad, Calif.). The following cycle parameters were used: 94° C. for 2 seconds, followed by 30 cycles of 94° C. for 20 seconds, 55° C. for 30 seconds, and 68° C. for 1 minute. Finally, the samples were held at 67° C. for 4 minutes and then at 4° C. until further analysis. The PCR products were then cloned into the pGEM-T Easy vector (Promega Corp. Madison, Wis). Clones were sequenced for verification.

Example 14

Isolation of eep2 Promoter Sequences

The procedure for promoter isolation is described in the User Manual for the Universal Genome Walker kit sold by Clontech Laboratories, Inc., Palo Alto, Calif. Genomic DNA was prepared by grinding leaves from *Zea mays* B73 plants at V6 stage in liquid nitrogen, and the DNA prepared using the PureGene DNA isolation Kit (Gentra Systems, Minneapolis, Minn.). The DNA was then used exactly as described in the Genome Walker User Manual (Clontech PT3042-1 version PR68687). Briefly, the DNA was digested separately with restriction enzymes Dra I, which generates blunt-ends. The DNA was extracted with phenol, then chloroform, followed by ethanol precipitation. The Genome Walker adapters were ligated onto the ends of the restricted DNA, to create a "Genome Walker Library."

For isolation of specific promoter regions, two non-overlapping gene-specific primers (27 bp each in length) were designed complementary to the 5' end of the maize EST identified from sequence databases. The primers were designed to amplify the region upstream of the coding sequence, i.e. the 5' untranslated region and promoter of the chosen gene. The sequences of the primers are given below. The first round of PCR was performed on the Genome Walker library with Clontech primer AP1 (Sequence ID NO: 15) and the gene-specific primer 1 (GSP1) with the sequence

```
AAACACCTTCGGATATTGCTCCCTTTT.      (SEQ ID NO: 21)
```

PCR was performed in a PTC-200 DNA Engine thermal cycler from MJ Research Inc. (Waltham, Mass.) using reagents supplied with the Genome Walker kit. The following cycle parameters were used: 7 cycles of 94° C. for 10 seconds, then 72° C. for 3 minutes, followed by 32 cycles of 94° C. for 10 seconds and 67° C. for 3 minutes. Finally, the samples were held at 67° C. for 7 minutes and then at 8° C. until further analysis.

As described in the User Manual, the DNA from the first round of PCR was then diluted and used as a template in a second round of PCR using the Clontech AP2 primer (SEQ ID NO: 16) and gene-specific primer 2 (GSP2) with the sequence

```
TCTCGCATTTGCAGAAACGAACAACGT.      (SEQ ID NO: 22)
```

The cycle parameters for the second round were: 5 cycles of 94° C. for 10 seconds, then 72° C. for 3 minutes, followed by 20 cycles of 94° C. for 10 seconds, then 67° C. for 3 minutes. Finally, the samples were held at 67° C. for 7 minutes and then held at 8° C. Approximately 10 µL of each reaction were run on 1.0% agarose gel, and PCR products 500bp or larger were excised, purified with the Qiaquick Gel Extraction Kit (Qiagen, Valencia, Calif.). The band produced from the Dra I Genome Walker library contained 1.0 kb of sequence upstream of the GSP2 primer, and it was cloned into the TA cloning vector pCR2.1 (Invitrogen, Carlsbad, Calif.). Clones were sequenced for verification. The eep2 promoter region was obtained by PCR from the plasmid using primers corresponding to a 1027 bp region from downstream of AP2 primer and upstream of the ATG start codon. Clones were sequenced for verification.

The EST distribution for eep2 is as follows:

| | |
|---|---|
| p0083.cldeu53r B73 | "Kernel" " " "7 DAP whole kernels" |
| p0124.cdbmq47r B73 | "Kernel, Embryo" " " "6 day embryo sac, Screened 1" |
| p0062.cymab46r B73 | "Kernels, Endosperm" " " "coenocytic (4 DAP) embryo sacs," |
| p0106.cjlps68r B73 | "Kernel" " " "5 DAP whole kernels, screened 1" |
| p0124.cdbmq21r B73 | "Kernel, Embryo" " " "6 day embryo sac, Screened 1" |
| p0100.cbaab57r B73 | "Kernel, Embryo, Endosperm" " " "coenocytic (4 DAP) embryo sacs, screened 1 (original lib P0062)" |
| p0100.cbaac19r B73 | "Kernel, Embryo, Endosperm" " " "coenocytic (4 DAP) embryo sacs, screened 1 (original lib P0062)" |
| p0062.cyma189r B73 | "Kernels, Endosperm" " " "coenocytic (4 DAP) embryo sacs," |
| p0062.cymai74f B73 | "Kernels, Endosperm" " " "coenocytic (4 DAP) embryo sacs," |

Lynx data for eep2 in PPM:

| Name | PPM Adj | Title |
|---|---|---|
| Cen6lm | 10261 | B73 endosperm, 6 DAP embryo sac |
| Cdk8lm | 457 | Corn whole kernels, embryo and endosperm, 8DAP |
| Cpd1-ctr | 395 | Corn pedicels control |
| Cpd1-drg | 375 | Corn pedicels drought-stressed |
| Cen8lm | 312 | Corn endosperm 8 DAP |
| Cper5lm | 8 | B73, 5 DAP pericarp |
| Cebho4lm | 5 | Corn embryos Askc0, 15 DAP |
| Cen12lm | 2 | Corn endosperm 12 DAP |

These data are very consistent with limiting this gene's expression to the developing seed.

All publications and patent applications mentioned in the specification are indicative of the level of those skilled in the art to which this invention pertains. All publications and patent applications are herein incorporated by reference to the same extent as if each individual publication or patent application were specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. A transgenic plant comprising a recombinant expression cassette stably integrated into the genome thereof, said cassette comprising a promoter selected from the group consisting of maize zag2.1, maize ZAP, maize tb1, and maize PCNA2, and maize kn1, operably linked to a polynucleotide encoding isopentenyl transferase isolated from *Agrobacterium*, *Arabidopsis*, or *Petunia*, wherein said transgenic plant displays enhanced vigor compared to a corresponding plant without said cassette.

2. Seeds of the transgenic plant of claim 1, wherein said seeds comprise said promoter operably linked to said polynucleotide encoding isopentenyl transferase.

3. The transgenic plant of claim 1, wherein said recombinant expression cassette further comprises one or more enhancer elements.

4. The transgenic plant of claim 3 wherein the enhancer element comprises the 35S enhancer of cauliflower mosaic virus.

5. The transgenic plant of claim 4 wherein the 35S enhancer comprises SEQ ID NO: 4.

6. The transgenic plant of claim 3 wherein the recombinant expression cassette comprises (1) a maize zag2.1 promoter operably linked to the polynucleotide encoding *Agrobacterium* ipt and (2) a cauliflower mosaic virus 35S enhancer.

7. The transgenic plant of claim 6 wherein the recombinant expression cassette comprises (1) SEQ ID NO: 3 operably linked to the coding region of SEQ ID NO: 1 and (2) SEQ ID NO: 4.

8. A method of modulating cytokinin activity in a plant, comprising stably transforming said plant with a recombinant expression cassette comprising a promoter selected from the group consisting of maize zag2.1, maize ZAP, maize tb1, and maize PCNA2, and maize kn1, operably linked to a polynucleotide encoding isopentenyl transferase isolated from *Agrobacterium*, *Arabidopsis*, or *Petunia*, wherein said transgenic plant displays enhanced vigor compared to a corresponding plant without said cassette.

9. The method of claim 8, wherein said recombinant expression cassette further comprises one or more enhancer elements.

10. The method of claim 9 wherein the enhancer element comprises the 35S enhancer of cauliflower mosaic virus.

11. The method of claim 10 wherein the 35S enhancer comprises SEQ ID NO: 4.

12. The method of claim 9 wherein the recombinant expression cassette comprises (1) a maize zag2.1 promoter operably linked to the polynucleotide encoding *Agrobacterium* ipt and (2) a cauliflower mosaic virus 35S enhancer.

13. The method of claim 12 wherein the recombinant expression cassette comprises (1) SEQ ID NO: 3 operably linked to the coding region of SEQ ID NO: 1 and (2) SEQ ID NO: 4.

14. The transgenic plant of claim 1, wherein the plant is maize, soybean, sunflower, safflower, canola, wheat, barley, rye, alfalfa, or sorghum.

15. The transgenic plant of claim 14, wherein the plant is maize or soybean.

* * * * *